US011174507B2

(12) United States Patent
Singer et al.

(10) Patent No.: US 11,174,507 B2
(45) Date of Patent: *Nov. 16, 2021

(54) GENOMIC PROBES

(71) Applicant: Howard Hughes Medical Institute, Chevy Chase, MD (US)

(72) Inventors: Robert Singer, New York, NY (US); Timothee Lionnet, Sterling, VA (US); Wulan Deng, Ashburn, VA (US)

(73) Assignee: HOWARD HUGHES MEDICAL INSTITUTE, Chevy Chase, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/455,342

(22) Filed: Jun. 27, 2019

(65) Prior Publication Data

US 2019/0330678 A1 Oct. 31, 2019

Related U.S. Application Data

(62) Division of application No. 15/519,781, filed as application No. PCT/US2015/056048 on Oct. 16, 2015.

(60) Provisional application No. 62/065,602, filed on Oct. 17, 2014.

(51) Int. Cl.
| | |
|---|---|
| *C12Q 1/683* | (2018.01) |
| *C12Q 1/6841* | (2018.01) |
| *C12Q 1/6804* | (2018.01) |
| *C07H 21/04* | (2006.01) |
| *C12N 15/09* | (2006.01) |
| *C12P 19/34* | (2006.01) |
| *C12Q 1/6809* | (2018.01) |
| *C12Q 1/6855* | (2018.01) |

(52) U.S. Cl.
CPC .............. *C12Q 1/683* (2013.01); *C07H 21/04* (2013.01); *C12N 15/09* (2013.01); *C12P 19/34* (2013.01); *C12Q 1/6804* (2013.01); *C12Q 1/6809* (2013.01); *C12Q 1/6841* (2013.01); *C12Q 1/6855* (2013.01); *C12Q 2531/113* (2013.01)

(58) Field of Classification Search
CPC ................................................ C12N 2310/20
See application file for complete search history.

(56) References Cited

U.S. PATENT DOCUMENTS

| | | | | |
|---|---|---|---|---|
| 2009/0110733 A1* | 4/2009 | Crowther | ................. | A61P 17/02 424/486 |
| 2014/0068797 A1* | 3/2014 | Doudna | ................ | A01K 67/027 800/18 |
| 2014/0179770 A1 | 6/2014 | Zhang et al. | | |
| 2014/0364333 A1* | 12/2014 | Wu | ....................... | C12Q 1/6841 506/9 |
| 2015/0071903 A1* | 3/2015 | Liu | ....................... | C12N 9/1241 424/94.3 |

FOREIGN PATENT DOCUMENTS

WO 2014144155 A1 9/2014

OTHER PUBLICATIONS

Chen et al. (2013) Dynamic Imaging of Genomic Loci in Living Human Cells by an Optimized CRISPR/Cas System. Cell, 155:1479-1491 (Year: 2013).*
Los et al. (2008) HaloTag: A Novel Protein Labeling Technology for Cell Imaging and Protein Analysis. ACS Chemical Biology, 3(6): 373-382 (Year: 2008).*
Sorek et al. (2013) CRISPR-Mediated Adaptive Immune Systems in Bacteria and Archaea. Annual Reviews Biochemistry, 82:237-266 (Year: 2013).*
Koonin et al. (2017) Diversity, classification and evolution of CRISPR-Cas systems. Current Opinion in Microbiology, 37-67-78 (Year: 2017).*
Harrington et al. (2018) Programmed DNA destruction by miniature CRISPR-Cas14 enzymes. Science, 362:839-842 (Year: 2018).*
Chaudhuri et al. (2013) Combined fluorescent in situ hybridization for detection of microRNAs and immunofluorescent labeling for cell-type markers. Frontiers in Cellular Neuroscience, 7(160):1-8 (Year: 2013).*
Grimm et al. (2015) A general method to improve fluorophores for live-cell and single-molecule microscopy. Nature Methods, 12 (3):244-250 (Year: 2015).*
Sung et al. (2014) Highly efficient gene knockout in mice and zebrafish with RNA-guided endonucleases. Genome Research, 24:125-131 (Year: 2014).*
China National Intellectual Property Administration, PRC, Office Action issued in corresponding Application No. 201580069250.3 dated Apr. 1, 2020.

* cited by examiner

*Primary Examiner* — Neil P Hammell

(74) *Attorney, Agent, or Firm* — Stites & Harbison, PLLC; Mandy Wilson Decker

(57) ABSTRACT

Labeled probes, and methods of use thereof, comprise a Cas polypeptide conjugated to gRNA that is specific for target nucleic acid sequences, including genomic DNA sequences. The probes and methods can be used to label nucleic acid sequences without global DNA denaturation.

16 Claims, 15 Drawing Sheets

Specification includes a Sequence Listing.

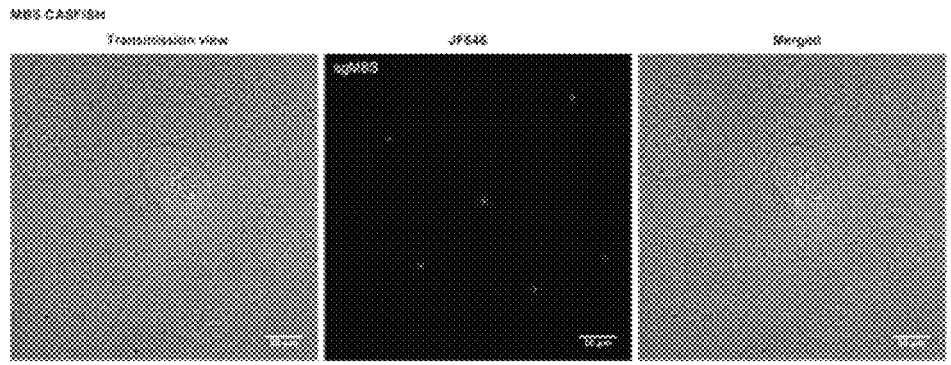
FIG. 4A
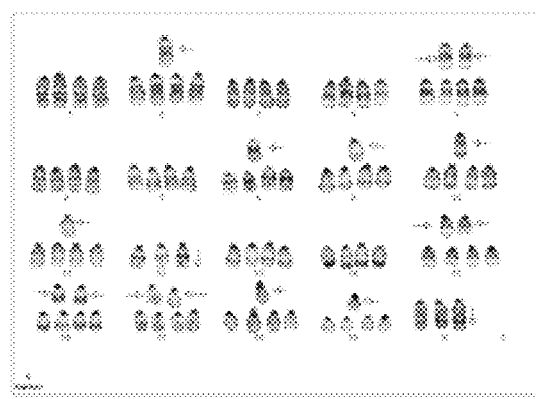
FIG. 4B
FIG. 4C

SEQUENCE LISTING

```
<160> NUMBER OF SEQ ID NOS: 95

<210> SEQ ID NO 1
<211> LENGTH: 5031
<212> TYPE: DNA
<213> ORGANISM: Artificial Sequence
<220> FEATURE:
<223> OTHER INFORMATION: Synthetic
```

<400> SEQUENCE: 1

```
atgcatcatc atcatcatca cgtggataag aaatactcaa taggcttagc tatcggcaca    60
aatagcgtcg gatgggcggt gatcactgat gaatataagg ttccgtctaa aaagttcaag   120
gttctgggaa atacagaccg ccacagtatc aaaaaaaatc ttatagggc tcttttattt   180
gacagtggag agacagcgga agcgactcgt ctcaaacgga cagctcgtag aaggtataca   240
cgtcggaaga atcgtatttg ttatctacag gagattttt caaatgagat ggcgaaagta   300
gatgatagtt tctttcatcg acttgaagag tcttttttgg tggaagaaga caagaagcat   360
gaacgtcatc ctattttgg aaatatagta gatgaagttg cttatcatga gaaatatcca   420
actatctatc atctgcgaaa aaaattggta gattctactg ataaagcgga tttgcgctta   480
atctatttgg ccttagcgca tatgattaag tttcgtggtc atttttgat tgagggagat   540
ttaaatcctg ataatagtga tgtggacaaa ctatttatcc agttggtaca aacctacaat   600
caattatttg aagaaaaccc tattaacgca agtggagtag atgctaaagc gattcttcct   660
gcacgattga gtaaatcaag acgattagaa atctcattg ctcagctccc cggtgagaag   720
aaaaatggct tatttgggaa tctcattgct ttgtcattgg gtttgacccc taattttaaa   780
tcaaattttg atttggcaga gatgctaaaa ttacagcttt caaaagatac ttacgatgat   840
gatttagata attattggc gcaaattgga gatcaatatg ctgatttgtt tttggcagct   900
aagaatttat cagatgctat tttactttca gatatcctaa gagtaaatac tgaaataact   960
aaggctcccc tatcagcttc aatgattaaa cgctacgatg aacatcatca agacttgact  1020
cttttaaaag ctttagttcg acaacaactt ccagaaaagt ataagaaat cttttttgat  1080
caatcaaaaa acggatatgc aggttatatt gatggggag ctagccaaga gaattttat  1140
aaatttatca aaccaatttt agaaaaaatg gatggtactg aggaattatt ggtgaaacta  1200
aatcgtgaag atttgctgcg caagcaacgg accttgaca acggctctat tccccatcaa  1260
attcacttgg gtgagctgca tgctattttg agaagacaag aagacttta tccatttta  1320
aaagacaatc gtgagaagat tgaaaaaatc ttgactttc gaattcctta ttatgttggt  1380
ccattggcgc gtggcaatag tcgttttgca tggatgactc ggaagtctga agaaacaatt  1440
accccatgga attttgaaga agttgtcgat aaaggtgctt cagctcaatc atttattgaa  1500
cgcatgacaa actttgataa aaatcttcca atgaaaaag tactaccaaa acatagtttg  1560
ctttatgagt attttacggt ttataacgaa ttgacaaagg tcaaatatgt tactgaagga  1620
atgcgaaaac cagcatttct ttcaggtgaa cagaagaaag ccattgttga tttactcttc  1680
aaaacaaatc gaaagtaac cgttaagcaa ttaaagaag attatttcaa aaaaatagaa  1740
tgttttgata gtgttgaaat ttcaggagtt gaagatagat ttaatgcttc attaggtacc  1800
taccatgatt tgctaaaaat tattaaagat aaagattttt tggataatga gaaaatgaa  1860
gatatcttag aggatattgt tttaacattg accttatttg aagataggga gatgattgag  1920
gaaagactta aaacatatgc tcacctcttt gatgataagg tgatgaaaca gcttaaacgt  1980
cgccgttata ctggttgggg acgtttgtct cgaaaattga ttaatggtat tagggataag  2040
caatctggca aaacaatatt agatttttg aaatcagatg gttttgccaa tcgcaatttt  2100
atgcagctga tccatgatga tagtttgaca tttaaagaag acattcaaaa agcacaagtg  2160
tctggacaag gcgatagttt acatgaacat attgcaaatt tagctggtag ccctgctatt  2220
aaaaaaggta ttttacagac tgtaaaagtt gttgatgaat tggtcaaagt aatggggcgg  2280
```

```
cataagccag aaaatatcgt tattgaaatg gcacgtgaaa atcagacaac tcaaaagggc    2340
cagaaaaatt cgcgagagcg tatgaaacga atcgaagaag gtatcaaaga attaggaagt    2400
cagattctta aagagcatcc tgttgaaaat actcaattgc aaaatgaaaa gctctatctc    2460
tattatctcc aaaatggaag agacatgtat gtggaccaag aattagatat taatcgttta    2520
agtgattatg atgtcgatgc cattgttcca caaagtttcc ttaaagacga ttcaatagac    2580
aataaggtct taacgcgttc tgataaaaat cgtggtaaat cggataacgt tccaagtgaa    2640
gaagtagtca aaagatgaa  aaactattgg agacaacttc taaacgccaa gttaatcact    2700
caacgtaagt ttgataattt aacgaaagct gaacgtggag gtttgagtga acttgataaa    2760
gctggtttta tcaaacgcca attggttgaa actcgccaaa tcactaagca tgtggcacaa    2820
attttggata gtcgcatgaa tactaaatac gatgaaaatg ataaacttat tcgagaggtt    2880
aaagtgatta ccttaaaatc taaattagtt tctgacttcc gaaaagattt ccaattctat    2940
aaagtacgtg agattaacaa ttaccatcat gcccatgatg cgtatctaaa tgccgtcgtt    3000
ggaactgctt tgattaagaa atatccaaaa cttgaatcgg agtttgtcta tggtgattat    3060
aaagtttatg atgttcgtaa aatgattgct aagtctgagc aagaaatagg caaagcaacc    3120
gcaaaatatt tcttttactc taatatcatg aacttcttca aaacagaaat tacacttgca    3180
aatggagaga ttcgcaaacg ccctctaatc gaaactaatg gggaaactgg agaaattgtc    3240
tgggataaag gcgagatttt tgccacagtg cgcaaagtat tgtccatgcc ccaagtcaat    3300
attgtcaaga aaacagaagt acagacaggc ggattctcca aggagtcaat tttaccaaaa    3360
agaaattcgg acaagcttat tgctcgtaaa aaagactggg atccaaaaaa atatggtggt    3420
tttgatagtc caacggtagc ttattcagtc ctagtggttg ctaaggtgga aaaagggaaa    3480
tcgaagaagt taaaatccgt taaagagtta ctagggatca caattatgga agaagttcc    3540 tttgaaaaaa atccgattga cttttttagaa gctaaaggat ataaggaagt taaaaaagac    3600
ttaatcatta aactacctaa atatagtctt tttgagttag aaaacggtcg taaacggatg    3660
ctggctagtg ccggagaatt acaaaaagga atgagctgg  ctctgccaag caaatatgtg    3720 aatttttttat atttagctag tcattatgaa aagttgaagg gtagtccaga agataacgaa    3780
caaaaacaat tgtttgtgga gcagcataag cattatttag atgagattat tgagcaaatc    3840
agtgaatttt ctaagcgtgt tatttttagca gatgccaatt tagataaagt tcttagtgca    3900
tataacaaac atagagacaa accaatacgt gaacaagcag aaaatattat tcatttatt    3960 acgttgacga atcttggagc tcccgctgct tttaaatatt ttgatacaac aattgatcgt    4020
aaacgatata cgtctacaaa agaagtttta gatgccactc ttatccatca atccatcact    4080 ggtcttatg  aaaacacgcat tgatttgagt cagctaggag gtgacggtgg ctccagatct    4140
gcagaaatcg gtactggctt tccattcgac ccccattatg tggaagtcct gggcgagcgc    4200
atgcactacg tcgatgttgg tccgcgcgat ggcaccctg tgctgttcct gcacggtaac    4260
ccgacctcct cctacgtgtg gcgcaacatc atcccgcatg ttgcaccgac ccatcgctgc    4320
attgctccag acctgatcgg tatgggcaaa tccgacaaac cagacctggg ttatttcttc    4380
gacgaccacg tccgcttcat ggatgccttc atcgaagccc tggtctggga agaggtcgtc    4440
ctggtcattc acgactgggg ctccgctctg ggtttccact gggccaagcg caatccagag    4500
cgcgtcaaag gtattgcatt tatggagttc atccgccctta tcccgacctg gacgaatgg    4560 ccagaatttg cccgcgagac cttccaggcc ttccgcacca ccgacgtcgg ccgcaagctg    4620
atcatcgatc agaacgttttt tatcgagggt acgctgccga tgggtgtcgt ccgcccgctg    4680
```

```
actgaagtcg agatggacca ttaccgcgag ccgttcctga atcctgttga ccgcgagcca    4740
ctgtggcgct tcccaaacga gctgccaatc gccggtgagc agcgaacat cgtcgcgctg     4800 gtcgaagaat acatggactg gctgcaccag tccctgtcc cgaagctgct gttctggggc     4860
accccaggcg ttctgatccc accggccgaa gccgctcgcc tggccaaaag cctgcctaac    4920
tgcaaggctg tggacatcgg cccgggtctg aatctgctgc aagaagacaa cccggacctg    4980
atcggcagcg agatcgcgcg ctggctgtct actctggaga tttccggtta a             5031
```

<210> SEQ ID NO 2
<211> LENGTH: 1676
<212> TYPE: PRT
<213> ORGANISM: Artificial Sequence
<220> FEATURE:
<223> OTHER INFORMATION: Synthetic

<400> SEQUENCE: 2

```
Met His His His His His Val Asp Lys Lys Tyr Ser Ile Gly Leu
1               5                   10                  15

Ala Ile Gly Thr Asn Ser Val Gly Trp Ala Val Ile Thr Asp Glu Tyr
                20                  25                  30

Lys Val Pro Ser Lys Lys Phe Lys Val Leu Gly Asn Thr Asp Arg His
        35                  40                  45

Ser Ile Lys Lys Asn Leu Ile Gly Ala Leu Leu Phe Asp Ser Gly Glu
    50                  55                  60

Thr Ala Glu Ala Thr Arg Leu Lys Arg Thr Ala Arg Arg Arg Tyr Thr
65                  70                  75                  80

Arg Arg Lys Asn Arg Ile Cys Tyr Leu Gln Glu Ile Phe Ser Asn Glu
                85                  90                  95

Met Ala Lys Val Asp Asp Ser Phe Phe His Arg Leu Glu Glu Ser Phe
                100                 105                 110

Leu Val Glu Glu Asp Lys Lys His Glu Arg His Pro Ile Phe Gly Asn
        115                 120                 125

Ile Val Asp Glu Val Ala Tyr His Glu Lys Tyr Pro Thr Ile Tyr His
    130                 135                 140

Leu Arg Lys Lys Leu Val Asp Ser Thr Asp Lys Ala Asp Leu Arg Leu
145                 150                 155                 160

Ile Tyr Leu Ala Leu Ala His Met Ile Lys Phe Arg Gly His Phe Leu
                165                 170                 175

Ile Glu Gly Asp Leu Asn Pro Asp Asn Ser Asp Val Asp Lys Leu Phe
                180                 185                 190

Ile Gln Leu Val Gln Thr Tyr Asn Gln Leu Phe Glu Glu Asn Pro Ile
        195                 200                 205

Asn Ala Ser Gly Val Asp Ala Lys Ala Ile Leu Ser Ala Arg Leu Ser
    210                 215                 220

Lys Ser Arg Arg Leu Glu Asn Leu Ile Ala Gln Leu Pro Gly Glu Lys
225                 230                 235                 240

Lys Asn Gly Leu Phe Gly Asn Leu Ile Ala Leu Ser Leu Gly Leu Thr
                245                 250                 255

Pro Asn Phe Lys Ser Asn Phe Asp Leu Ala Glu Asp Ala Lys Leu Gln
                260                 265                 270

Leu Ser Lys Asp Thr Tyr Asp Asp Asp Leu Asp Asn Leu Leu Ala Gln
        275                 280                 285

Ile Gly Asp Gln Tyr Ala Asp Leu Phe Leu Ala Ala Lys Asn Leu Ser
    290                 295                 300
```

```
Asp Ala Ile Leu Leu Ser Asp Ile Leu Arg Val Asn Thr Glu Ile Thr
305                 310                 315                 320

Lys Ala Pro Leu Ser Ala Ser Met Ile Lys Arg Tyr Asp Glu His His
            325                 330                 335

Gln Asp Leu Thr Leu Leu Lys Ala Leu Val Arg Gln Gln Leu Pro Glu
                340                 345                 350

Lys Tyr Lys Glu Ile Phe Phe Asp Gln Ser Lys Asn Gly Tyr Ala Gly
            355                 360                 365

Tyr Ile Asp Gly Gly Ala Ser Gln Glu Glu Phe Tyr Lys Phe Ile Lys
370                 375                 380

Pro Ile Leu Glu Lys Met Asp Gly Thr Glu Glu Leu Leu Val Lys Leu
385                 390                 395                 400

Asn Arg Glu Asp Leu Leu Arg Lys Gln Arg Thr Phe Asp Asn Gly Ser
                405                 410                 415

Ile Pro His Gln Ile His Leu Gly Glu Leu His Ala Ile Leu Arg Arg
                420                 425                 430

Gln Glu Asp Phe Tyr Pro Phe Leu Lys Asp Asn Arg Glu Lys Ile Glu
            435                 440                 445

Lys Ile Leu Thr Phe Arg Ile Pro Tyr Tyr Val Gly Pro Leu Ala Arg
450                 455                 460

Gly Asn Ser Arg Phe Ala Trp Met Thr Arg Lys Ser Glu Glu Thr Ile
465                 470                 475                 480

Thr Pro Trp Asn Phe Glu Glu Val Val Asp Lys Gly Ala Ser Ala Gln
                485                 490                 495

Ser Phe Ile Glu Arg Met Thr Asn Phe Asp Lys Asn Leu Pro Asn Glu
                500                 505                 510

Lys Val Leu Pro Lys His Ser Leu Leu Tyr Glu Tyr Phe Thr Val Tyr
            515                 520                 525

Asn Glu Leu Thr Lys Val Lys Tyr Val Thr Glu Gly Met Arg Lys Pro
530                 535                 540

Ala Phe Leu Ser Gly Glu Gln Lys Lys Ala Ile Val Asp Leu Leu Phe
545                 550                 555                 560

Lys Thr Asn Arg Lys Val Thr Val Lys Gln Leu Lys Glu Asp Tyr Phe
                565                 570                 575

Lys Lys Ile Glu Cys Phe Asp Ser Val Glu Ile Ser Gly Val Glu Asp
            580                 585                 590

Arg Phe Asn Ala Ser Leu Gly Thr Tyr His Asp Leu Leu Lys Ile Ile
            595                 600                 605

Lys Asp Lys Asp Phe Leu Asp Asn Glu Glu Asn Glu Asp Ile Leu Glu
            610                 615                 620

Asp Ile Val Leu Thr Leu Thr Leu Phe Glu Asp Arg Glu Met Ile Glu
625                 630                 635                 640

Glu Arg Leu Lys Thr Tyr Ala His Leu Phe Asp Asp Lys Val Met Lys
                645                 650                 655

Gln Leu Lys Arg Arg Arg Tyr Thr Gly Trp Gly Arg Leu Ser Arg Lys
                660                 665                 670

Leu Ile Asn Gly Ile Arg Asp Lys Gln Ser Gly Lys Thr Ile Leu Asp
            675                 680                 685

Phe Leu Lys Ser Asp Gly Phe Ala Asn Arg Asn Phe Met Gln Leu Ile
            690                 695                 700

His Asp Asp Ser Leu Thr Phe Lys Glu Asp Ile Gln Lys Ala Gln Val
705                 710                 715                 720
```

```
Ser Gly Gln Gly Asp Ser Leu His Glu His Ile Ala Asn Leu Ala Gly
            725                 730                 735

Ser Pro Ala Ile Lys Lys Gly Ile Leu Gln Thr Val Lys Val Val Asp
            740                 745                 750

Glu Leu Val Lys Val Met Gly Arg His Lys Pro Glu Asn Ile Val Ile
            755                 760                 765

Glu Met Ala Arg Glu Asn Gln Thr Thr Gln Lys Gly Gln Lys Asn Ser
            770                 775                 780

Arg Glu Arg Met Lys Arg Ile Glu Glu Gly Ile Lys Glu Leu Gly Ser
785                 790                 795                 800

Gln Ile Leu Lys Glu His Pro Val Glu Asn Thr Gln Leu Gln Asn Glu
            805                 810                 815

Lys Leu Tyr Leu Tyr Tyr Leu Gln Asn Gly Arg Asp Met Tyr Val Asp
            820                 825                 830

Gln Glu Leu Asp Ile Asn Arg Leu Ser Asp Tyr Asp Val Asp Ala Ile
            835                 840                 845

Val Pro Gln Ser Phe Leu Lys Asp Asp Ser Ile Asp Asn Lys Val Leu
            850                 855                 860

Thr Arg Ser Asp Lys Asn Arg Gly Lys Ser Asp Asn Val Pro Ser Glu
865                 870                 875                 880

Glu Val Val Lys Lys Met Lys Asn Tyr Trp Arg Gln Leu Leu Asn Ala
            885                 890                 895

Lys Leu Ile Thr Gln Arg Lys Phe Asp Asn Leu Thr Lys Ala Glu Arg
            900                 905                 910

Gly Gly Leu Ser Glu Leu Asp Lys Ala Gly Phe Ile Lys Arg Gln Leu
            915                 920                 925

Val Glu Thr Arg Gln Ile Thr Lys His Val Ala Gln Ile Leu Asp Ser
            930                 935                 940

Arg Met Asn Thr Lys Tyr Asp Glu Asn Asp Lys Leu Ile Arg Glu Val
945                 950                 955                 960

Lys Val Ile Thr Leu Lys Ser Lys Leu Val Ser Asp Phe Arg Lys Asp
            965                 970                 975

Phe Gln Phe Tyr Lys Val Arg Glu Ile Asn Asn Tyr His His Ala His
            980                 985                 990

Asp Ala Tyr Leu Asn Ala Val Val Gly Thr Ala Leu Ile Lys Lys Tyr
            995                 1000                1005

Pro Lys Leu Glu Ser Glu Phe Val Tyr Gly Asp Tyr Lys Val Tyr
            1010                1015                1020

Asp Val Arg Lys Met Ile Ala Lys Ser Glu Gln Glu Ile Gly Lys
            1025                1030                1035

Ala Thr Ala Lys Tyr Phe Phe Tyr Ser Asn Ile Met Asn Phe Phe
            1040                1045                1050

Lys Thr Glu Ile Thr Leu Ala Asn Gly Glu Ile Arg Lys Arg Pro
            1055                1060                1065

Leu Ile Glu Thr Asn Gly Glu Thr Gly Glu Ile Val Trp Asp Lys
            1070                1075                1080

Gly Arg Asp Phe Ala Thr Val Arg Lys Val Leu Ser Met Pro Gln
            1085                1090                1095

Val Asn Ile Val Lys Lys Thr Glu Val Gln Thr Gly Gly Phe Ser
            1100                1105                1110

Lys Glu Ser Ile Leu Pro Lys Arg Asn Ser Asp Lys Leu Ile Ala
            1115                1120                1125

Arg Lys Lys Asp Trp Asp Pro Lys Lys Tyr Gly Gly Phe Asp Ser
```

-continued

```
            1130                1135                1140

Pro Thr Val Ala Tyr Ser Val Leu Val Ala Lys Val Glu Lys
            1145                1150                1155

Gly Lys Ser Lys Lys Leu Lys Ser Val Lys Glu Leu Leu Gly Ile
            1160                1165                1170

Thr Ile Met Glu Arg Ser Ser Phe Glu Lys Asn Pro Ile Asp Phe
            1175                1180                1185

Leu Glu Ala Lys Gly Tyr Lys Glu Val Lys Lys Asp Leu Ile Ile
            1190                1195                1200

Lys Leu Pro Lys Tyr Ser Leu Phe Glu Leu Glu Asn Gly Arg Lys
            1205                1210                1215

Arg Met Leu Ala Ser Ala Gly Glu Leu Gln Lys Gly Asn Glu Leu
            1220                1225                1230

Ala Leu Pro Ser Lys Tyr Val Asn Phe Leu Tyr Leu Ala Ser His
            1235                1240                1245

Tyr Glu Lys Leu Lys Gly Ser Pro Glu Asp Asn Glu Gln Lys Gln
            1250                1255                1260

Leu Phe Val Glu Gln His Lys His Tyr Leu Asp Glu Ile Ile Glu
            1265                1270                1275

Gln Ile Ser Glu Phe Ser Lys Arg Val Ile Leu Ala Asp Ala Asn
            1280                1285                1290

Leu Asp Lys Val Leu Ser Ala Tyr Asn Lys His Arg Asp Lys Pro
            1295                1300                1305

Ile Arg Glu Gln Ala Glu Asn Ile Ile His Leu Phe Thr Leu Thr
            1310                1315                1320

Asn Leu Gly Ala Pro Ala Ala Phe Lys Tyr Phe Asp Thr Thr Ile
            1325                1330                1335

Asp Arg Lys Arg Tyr Thr Ser Thr Lys Glu Val Leu Asp Ala Thr
            1340                1345                1350

Leu Ile His Gln Ser Ile Thr Gly Leu Tyr Glu Thr Arg Ile Asp
            1355                1360                1365

Leu Ser Gln Leu Gly Gly Asp Gly Gly Ser Arg Ser Ala Glu Ile
            1370                1375                1380

Gly Thr Gly Phe Pro Phe Asp Pro His Tyr Val Glu Val Leu Gly
            1385                1390                1395

Glu Arg Met His Tyr Val Asp Val Gly Pro Arg Asp Gly Thr Pro
            1400                1405                1410

Val Leu Phe Leu His Gly Asn Pro Thr Ser Ser Tyr Val Trp Arg
            1415                1420                1425

Asn Ile Ile Pro His Val Ala Pro Thr His Arg Cys Ile Ala Pro
            1430                1435                1440

Asp Leu Ile Gly Met Gly Lys Ser Asp Lys Pro Asp Leu Gly Tyr
            1445                1450                1455

Phe Phe Asp Asp His Val Arg Phe Met Asp Ala Phe Ile Glu Ala
            1460                1465                1470

Leu Gly Leu Glu Glu Val Val Leu Val Ile His Asp Trp Gly Ser
            1475                1480                1485

Ala Leu Gly Phe His Trp Ala Lys Arg Asn Pro Glu Arg Val Lys
            1490                1495                1500

Gly Ile Ala Phe Met Glu Phe Ile Arg Pro Ile Pro Thr Trp Asp
            1505                1510                1515

Glu Trp Pro Glu Phe Ala Arg Glu Thr Phe Gln Ala Phe Arg Thr
            1520                1525                1530
```

Thr Asp Val Gly Arg Lys Leu Ile Ile Asp Gln Asn Val Phe Ile
    1535                1540                1545

Glu Gly Thr Leu Pro Met Gly Val Val Arg Pro Leu Thr Glu Val
    1550                1555                1560

Glu Met Asp His Tyr Arg Glu Pro Phe Leu Asn Pro Val Asp Arg
    1565                1570                1575

Glu Pro Leu Trp Arg Phe Pro Asn Glu Leu Pro Ile Ala Gly Glu
    1580                1585                1590

Pro Ala Asn Ile Val Ala Leu Val Glu Glu Tyr Met Asp Trp Leu
    1595                1600                1605

His Gln Ser Pro Val Pro Lys Leu Leu Phe Trp Gly Thr Pro Gly
    1610                1615                1620

Val Leu Ile Pro Pro Ala Glu Ala Ala Arg Leu Ala Lys Ser Leu
    1625                1630                1635

Pro Asn Cys Lys Ala Val Asp Ile Gly Pro Gly Leu Asn Leu Leu
    1640                1645                1650

Gln Glu Asp Asn Pro Asp Leu Ile Gly Ser Glu Ile Ala Arg Trp
    1655                1660                1665

Leu Ser Thr Leu Glu Ile Ser Gly
    1670                1675

<210> SEQ ID NO 3
<211> LENGTH: 5127
<212> TYPE: DNA
<213> ORGANISM: Artificial Sequence
<220> FEATURE:
<223> OTHER INFORMATION: Synthetic

<400> SEQUENCE: 3

```
atgcatccaa agaagaagcg aaggtcggt  atccacggag tcccagcagc ccatcatcat     60
catcatcacg tggataagaa atactcaata ggcttagcta tcggcacaaa tagcgtcgga    120
tgggcggtga tcactgatga atataaggtt ccgtctaaaa agttcaaggt tctgggaaat    180
acagaccgcc acagtatcaa aaaaaatctt atagggctc  ttttatttga cagtggagag    240
acagcggaag cgactcgtct caaacggaca gctcgtagaa ggtatacacg tcggaagaat    300
cgtatttgtt atctacagga gattttttca aatgagatgg cgaaagtaga tgatagtttc    360
tttcatcgac ttgaagagtc ttttttggtg gaagaagaca agaagcatga acgtcatcct    420
atttttggaa atatagtaga tgaagttgct tatcatgaga aatatccaac tatctatcat    480
ctgcgaaaaa aattggtaga ttctactgat aaagcggatt gcgcttaat  ctatttggcc    540
ttagcgcata tgattaagtt tcgtggtcat tttttgattg agggagattt aaatcctgat    600
aatagtgatg tggacaaact attatccag  ttggtacaaa cctacaatca attatttgaa    660
gaaaacccta ttaacgcaag tggagtagat gctaaagcga ttctttctgc acgattgagt    720
aaatcaagac gattagaaaa tctcattgct cagctccccg tgagaagaa  aaatggctta    780
tttgggaatc tcattgcttt tgtcattggt ttgaccccta attttaaatc aaattttgat    840
ttggcagaag atgctaaatt acagctttca aaagatactt acgatgatga tttagataat    900
ttattggcgc aaattggaga tcaatatgct gatttgtttt tggcagctaa gaattatca    960
gatgctattt tacttcaga  atatccaaga gtaaatactg aataactaa  ggctccccta   1020
tcagcttcaa tgattaaacg ctacgatgaa catcatcaag acttgactct tttaaaagct   1080
ttagttcgac aacaacttcc agaaaagtat aaagaaatct ttttgatca  atcaaaaaac   1140
```

```
ggatatgcag gttatattga tgggggagct agccaagaag aattttataa atttatcaaa    1200
ccaattttag aaaaaatgga tggtactgag gaattattgg tgaaactaaa tcgtgaagat    1260
ttgctgcgca agcaacggac cttttgacaac ggctctattc cccatcaaat tcacttgggt   1320
gagctgcatg ctattttgag aagacaagaa gacttttatc cattttttaaa agacaatcgt   1380 gagaagattg aaaaaatctt gacttttcga attccttatt atgttggtcc attggcgcgt    1440
ggcaatagtc gttttgcatg gatgactcgg aagtctgaag aaacaattac cccatggaat    1500
tttgaagaag ttgtcgataa aggtgcttca gctcaatcat ttattgaacg catgacaaac    1560
tttgataaaa atcttccaaa tgaaaaagta ctaccaaaac atagtttgct ttatgagtat    1620
tttacggttt ataacgaatt gacaaaggtc aaatatgtta ctgaaggaat gcgaaaacca    1680
gcatttcttt caggtgaaca gaagaaagcc attgttgatt tactcttcaa aacaaatcga    1740
aaagtaaccg ttaagcaatt aaaagaagat tatttcaaaa aatagaatg tttttgatagt    1800 gttgaaattt caggagttga agatagattt aatgcttcat taggtaccta ccatgatttg    1860
ctaaaaatta ttaaagataa agattttttg gataatgaag aaaatgaaga tatcttagag    1920
gatattgttt taacattgac cttatttgaa gatagggaga tgattgagga aagacttaaa    1980
acatatgctc acctctttga tgataaggtg atgaaacagc ttaaacgtcg ccgttatact    2040
ggttggggac gtttgtctcg aaaattgatt aatggtatta gggataagca atctggcaaa    2100
acaatattag attttttgaa atcagatggt tttgccaatc gcaattttat gcagctgatc    2160
catgatgata gtttgacatt taagaagac attcaaaaag cacaagtgtc tggacaaggc    2220
gatagtttac atgaacatat tgcaaattta gctggtagcc ctgctattaa aaaaggtatt    2280
ttacagactg taaagttgt tgatgaattg gtcaaagtaa tggggcggca taagccagaa    2340
aatatcgtta ttgaaatggc acgtgaaaat cagacaactc aaaagggcca gaaaaattcg    2400
cgagagcgta tgaaacgaat cgaagaaggt atcaagaat taggaagtca gattcttaaa    2460
gagcatcctg ttgaaaatac tcaattgcaa atgaaaaagc tctatctcta ttatctccaa    2520
aatggaagag acatgtatgt ggaccaagaa ttagatatta atcgtttaag tgattatgat    2580
gtcgatgcca ttgttccaca aagttttcctt aaagacgatt caatagacaa taaggtctta    2640
acgcgttctg ataaaaatcg tggtaaatcg gataacgttc caagtgaaga agtagtcaaa    2700
aagatgaaaa actattggag acaacttcta acgccaagt taatcactca acgtaagttt    2760 gataattaa cgaaagctga acgtggaggt ttgagtgaac ttgataaagc tggttttatc    2820
aaacgccaat tggttgaaac tcgccaaatc actaagcatg tggcacaaat tttggatagt    2880
cgcatgaata ctaaatacga tgaaaatgat aaacttattc gagaggttaa agtgattacc    2940
ttaaaatcta aattagtttc tgacttccga aaagatttcc aattctataa agtacgtgag    3000
attaacaatt accatcatgc ccatgatgcg tatctaaatg ccgtcgttgg aactgctttg    3060
attaagaaat atccaaaact tgaatcggag tttgtctatg gtgattataa agtttatgat    3120
gttcgtaaaa tgattgctaa gtctgagcaa gaaataggca aagcaaccgc aaaatattc    3180 ttttactcta atatcatgaa cttcttcaaa acagaaatta cacttgcaaa tggagagatt    3240
cgcaaacgcc ctctaatcga aactaatggg gaaactggag aaattgtctg gataaaggg    3300 cgagattttg ccacagtgcg caaagtattg tccatgcccc aagtcaatat tgtcaagaaa    3360
acagaagtac agacaggcgg attctccaag gagtcaattt taccaaaaag aaattcggac    3420
aagcttattc tcgtaaaaaa agactgggat ccaaaaaaat atggtggttt tgatagtcca    3480
acggtagctt attcagtcct agtggttgct aaggtggaaa aagggaaatc gaagaagtta    3540
```

```
aaatccgtta aagagttact agggatcaca attatggaaa gaagttcctt tgaaaaaaat   3600
ccgattgact ttttagaagc taaaggatat aaggaagtta aaaaagactt aatcattaaa   3660
ctacctaaat atagtctttt tgagttagaa acggtcgta aacggatgct ggctagtgcc    3720
ggagaattac aaaaaggaaa tgagctggct ctgccaagca aatatgtgaa ttttttatat   3780
ttagctagtc attatgaaaa gttgaagggt agtccagaag ataacgaaca aaaacaattg   3840
tttgtggagc agcataagca ttatttagat gagattattg agcaaatcag tgaattttct   3900
aagcgtgtta ttttagcaga tgccaattta gataaagttc ttagtgcata taacaaacat   3960
agagacaaac caatacgtga acaagcagaa aatattattc atttatttac gttgacgaat   4020
cttggagctc ccgctgcttt taaatatttt gatacaacaa ttgatcgtaa acgatatacg   4080
tctacaaaag aagttttaga tgccactctt atccatcaat ccatcactgg tctttatgaa   4140
acacgcattg atttgagtca gctaggaggt gacggtggct ccagatctgc agaaatcggt   4200
actggctttc cattcgaccc ccattatgtg gaagtcctgg gcgagcgcat gcactacgtc   4260
gatgttggtc cgcgcgatgg caccctgtg ctgttcctgc acggtaaccc gacctcctcc    4320
tacgtgtggc gcaacatcat cccgcatgtt gcaccgaccc atcgctgcat tgctccagac   4380
ctgatcggta tgggcaaatc cgacaaacca gacctgggtt atttcttcga cgaccacgtc   4440
cgcttcatgg atgccttcat cgaagccctg ggtctggaag aggtcgtcct ggtcattcac   4500
gactggggct ccgctctggg tttccactgg gccaagcgca atccagagcg cgtcaaaggt   4560
attgcattta tggagttcat ccgccctatc ccgacctggg acgaatggcc agaatttgcc   4620
cgcgagacct tccaggcctt ccgcaccacc gacgtcggcc gcaagctgat catcgatcag   4680
aacgttttta tcgagggtac gctgccgatg ggtgtcgtcc gcccgctgac tgaagtcgag   4740
atggaccatt accgcgagcc gttcctgaat cctgttgacc gcgagccact gtggcgcttc   4800
ccaaacgagc tgccaatcgc cggtgagcca gcgaacatcg tcgcgctggt cgaagaatac   4860
atggactggc tgcaccagtc ccctgtcccg aagctgctgt tctggggcac ccaggcgtt    4920
ctgatcccac cggccgaagc cgctcgcctg gccaaaagcc tgcctaactg caaggctgtg   4980
gacatcggcc cgggtctgaa tctgctgcaa gaagacaacc cggacctgat cggcagcgag   5040
atcgcgcgct ggctgtctac tctggagatt ccggtaagc gtcctgctgc tactaagaaa    5100
gctggtcaag ctaagaaaaa gaaataa                                       5127
```

<210> SEQ ID NO 4
<211> LENGTH: 1708
<212> TYPE: PRT
<213> ORGANISM: Artificial Sequence
<220> FEATURE:
<223> OTHER INFORMATION: Synthetic

<400> SEQUENCE: 4

Met His Pro Lys Lys Arg Lys Val Gly Ile His Gly Val Pro Ala
1               5                   10                  15

Ala His His His His His His Val Asp Lys Lys Tyr Ser Ile Gly Leu
            20                  25                  30

Ala Ile Gly Thr Asn Ser Val Gly Trp Ala Val Ile Thr Asp Glu Tyr
        35                  40                  45

Lys Val Pro Ser Lys Lys Phe Lys Val Leu Gly Asn Thr Asp Arg His
    50                  55                  60

Ser Ile Lys Lys Asn Leu Ile Gly Ala Leu Leu Phe Asp Ser Gly Glu
65                  70                  75                  80

-continued

```
Thr Ala Glu Ala Thr Arg Leu Lys Arg Thr Ala Arg Arg Tyr Thr
                85                  90                  95

Arg Arg Lys Asn Arg Ile Cys Tyr Leu Gln Glu Ile Phe Ser Asn Glu
                100                 105                 110

Met Ala Lys Val Asp Asp Ser Phe Phe His Arg Leu Glu Glu Ser Phe
            115                 120                 125

Leu Val Glu Glu Asp Lys Lys His Glu Arg His Pro Ile Phe Gly Asn
        130                 135                 140

Ile Val Asp Glu Val Ala Tyr His Glu Lys Tyr Pro Thr Ile Tyr His
145                 150                 155                 160

Leu Arg Lys Lys Leu Val Asp Ser Thr Asp Lys Ala Asp Leu Arg Leu
                165                 170                 175

Ile Tyr Leu Ala Leu Ala His Met Ile Lys Phe Arg Gly His Phe Leu
                180                 185                 190

Ile Glu Gly Asp Leu Asn Pro Asp Asn Ser Asp Val Asp Lys Leu Phe
            195                 200                 205

Ile Gln Leu Val Gln Thr Tyr Asn Gln Leu Phe Glu Glu Asn Pro Ile
        210                 215                 220

Asn Ala Ser Gly Val Asp Ala Lys Ala Ile Leu Ser Ala Arg Leu Ser
225                 230                 235                 240

Lys Ser Arg Arg Leu Glu Asn Leu Ile Ala Gln Leu Pro Gly Glu Lys
                245                 250                 255

Lys Asn Gly Leu Phe Gly Asn Leu Ile Ala Leu Ser Leu Gly Leu Thr
                260                 265                 270

Pro Asn Phe Lys Ser Asn Phe Asp Leu Ala Glu Asp Ala Lys Leu Gln
            275                 280                 285

Leu Ser Lys Asp Thr Tyr Asp Asp Asp Leu Asp Asn Leu Leu Ala Gln
        290                 295                 300

Ile Gly Asp Gln Tyr Ala Asp Leu Phe Leu Ala Ala Lys Asn Leu Ser
305                 310                 315                 320

Asp Ala Ile Leu Leu Ser Asp Ile Leu Arg Val Asn Thr Glu Ile Thr
                325                 330                 335

Lys Ala Pro Leu Ser Ala Ser Met Ile Lys Arg Tyr Asp Glu His His
                340                 345                 350

Gln Asp Leu Thr Leu Leu Lys Ala Leu Val Arg Gln Gln Leu Pro Glu
            355                 360                 365

Lys Tyr Lys Glu Ile Phe Phe Asp Gln Ser Lys Asn Gly Tyr Ala Gly
        370                 375                 380

Tyr Ile Asp Gly Gly Ala Ser Gln Glu Glu Phe Tyr Lys Phe Ile Lys
385                 390                 395                 400

Pro Ile Leu Glu Lys Met Asp Gly Thr Glu Glu Leu Leu Val Lys Leu
                405                 410                 415

Asn Arg Glu Asp Leu Leu Arg Lys Gln Arg Thr Phe Asp Asn Gly Ser
                420                 425                 430

Ile Pro His Gln Ile His Leu Gly Glu Leu His Ala Ile Leu Arg Arg
            435                 440                 445

Gln Glu Asp Phe Tyr Pro Phe Leu Lys Asp Asn Arg Glu Lys Ile Glu
        450                 455                 460

Lys Ile Leu Thr Phe Arg Ile Pro Tyr Tyr Val Gly Pro Leu Ala Arg
465                 470                 475                 480

Gly Asn Ser Arg Phe Ala Trp Met Thr Arg Lys Ser Glu Glu Thr Ile
                485                 490                 495
```

```
Thr Pro Trp Asn Phe Glu Glu Val Val Asp Lys Gly Ala Ser Ala Gln
            500                 505                 510

Ser Phe Ile Glu Arg Met Thr Asn Phe Asp Lys Asn Leu Pro Asn Glu
            515                 520                 525

Lys Val Leu Pro Lys His Ser Leu Leu Tyr Glu Tyr Phe Thr Val Tyr
            530                 535                 540

Asn Glu Leu Thr Lys Val Lys Tyr Val Thr Glu Gly Met Arg Lys Pro
545                 550                 555                 560

Ala Phe Leu Ser Gly Glu Gln Lys Lys Ala Ile Val Asp Leu Leu Phe
            565                 570                 575

Lys Thr Asn Arg Lys Val Thr Val Lys Gln Leu Lys Glu Asp Tyr Phe
            580                 585                 590

Lys Lys Ile Glu Cys Phe Asp Ser Val Glu Ile Ser Gly Val Glu Asp
            595                 600                 605

Arg Phe Asn Ala Ser Leu Gly Thr Tyr His Asp Leu Leu Lys Ile Ile
            610                 615                 620

Lys Asp Lys Asp Phe Leu Asp Asn Glu Glu Asn Glu Asp Ile Leu Glu
625                 630                 635                 640

Asp Ile Val Leu Thr Leu Thr Leu Phe Glu Asp Arg Glu Met Ile Glu
            645                 650                 655

Glu Arg Leu Lys Thr Tyr Ala His Leu Phe Asp Asp Lys Val Met Lys
            660                 665                 670

Gln Leu Lys Arg Arg Arg Tyr Thr Gly Trp Gly Arg Leu Ser Arg Lys
            675                 680                 685

Leu Ile Asn Gly Ile Arg Asp Lys Gln Ser Gly Lys Thr Ile Leu Asp
            690                 695                 700

Phe Leu Lys Ser Asp Gly Phe Ala Asn Arg Asn Phe Met Gln Leu Ile
705                 710                 715                 720

His Asp Asp Ser Leu Thr Phe Lys Glu Asp Ile Gln Lys Ala Gln Val
            725                 730                 735

Ser Gly Gln Gly Asp Ser Leu His Glu His Ile Ala Asn Leu Ala Gly
            740                 745                 750

Ser Pro Ala Ile Lys Lys Gly Ile Leu Gln Thr Val Lys Val Val Asp
            755                 760                 765

Glu Leu Val Lys Val Met Gly Arg His Lys Pro Glu Asn Ile Val Ile
770                 775                 780

Glu Met Ala Arg Glu Asn Gln Thr Thr Gln Lys Gly Gln Lys Asn Ser
785                 790                 795                 800

Arg Glu Arg Met Lys Arg Ile Glu Glu Gly Ile Lys Glu Leu Gly Ser
            805                 810                 815

Gln Ile Leu Lys Glu His Pro Val Glu Asn Thr Gln Leu Gln Asn Glu
            820                 825                 830

Lys Leu Tyr Leu Tyr Tyr Leu Gln Asn Gly Arg Asp Met Tyr Val Asp
            835                 840                 845

Gln Glu Leu Asp Ile Asn Arg Leu Ser Asp Tyr Asp Val Asp Ala Ile
            850                 855                 860

Val Pro Gln Ser Phe Leu Lys Asp Asp Ser Ile Asp Asn Lys Val Leu
865                 870                 875                 880

Thr Arg Ser Asp Lys Asn Arg Gly Lys Ser Asp Asn Val Pro Ser Glu
            885                 890                 895

Glu Val Val Lys Lys Met Lys Asn Tyr Trp Arg Gln Leu Leu Asn Ala
            900                 905                 910

Lys Leu Ile Thr Gln Arg Lys Phe Asp Asn Leu Thr Lys Ala Glu Arg
```

-continued

```
           915                 920                 925
Gly Gly Leu Ser Glu Leu Asp Lys Ala Gly Phe Ile Lys Arg Gln Leu
       930                 935                 940
Val Glu Thr Arg Gln Ile Thr Lys His Val Ala Gln Ile Leu Asp Ser
945                 950                 955                 960
Arg Met Asn Thr Lys Tyr Asp Glu Asn Asp Lys Leu Ile Arg Glu Val
                965                 970                 975
Lys Val Ile Thr Leu Lys Ser Lys Leu Val Ser Asp Phe Arg Lys Asp
                980                 985                 990
Phe Gln Phe Tyr Lys Val Arg Glu Ile Asn Asn Tyr His His Ala His
            995                1000                1005
Asp Ala Tyr Leu Asn Ala Val Val Gly Thr Ala Leu Ile Lys Lys
       1010                1015                1020
Tyr Pro Lys Leu Glu Ser Glu Phe Val Tyr Gly Asp Tyr Lys Val
       1025                1030                1035
Tyr Asp Val Arg Lys Met Ile Ala Lys Ser Glu Gln Glu Ile Gly
       1040                1045                1050
Lys Ala Thr Ala Lys Tyr Phe Phe Tyr Ser Asn Ile Met Asn Phe
       1055                1060                1065
Phe Lys Thr Glu Ile Thr Leu Ala Asn Gly Glu Ile Arg Lys Arg
       1070                1075                1080
Pro Leu Ile Glu Thr Asn Gly Glu Thr Gly Glu Ile Val Trp Asp
       1085                1090                1095
Lys Gly Arg Asp Phe Ala Thr Val Arg Lys Val Leu Ser Met Pro
       1100                1105                1110
Gln Val Asn Ile Val Lys Lys Thr Glu Val Gln Thr Gly Gly Phe
       1115                1120                1125
Ser Lys Glu Ser Ile Leu Pro Lys Arg Asn Ser Asp Lys Leu Ile
       1130                1135                1140
Ala Arg Lys Lys Asp Trp Asp Pro Lys Lys Tyr Gly Gly Phe Asp
       1145                1150                1155
Ser Pro Thr Val Ala Tyr Ser Val Leu Val Val Ala Lys Val Glu
       1160                1165                1170
Lys Gly Lys Ser Lys Lys Leu Lys Ser Val Lys Glu Leu Leu Gly
       1175                1180                1185
Ile Thr Ile Met Glu Arg Ser Ser Phe Glu Lys Asn Pro Ile Asp
       1190                1195                1200
Phe Leu Glu Ala Lys Gly Tyr Lys Glu Val Lys Lys Asp Leu Ile
       1205                1210                1215
Ile Lys Leu Pro Lys Tyr Ser Leu Phe Glu Leu Glu Asn Gly Arg
       1220                1225                1230
Lys Arg Met Leu Ala Ser Ala Gly Glu Leu Gln Lys Gly Asn Glu
       1235                1240                1245
Leu Ala Leu Pro Ser Lys Tyr Val Asn Phe Leu Tyr Leu Ala Ser
       1250                1255                1260
His Tyr Glu Lys Leu Lys Gly Ser Pro Glu Asp Asn Glu Gln Lys
       1265                1270                1275
Gln Leu Phe Val Glu Gln His Lys His Tyr Leu Asp Glu Ile Ile
       1280                1285                1290
Glu Gln Ile Ser Glu Phe Ser Lys Arg Val Ile Leu Ala Asp Ala
       1295                1300                1305
Asn Leu Asp Lys Val Leu Ser Ala Tyr Asn Lys His Arg Asp Lys
       1310                1315                1320
```

```
Pro Ile Arg Glu Gln Ala Glu Asn Ile Ile His Leu Phe Thr Leu
    1325                1330                1335

Thr Asn Leu Gly Ala Pro Ala Phe Lys Tyr Phe Asp Thr Thr
    1340                1345                1350

Ile Asp Arg Lys Arg Tyr Thr Ser Thr Lys Glu Val Leu Asp Ala
    1355                1360                1365

Thr Leu Ile His Gln Ser Ile Thr Gly Leu Tyr Glu Thr Arg Ile
    1370                1375                1380

Asp Leu Ser Gln Leu Gly Gly Asp Gly Gly Ser Arg Ser Ala Glu
    1385                1390                1395

Ile Gly Thr Gly Phe Pro Phe Asp Pro His Tyr Val Glu Val Leu
    1400                1405                1410

Gly Glu Arg Met His Tyr Val Asp Val Gly Pro Arg Asp Gly Thr
    1415                1420                1425

Pro Val Leu Phe Leu His Gly Asn Pro Thr Ser Ser Tyr Val Trp
    1430                1435                1440

Arg Asn Ile Ile Pro His Val Ala Pro Thr His Arg Cys Ile Ala
    1445                1450                1455

Pro Asp Leu Ile Gly Met Gly Lys Ser Asp Lys Pro Asp Leu Gly
    1460                1465                1470

Tyr Phe Phe Asp Asp His Val Arg Phe Met Asp Ala Phe Ile Glu
    1475                1480                1485

Ala Leu Gly Leu Glu Glu Val Val Leu Val Ile His Asp Trp Gly
    1490                1495                1500

Ser Ala Leu Gly Phe His Trp Ala Lys Arg Asn Pro Glu Arg Val
    1505                1510                1515

Lys Gly Ile Ala Phe Met Glu Phe Ile Arg Pro Ile Pro Thr Trp
    1520                1525                1530

Asp Glu Trp Pro Glu Phe Ala Arg Glu Thr Phe Gln Ala Phe Arg
    1535                1540                1545

Thr Thr Asp Val Gly Arg Lys Leu Ile Ile Asp Gln Asn Val Phe
    1550                1555                1560

Ile Glu Gly Thr Leu Pro Met Gly Val Val Arg Pro Leu Thr Glu
    1565                1570                1575

Val Glu Met Asp His Tyr Arg Glu Pro Phe Leu Asn Pro Val Asp
    1580                1585                1590

Arg Glu Pro Leu Trp Arg Phe Pro Asn Glu Leu Pro Ile Ala Gly
    1595                1600                1605

Glu Pro Ala Asn Ile Val Ala Leu Val Glu Glu Tyr Met Asp Trp
    1610                1615                1620

Leu His Gln Ser Pro Val Pro Lys Leu Leu Phe Trp Gly Thr Pro
    1625                1630                1635

Gly Val Leu Ile Pro Pro Ala Glu Ala Ala Arg Leu Ala Lys Ser
    1640                1645                1650

Leu Pro Asn Cys Lys Ala Val Asp Ile Gly Pro Gly Leu Asn Leu
    1655                1660                1665

Leu Gln Glu Asp Asn Pro Asp Leu Ile Gly Ser Glu Ile Ala Arg
    1670                1675                1680

Trp Leu Ser Thr Leu Glu Ile Ser Gly Lys Arg Pro Ala Ala Thr
    1685                1690                1695

Lys Lys Ala Gly Gln Ala Lys Lys Lys Lys
    1700                1705
```

<210> SEQ ID NO 5
<211> LENGTH: 30
<212> TYPE: DNA
<213> ORGANISM: Artificial Sequence
<220> FEATURE:
<223> OTHER INFORMATION: Synthetic

<400> SEQUENCE: 5
tttcttgcca tattccacgt cctacagtgg     30

<210> SEQ ID NO 6
<211> LENGTH: 30
<212> TYPE: DNA
<213> ORGANISM: Artificial Sequence
<220> FEATURE:
<223> OTHER INFORMATION: Synthetic

<400> SEQUENCE: 6
ttagggttag ggttagggtt agggttaggg     30

<210> SEQ ID NO 7
<211> LENGTH: 27
<212> TYPE: DNA
<213> ORGANISM: Artificial Sequence
<220> FEATURE:
<223> OTHER INFORMATION: Synthetic

<400> SEQUENCE: 7
actcatctaa tatgttctac agtgtgg     27

<210> SEQ ID NO 8
<211> LENGTH: 106
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: n is a, c, g, or t

<400> SEQUENCE: 8
taatacgact cactataggn gtttaagagc tatgctggaa acagcatagc aagtttaaat     60
aaggctagtc cgttatcaac ttgaaaaagt ggcaccgagt cggtgc     106

<210> SEQ ID NO 9
<211> LENGTH: 36
<212> TYPE: RNA
<213> ORGANISM: Artificial Sequence
<220> FEATURE:
<223> OTHER INFORMATION: Synthetic

<400> SEQUENCE: 9
ccauauucca cguccuacag guuuaagagc uaugcu     36

<210> SEQ ID NO 10
<211> LENGTH: 77
<212> TYPE: RNA
<213> ORGANISM: Artificial Sequence
<220> FEATURE:
<223> OTHER INFORMATION: Synthetic

<400> SEQUENCE: 10
ggaaacagca uagcaaguuu aaauaaggcu aguccguuau caacuugaaa aaguggcacc     60
gagucggugc uuuuuuu     77

<210> SEQ ID NO 11
<211> LENGTH: 40
<212> TYPE: DNA
<213> ORGANISM: Artificial Sequence
<220> FEATURE:
<223> OTHER INFORMATION: Synthetic

<400> SEQUENCE: 11
aaacttgcta tgctgtttcc agcatagctc ttaaacctgt                    40

<210> SEQ ID NO 12
<211> LENGTH: 154
<212> TYPE: DNA
<213> ORGANISM: Artificial Sequence
<220> FEATURE:
<223> OTHER INFORMATION: Synthetic

<400> SEQUENCE: 12
ggtgacacta tagaactcga gcagctggat cctaatacga ctcactatag gccatattcc    60
acgtacaggt ttaagagcta tgctggaaac agcatagcaa gtttaaataa ggctagtccg   120
ttatcaactt gaaaaagtgg caccgagtcg gtgc                              154

<210> SEQ ID NO 13
<211> LENGTH: 159
<212> TYPE: DNA
<213> ORGANISM: Artificial Sequence
<220> FEATURE:
<223> OTHER INFORMATION: Synthetic

<400> SEQUENCE: 13
ggtgacacta tagaactcga gcagctggat cctaatacga ctcactatag ggttagggtt    60
agggttaggg ttagtttaag agctatgctg gaaacagcat agcaagttta ataaggcta   120 gtccgttatc aacttgaaaa agtggcaccg agtcggtgc                          159

<210> SEQ ID NO 14
<211> LENGTH: 157
<212> TYPE: DNA
<213> ORGANISM: Artificial Sequence
<220> FEATURE:
<223> OTHER INFORMATION: Synthetic

<400> SEQUENCE: 14
ggtgacacta tagaactcga gcagctggat cctaatacga ctcactatag gatctattat    60
gttctacagt ggtttaagag ctatgctgga aacagcatag caagtttaaa taaggctagt   120
ccgttatcaa cttgaaaaag tggcaccgag tcggtgc                            157

<210> SEQ ID NO 15
<211> LENGTH: 155
<212> TYPE: DNA
<213> ORGANISM: Artificial Sequence
<220> FEATURE:
<223> OTHER INFORMATION: Synthetic

<400> SEQUENCE: 15
ggtgacacta tagaactcga gcagctggat cctaatacga ctcactatag gtcgactcta    60
gaaaacatgg tttaagagct atgctggaaa cagcatagca agtttaaata aggctagtcc   120
gttatcaact tgaaaagtg gcaccgagtc ggtgc                               155

<210> SEQ ID NO 16

```
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: n is a, c, g, or t

<400> SEQUENCE: 16
taatacgact cactataggn gtttaagagc tatgctgg                              38

<210> SEQ ID NO 17
<211> LENGTH: 37
<212> TYPE: DNA
<213> ORGANISM: Artificial Sequence
<220> FEATURE:
<223> OTHER INFORMATION: Synthetic

<400> SEQUENCE: 17
taatacgact cactataggg tttaagagct atgctgg                               37

<210> SEQ ID NO 18
<211> LENGTH: 58
<212> TYPE: DNA
<213> ORGANISM: Artificial Sequence
<220> FEATURE:
<223> OTHER INFORMATION: Synthetic

<400> SEQUENCE: 18
taatacgact cactatagga ggtgacaccg tgggctgggg gtttaagagc tatgctgg        58

<210> SEQ ID NO 19
<211> LENGTH: 54
<212> TYPE: DNA
<213> ORGANISM: Artificial Sequence
<220> FEATURE:
<223> OTHER INFORMATION: Synthetic

<400> SEQUENCE: 19
taatacgact cactatagga agtgtcgaca ggaagagttt aagagctatg ctgg            54

<210> SEQ ID NO 20
<211> LENGTH: 59
<212> TYPE: DNA
<213> ORGANISM: Artificial Sequence
<220> FEATURE:
<223> OTHER INFORMATION: Synthetic

<400> SEQUENCE: 20
taatacgact cactatagga aggtatgggt gtggaaggta tgtttaagag ctatgctgg       59

<210> SEQ ID NO 21
<211> LENGTH: 58
<212> TYPE: DNA
<213> ORGANISM: Artificial Sequence
<220> FEATURE:
<223> OTHER INFORMATION: Synthetic

<400> SEQUENCE: 21
taatacgact cactatagga agagtggagg ccgtgcgcgg gtttaagagc tatgctgg        58

<210> SEQ ID NO 22
<211> LENGTH: 58
<212> TYPE: DNA
<213> ORGANISM: Artificial Sequence
```

```
<220> FEATURE:
<223> OTHER INFORMATION: Synthetic

<400> SEQUENCE: 22
taatacgact cactatagga cctcaggtga tctcctgcct gtttaagagc tatgctgg      58

<210> SEQ ID NO 23
<211> LENGTH: 54
<212> TYPE: DNA
<213> ORGANISM: Artificial Sequence
<220> FEATURE:
<223> OTHER INFORMATION: Synthetic

<400> SEQUENCE: 23
taatacgact cactataggt atatttagta gagacggttt aagagctatg ctgg      54

<210> SEQ ID NO 24
<211> LENGTH: 57
<212> TYPE: DNA
<213> ORGANISM: Artificial Sequence
<220> FEATURE:
<223> OTHER INFORMATION: Synthetic

<400> SEQUENCE: 24
taatacgact cactatagga gtagctggaa ttacaggtgg tttaagagct atgctgg      57

<210> SEQ ID NO 25
<211> LENGTH: 59
<212> TYPE: DNA
<213> ORGANISM: Artificial Sequence
<220> FEATURE:
<223> OTHER INFORMATION: Synthetic

<400> SEQUENCE: 25
taatacgact cactataggc tcactgcaac ctccacctcc cgtttaagag ctatgctgg      59

<210> SEQ ID NO 26
<211> LENGTH: 59
<212> TYPE: DNA
<213> ORGANISM: Artificial Sequence
<220> FEATURE:
<223> OTHER INFORMATION: Synthetic

<400> SEQUENCE: 26
taatacgact cactatagga cagagtctcg ctctctctcc cgtttaagag ctatgctgg      59

<210> SEQ ID NO 27
<211> LENGTH: 58
<212> TYPE: DNA
<213> ORGANISM: Artificial Sequence
<220> FEATURE:
<223> OTHER INFORMATION: Synthetic

<400> SEQUENCE: 27
taatacgact cactatagga agaggagaaa agtggggaag gtttaagagc tatgctgg      58

<210> SEQ ID NO 28
<211> LENGTH: 59
<212> TYPE: DNA
<213> ORGANISM: Artificial Sequence
<220> FEATURE:
<223> OTHER INFORMATION: Synthetic

<400> SEQUENCE: 28
taatacgact cactatagga acagagggcc agagagcagc cgtttaagag ctatgctgg      59
```

<210> SEQ ID NO 29
<211> LENGTH: 60
<212> TYPE: DNA
<213> ORGANISM: Artificial Sequence
<220> FEATURE:
<223> OTHER INFORMATION: Synthetic

<400> SEQUENCE: 29
taatacgact cactataggt ctttctctct gcgagtaagc ctgtttaaga gctatgctgg    60

<210> SEQ ID NO 30
<211> LENGTH: 58
<212> TYPE: DNA
<213> ORGANISM: Artificial Sequence
<220> FEATURE:
<223> OTHER INFORMATION: Synthetic

<400> SEQUENCE: 30
taatacgact cactataggt acacccttgt gtacagagct gtttaagagc tatgctgg    58

<210> SEQ ID NO 31
<211> LENGTH: 57
<212> TYPE: DNA
<213> ORGANISM: Artificial Sequence
<220> FEATURE:
<223> OTHER INFORMATION: Synthetic

<400> SEQUENCE: 31
taatacgact cactatagga aaactcatgt aaagctgcag tttaagagct atgctgg    57

<210> SEQ ID NO 32
<211> LENGTH: 58
<212> TYPE: DNA
<213> ORGANISM: Artificial Sequence
<220> FEATURE:
<223> OTHER INFORMATION: Synthetic

<400> SEQUENCE: 32
taatacgact cactataggc aagcaaggga agcgacaagg gtttaagagc tatgctgg    58

<210> SEQ ID NO 33
<211> LENGTH: 55
<212> TYPE: DNA
<213> ORGANISM: Artificial Sequence
<220> FEATURE:
<223> OTHER INFORMATION: Synthetic

<400> SEQUENCE: 33
taatacgact cactatagga ggcggccagg gcgcagagtt taagagctat gctgg    55

<210> SEQ ID NO 34
<211> LENGTH: 56
<212> TYPE: DNA
<213> ORGANISM: Artificial Sequence
<220> FEATURE:
<223> OTHER INFORMATION: Synthetic

<400> SEQUENCE: 34
taatacgact cactataggc ttttaaaccc gagctcaggt ttaagagcta tgctgg    56

<210> SEQ ID NO 35
<211> LENGTH: 56
<212> TYPE: DNA
<213> ORGANISM: Artificial Sequence
<220> FEATURE:
<223> OTHER INFORMATION: Synthetic

<400> SEQUENCE: 35
taatacgact cactataggt agccccggca ttggccttgt ttaagagcta tgctgg    56

<210> SEQ ID NO 36
<211> LENGTH: 57
<212> TYPE: DNA
<213> ORGANISM: Artificial Sequence
<220> FEATURE:
<223> OTHER INFORMATION: Synthetic

<400> SEQUENCE: 36
taatacgact cactataggc ctgtgggaga tgttccctcg tttaagagct atgctgg    57

<210> SEQ ID NO 37
<211> LENGTH: 59
<212> TYPE: DNA
<213> ORGANISM: Artificial Sequence
<220> FEATURE:
<223> OTHER INFORMATION: Synthetic

<400> SEQUENCE: 37
taatacgact cactataggt cctgaagcca gagggacagc cgtttaagag ctatgctgg    59

<210> SEQ ID NO 38
<211> LENGTH: 56
<212> TYPE: DNA
<213> ORGANISM: Artificial Sequence
<220> FEATURE:
<223> OTHER INFORMATION: Synthetic

<400> SEQUENCE: 38
taatacgact cactatagga gtctttgggg gagagtctgt ttaagagcta tgctgg    56

<210> SEQ ID NO 39
<211> LENGTH: 57
<212> TYPE: DNA
<213> ORGANISM: Artificial Sequence
<220> FEATURE:
<223> OTHER INFORMATION: Synthetic

<400> SEQUENCE: 39
taatacgact cactataggc tcctgccctg cctctcagcg tttaagagct atgctgg    57

<210> SEQ ID NO 40
<211> LENGTH: 56
<212> TYPE: DNA
<213> ORGANISM: Artificial Sequence
<220> FEATURE:
<223> OTHER INFORMATION: Synthetic

<400> SEQUENCE: 40
taatacgact cactataggc atatttgagg agcttcctgt ttaagagcta tgctgg    56

<210> SEQ ID NO 41
<211> LENGTH: 55
<212> TYPE: DNA
<213> ORGANISM: Artificial Sequence
<220> FEATURE:
<223> OTHER INFORMATION: Synthetic

<400> SEQUENCE: 41
taatacgact cactataggc tgcaagagaa gccatgcgtt taagagctat gctgg    55

<210> SEQ ID NO 42

<210> SEQ ID NO 43
<211> LENGTH: 57
<212> TYPE: DNA
<213> ORGANISM: Artificial Sequence
<220> FEATURE:
<223> OTHER INFORMATION: Synthetic

<400> SEQUENCE: 42
taatacgact cactatagga tgtttcagga ctaggctgag tttaagagct atgctgg        57

<210> SEQ ID NO 43
<211> LENGTH: 57
<212> TYPE: DNA
<213> ORGANISM: Artificial Sequence
<220> FEATURE:
<223> OTHER INFORMATION: Synthetic

<400> SEQUENCE: 43
taatacgact cactataggc tggagggtgg ggaggtgtag tttaagagct atgctgg        57

<210> SEQ ID NO 44
<211> LENGTH: 55
<212> TYPE: DNA
<213> ORGANISM: Artificial Sequence
<220> FEATURE:
<223> OTHER INFORMATION: Synthetic

<400> SEQUENCE: 44
taatacgact cactataggt gggatgagca ctggagcgtt taagagctat gctgg          55

<210> SEQ ID NO 45
<211> LENGTH: 55
<212> TYPE: DNA
<213> ORGANISM: Artificial Sequence
<220> FEATURE:
<223> OTHER INFORMATION: Synthetic

<400> SEQUENCE: 45
taatacgact cactataggc cctgcagatg tggttgagtt taagagctat gctgg          55

<210> SEQ ID NO 46
<211> LENGTH: 57
<212> TYPE: DNA
<213> ORGANISM: Artificial Sequence
<220> FEATURE:
<223> OTHER INFORMATION: Synthetic

<400> SEQUENCE: 46
taatacgact cactatagga ggctggggct tggggcgccg tttaagagct atgctgg        57

<210> SEQ ID NO 47
<211> LENGTH: 56
<212> TYPE: DNA
<213> ORGANISM: Artificial Sequence
<220> FEATURE:
<223> OTHER INFORMATION: Synthetic

<400> SEQUENCE: 47
taatacgact cactataggt ctttgccgtg aactgttcgt ttaagagcta tgctgg         56

<210> SEQ ID NO 48
<211> LENGTH: 58
<212> TYPE: DNA
<213> ORGANISM: Artificial Sequence
<220> FEATURE:
<223> OTHER INFORMATION: Synthetic

<400> SEQUENCE: 48
taatacgact cactatagga ccggggccct ggggagacac gtttaagagc tatgctgg    58

<210> SEQ ID NO 49
<211> LENGTH: 56
<212> TYPE: DNA
<213> ORGANISM: Artificial Sequence
<220> FEATURE:
<223> OTHER INFORMATION: Synthetic

<400> SEQUENCE: 49
taatacgact cactataggc tggacactca gctccatggt ttaagagcta tgctgg    56

<210> SEQ ID NO 50
<211> LENGTH: 57
<212> TYPE: DNA
<213> ORGANISM: Artificial Sequence
<220> FEATURE:
<223> OTHER INFORMATION: Synthetic

<400> SEQUENCE: 50
taatacgact cactatagga gcgcagaggg gcaagacctg tttaagagct atgctgg    57

<210> SEQ ID NO 51
<211> LENGTH: 56
<212> TYPE: DNA
<213> ORGANISM: Artificial Sequence
<220> FEATURE:
<223> OTHER INFORMATION: Synthetic

<400> SEQUENCE: 51
taatacgact cactatagga gaaggagtga aggactgtgt ttaagagcta tgctgg    56

<210> SEQ ID NO 52
<211> LENGTH: 61
<212> TYPE: DNA
<213> ORGANISM: Artificial Sequence
<220> FEATURE:
<223> OTHER INFORMATION: Synthetic

<400> SEQUENCE: 52
taatacgact cactataggc tccacgacat gcctagcttc ttcgtttaag agctatgctg    60
g    61

<210> SEQ ID NO 53
<211> LENGTH: 57
<212> TYPE: DNA
<213> ORGANISM: Artificial Sequence
<220> FEATURE:
<223> OTHER INFORMATION: Synthetic

<400> SEQUENCE: 53
taatacgact cactatagga gctgggccag gagaggagag tttaagagct atgctgg    57

<210> SEQ ID NO 54
<211> LENGTH: 57
<212> TYPE: DNA
<213> ORGANISM: Artificial Sequence
<220> FEATURE:
<223> OTHER INFORMATION: Synthetic

<400> SEQUENCE: 54
taatacgact cactatagga ccgggcatga ccagggcctg tttaagagct atgctgg    57

<210> SEQ ID NO 55

<211> LENGTH: 55
<212> TYPE: DNA
<213> ORGANISM: Artificial Sequence
<220> FEATURE:
<223> OTHER INFORMATION: Synthetic

<400> SEQUENCE: 55
taatacgact cactataggg cagcccccac ccccacagtt taagagctat gctgg    55

<210> SEQ ID NO 56
<211> LENGTH: 57
<212> TYPE: DNA
<213> ORGANISM: Artificial Sequence
<220> FEATURE:
<223> OTHER INFORMATION: Synthetic

<400> SEQUENCE: 56
taatacgact cactataggt tcctttggc tccctgaagg tttaagagct atgctgg    57

<210> SEQ ID NO 57
<211> LENGTH: 55
<212> TYPE: DNA
<213> ORGANISM: Artificial Sequence
<220> FEATURE:
<223> OTHER INFORMATION: Synthetic

<400> SEQUENCE: 57
taatacgact cactataggg tctgtttgca cacttgcgtt taagagctat gctgg    55

<210> SEQ ID NO 58
<211> LENGTH: 59
<212> TYPE: DNA
<213> ORGANISM: Artificial Sequence
<220> FEATURE:
<223> OTHER INFORMATION: Synthetic

<400> SEQUENCE: 58
taatacgact cactataggc ccaggccaga ggaaaaacac agtttaagag ctatgctgg    59

<210> SEQ ID NO 59
<211> LENGTH: 56
<212> TYPE: DNA
<213> ORGANISM: Artificial Sequence
<220> FEATURE:
<223> OTHER INFORMATION: Synthetic

<400> SEQUENCE: 59
taatacgact cactataggt ttccttaagg aacagcccgt ttaagagcta tgctgg    56

<210> SEQ ID NO 60
<211> LENGTH: 58
<212> TYPE: DNA
<213> ORGANISM: Artificial Sequence
<220> FEATURE:
<223> OTHER INFORMATION: Synthetic

<400> SEQUENCE: 60
taatacgact cactataggc agacagaggt gggctagaca gtttaagagc tatgctgg    58

<210> SEQ ID NO 61
<211> LENGTH: 59
<212> TYPE: DNA
<213> ORGANISM: Artificial Sequence
<220> FEATURE:
<223> OTHER INFORMATION: Synthetic

<400> SEQUENCE: 61

```
taatacgact cactataggc cccaggcagg aatgactcag agtttaagag ctatgctgg      59
```

<210> SEQ ID NO 62
<211> LENGTH: 56
<212> TYPE: DNA
<213> ORGANISM: Artificial Sequence
<220> FEATURE:
<223> OTHER INFORMATION: Synthetic

<400> SEQUENCE: 62

```
taatacgact cactatagga cccagttgcc tttccctggt ttaagagcta tgctgg         56
```

<210> SEQ ID NO 63
<211> LENGTH: 57
<212> TYPE: DNA
<213> ORGANISM: Artificial Sequence
<220> FEATURE:
<223> OTHER INFORMATION: Synthetic

<400> SEQUENCE: 63

```
taatacgact cactatagga ccccagggag gtgacaggcg tttaagagct atgctgg        57
```

<210> SEQ ID NO 64
<211> LENGTH: 59
<212> TYPE: DNA
<213> ORGANISM: Artificial Sequence
<220> FEATURE:
<223> OTHER INFORMATION: Synthetic

<400> SEQUENCE: 64

```
taatacgact cactataggc cacagcgcac tccacgggga agtttaagag ctatgctgg      59
```

<210> SEQ ID NO 65
<211> LENGTH: 58
<212> TYPE: DNA
<213> ORGANISM: Artificial Sequence
<220> FEATURE:
<223> OTHER INFORMATION: Synthetic

<400> SEQUENCE: 65

```
taatacgact cactataggt cccagactga cagatagacc gtttaagagc tatgctgg       58
```

<210> SEQ ID NO 66
<211> LENGTH: 56
<212> TYPE: DNA
<213> ORGANISM: Artificial Sequence
<220> FEATURE:
<223> OTHER INFORMATION: Synthetic

<400> SEQUENCE: 66

```
taatacgact cactatagga ggggtctgtg gagagtttgt ttaagagcta tgctgg         56
```

<210> SEQ ID NO 67
<211> LENGTH: 57
<212> TYPE: DNA
<213> ORGANISM: Artificial Sequence
<220> FEATURE:
<223> OTHER INFORMATION: Synthetic

<400> SEQUENCE: 67

```
taatacgact cactataggt ccagcatcag cgacgccctg tttaagagct atgctgg        57
```

<210> SEQ ID NO 68
<211> LENGTH: 57
<212> TYPE: DNA

<210> SEQ ID NO 68
<211> LENGTH: 57
<212> TYPE: DNA
<213> ORGANISM: Artificial Sequence
<220> FEATURE:
<223> OTHER INFORMATION: Synthetic

<400> SEQUENCE: 68
taatacgact cactataggc ctaagactcc agagccaaag tttaagagct atgctgg       57

<210> SEQ ID NO 69
<211> LENGTH: 58
<212> TYPE: DNA
<213> ORGANISM: Artificial Sequence
<220> FEATURE:
<223> OTHER INFORMATION: Synthetic

<400> SEQUENCE: 69
taatacgact cactataggc tactacgtag ggttgtcatg gtttaagagc tatgctgg      58

<210> SEQ ID NO 70
<211> LENGTH: 57
<212> TYPE: DNA
<213> ORGANISM: Artificial Sequence
<220> FEATURE:
<223> OTHER INFORMATION: Synthetic

<400> SEQUENCE: 70
taatacgact cactataggt aaagtagaaa aggcataaag tttaagagct atgctgg       57

<210> SEQ ID NO 71
<211> LENGTH: 56
<212> TYPE: DNA
<213> ORGANISM: Artificial Sequence
<220> FEATURE:
<223> OTHER INFORMATION: Synthetic

<400> SEQUENCE: 71
taatacgact cactataggc acttttggag gcccaggcgt ttaagagcta tgctgg        56

<210> SEQ ID NO 72
<211> LENGTH: 58
<212> TYPE: DNA
<213> ORGANISM: Artificial Sequence
<220> FEATURE:
<223> OTHER INFORMATION: Synthetic

<400> SEQUENCE: 72
taatacgact cactataggt ggagacaggg ttggccaagc gtttaagagc tatgctgg      58

<210> SEQ ID NO 73
<211> LENGTH: 59
<212> TYPE: DNA
<213> ORGANISM: Artificial Sequence
<220> FEATURE:
<223> OTHER INFORMATION: Synthetic

<400> SEQUENCE: 73
taatacgact cactataggc tccctgcaac ctctgcctcc cgtttaagag ctatgctgg     59

<210> SEQ ID NO 74
<211> LENGTH: 59
<212> TYPE: DNA
<213> ORGANISM: Artificial Sequence
<220> FEATURE:
<223> OTHER INFORMATION: Synthetic

<400> SEQUENCE: 74
taatacgact cactataggc ctctttctca aacacgtctt tagtttaaga gctatgctg     59

<210> SEQ ID NO 75
<211> LENGTH: 58
<212> TYPE: DNA
<213> ORGANISM: Artificial Sequence
<220> FEATURE:
<223> OTHER INFORMATION: Synthetic

<400> SEQUENCE: 75
taatacgact cactatagga acccggaatg gcacttgtgt gtttaagagc tatgctgg       58

<210> SEQ ID NO 76
<211> LENGTH: 55
<212> TYPE: DNA
<213> ORGANISM: Artificial Sequence
<220> FEATURE:
<223> OTHER INFORMATION: Synthetic

<400> SEQUENCE: 76
taatacgact cactataggt ggcttttag aggcacggtt taagagctat gctgg            55

<210> SEQ ID NO 77
<211> LENGTH: 55
<212> TYPE: DNA
<213> ORGANISM: Artificial Sequence
<220> FEATURE:
<223> OTHER INFORMATION: Synthetic

<400> SEQUENCE: 77
taatacgact cactataggc ttggtgtatt cagaatggtt taagagctat gctgg           55

<210> SEQ ID NO 78
<211> LENGTH: 59
<212> TYPE: DNA
<213> ORGANISM: Artificial Sequence
<220> FEATURE:
<223> OTHER INFORMATION: Synthetic

<400> SEQUENCE: 78
taatacgact cactataggc actgccaggc cagcctctgc cgtttaagag ctatgctgg       59

<210> SEQ ID NO 79
<211> LENGTH: 58
<212> TYPE: DNA
<213> ORGANISM: Artificial Sequence
<220> FEATURE:
<223> OTHER INFORMATION: Synthetic

<400> SEQUENCE: 79
taatacgact cactataggc taaggacaag aggcaatgag gtttaagagc tatgctgg       58

<210> SEQ ID NO 80
<211> LENGTH: 60
<212> TYPE: DNA
<213> ORGANISM: Artificial Sequence
<220> FEATURE:
<223> OTHER INFORMATION: Synthetic

<400> SEQUENCE: 80
taatacgact cactatagga ctcaatttct cagaacatgc tggtttaaga gctatgctgg     60

<210> SEQ ID NO 81
<211> LENGTH: 59
<212> TYPE: DNA
<213> ORGANISM: Artificial Sequence
<220> FEATURE:

<223> OTHER INFORMATION: Synthetic

<400> SEQUENCE: 81
taatacgact cactatagga cagagtttct ctctgtcccc cgtttaagag ctatgctgg    59

<210> SEQ ID NO 82
<211> LENGTH: 55
<212> TYPE: DNA
<213> ORGANISM: Artificial Sequence
<220> FEATURE:
<223> OTHER INFORMATION: Synthetic

<400> SEQUENCE: 82
taatacgact cactataggg gtttcaccat gttggccgtt taagagctat gctgg    55

<210> SEQ ID NO 83
<211> LENGTH: 59
<212> TYPE: DNA
<213> ORGANISM: Artificial Sequence
<220> FEATURE:
<223> OTHER INFORMATION: Synthetic

<400> SEQUENCE: 83
taatacgact cactataggc tcgcctcggc tcccaaagtg cgtttaagag ctatgctgg    59

<210> SEQ ID NO 84
<211> LENGTH: 55
<212> TYPE: DNA
<213> ORGANISM: Artificial Sequence
<220> FEATURE:
<223> OTHER INFORMATION: Synthetic

<400> SEQUENCE: 84
taatacgact cactataggg catttgtgtt gcacgtggtt taagagctat gctgg    55

<210> SEQ ID NO 85
<211> LENGTH: 57
<212> TYPE: DNA
<213> ORGANISM: Artificial Sequence
<220> FEATURE:
<223> OTHER INFORMATION: Synthetic

<400> SEQUENCE: 85
taatacgact cactatagga gtggagctgc gggcaacccg tttaagagct atgctgg    57

<210> SEQ ID NO 86
<211> LENGTH: 56
<212> TYPE: DNA
<213> ORGANISM: Artificial Sequence
<220> FEATURE:
<223> OTHER INFORMATION: Synthetic

<400> SEQUENCE: 86
taatacgact cactataggt agagatgccg ccccgcccgt ttaagagcta tgctgg    56

<210> SEQ ID NO 87
<211> LENGTH: 58
<212> TYPE: DNA
<213> ORGANISM: Artificial Sequence
<220> FEATURE:
<223> OTHER INFORMATION: Synthetic

<400> SEQUENCE: 87
taatacgact cactataggt ccagtggcca gtggattttg gtttaagagc tatgctgg    58

```
<210> SEQ ID NO 88
<211> LENGTH: 58
<212> TYPE: DNA
<213> ORGANISM: Artificial Sequence
<220> FEATURE:
<223> OTHER INFORMATION: Synthetic

<400> SEQUENCE: 88
taatacgact cactatagga ggcagctggg actagaaccc gtttaagagc tatgctgg        58

<210> SEQ ID NO 89
<211> LENGTH: 56
<212> TYPE: DNA
<213> ORGANISM: Artificial Sequence
<220> FEATURE:
<223> OTHER INFORMATION: Synthetic

<400> SEQUENCE: 89
taatacgact cactataggt cggtgggctg ggctggttgt ttaagagcta tgctgg          56

<210> SEQ ID NO 90
<211> LENGTH: 57
<212> TYPE: DNA
<213> ORGANISM: Artificial Sequence
<220> FEATURE:
<223> OTHER INFORMATION: Synthetic

<400> SEQUENCE: 90
taatacgact cactatagga atgaatggct gtctcagcag tttaagagct atgctgg         57

<210> SEQ ID NO 91
<211> LENGTH: 59
<212> TYPE: DNA
<213> ORGANISM: Artificial Sequence
<220> FEATURE:
<223> OTHER INFORMATION: Synthetic

<400> SEQUENCE: 91
taatacgact cactatagga aacagacgtg gcccagtctc tgtttaagag ctatgctgg       59

<210> SEQ ID NO 92
<211> LENGTH: 56
<212> TYPE: DNA
<213> ORGANISM: Artificial Sequence
<220> FEATURE:
<223> OTHER INFORMATION: Synthetic

<400> SEQUENCE: 92
taatacgact cactataggc tgagagctgc atttcgaagt ttaagagcta tgctgg          56

<210> SEQ ID NO 93
<211> LENGTH: 59
<212> TYPE: DNA
<213> ORGANISM: Artificial Sequence
<220> FEATURE:
<223> OTHER INFORMATION: Synthetic

<400> SEQUENCE: 93
taatacgact cactatagga caagtcagga agggccctgt ggtttaagag ctatgctgg       59

<210> SEQ ID NO 94
<211> LENGTH: 86
<212> TYPE: DNA
<213> ORGANISM: Artificial Sequence
<220> FEATURE:
<223> OTHER INFORMATION: Synthetic
```

-continued

```
<400> SEQUENCE: 94
gcaccgactc ggtgccactt tttcaagttg ataacggact agccttattt aaacttgcta    60
tgctgtttcc agcatagctc ttaaac                                         86

<210> SEQ ID NO 95
<211> LENGTH: 20
<212> TYPE: DNA
<213> ORGANISM: Artificial Sequence
<220> FEATURE:
<223> OTHER INFORMATION: Synthetic

<400> SEQUENCE: 95
gcaccgactc ggtgccactt                                                20
```

GENOMIC PROBES

RELATED APPLICATIONS

This application is a divisional of U.S. patent application Ser. No. 15/519,781, which is a national phase of International Patent Application No. PCT/US15/56048, filed Oct. 16, 2015, which claims priority from U.S. Provisional Application Ser. No. 62/065,602, filed on Oct. 17, 2014, the entire disclosure of which is incorporated herein by this reference.

TECHNICAL FIELD

The presently-disclosed subject matter relates to genomic probes. In particular, the presently-disclosed subject matter relates to probes that comprise a Cas polypeptide complexed with a gRNA specific for a target nucleic acid sequences, including genomic DNA sequences.

INTRODUCTION

Probes for nucleic acid sequences are used for a variety of purposes. Such probes can be used to identify whether a specific sequence is found on a DNA or RNA sample and to identify the copy numbers of the specific sequence. The specific sequences may be sequences associated with the likelihood of developing certain diseases or conditions, sequences associated with the stage of certain diseases or conditions, sequences from infecting viruses, bacteria and other infection organisms, sequences that encode for certain genes, repetitive sequences, and the like. Such probes can be used to detect the relative location of multiple sequences, for instance, the genetic translocations that are frequently detected in various cancers. Probing the DNA of a cell can therefore provide valuable information that can be used for prognostic, diagnostic, medical, and species identification purposes.

The type II clustered regularly interspaced short palindromic repeats (CRISPR)-CRISPR-associated caspase 9 (Cas9) system derived from *Streptococcus pyogenes* has become a revolutionary tool for targeted genome editing, and its nuclease-deficient derivatives (dCas9) also are used for control of gene expression and visualization of genomic loci in live cells through fusion with a transcription-regulation domain or a fluorescent protein, respectively. Inherent multiplexing features offered by the CRISPR system hold great promise for applications in high-throughput assays. By programming the gRNA sequences, Cas9 protein can be directed to any target DNA sequence of interest. However, using genetically coded Cas9 protein and gRNA for imaging genomic DNA in live cell is still greatly limited because of the lack of efficient transduction of tens to hundreds of gRNAs in one cell, and because that assembly of Cas9 and gRNA in live cells are dependent on random collision, and because that one type of Cas protein can only be labeled with one color for imaging one group of target DNA sequence. Moreover, genetically coded expression of Cas9 and gRNA requires delivery of genetic material to cultured live cells, which is not generally applicable to primary cells and tissues.

Fluorescent in situ hybridization (FISH) is currently used to identify specific DNA or RNA sequences in fixed cells and tissues. FISH typically uses a formamide chemistry and heat treatment for DNA denaturation. FISH includes steps for sample denaturation, hybridization, and post-hybridization washes, which require takes hours to days. (Lawrence J B, Villnave C A, Singer R H. Cell. 1988 Jan. 15; 52(1): 51-61. PMID: 2830981; Lawrence J B, Singer R H. Nucleic Acids Res. 1985 Mar. 11; 13(5):1777-99. PMID: 3889842; Cremer T. Landegent J. Brueckner A, Scholl H P, Schardin M, Hager H D, Devilee P. Pearson P. van der Ploeg M. (1986), "Detection of chromosome aberrations in the human interphase nucleus by visualization of specific target DNAs with radioactive and non-radioactive in situ hybridization techniques: diagnosis of trisomy 18 with probe L 0.84," Hum. Genet 74:346-352; Pinkel D, Straume T. Gray J W. (1986) "Cytogenetic analysis using quantitative, high-sensitivity, fluorescence hybridization," Proc Natl Acad Sci USA 83:2934-2938).

Despite continuous improvements, DNA FISH requires harsh treatments such as heat and formamide to denature dsDNA to allow probe hybridization, thus running the risk of affecting the integrity of the biological structure and genome organization. In cells, genomic DNA is highly folded and organized in three dimensions. The spatial organization of chromatin in the nucleus and the relative positions of distinct chromatin regions are tightly associated with gene regulation in normal development and disease. While it can be beneficial to study interphase genomic organization with DNA that is in its native state, the study of organization of chromatin is not possible with FISH methods that denature the native chromosomes.

DNA FISH also is limited in detection resolution with BAC probes and by the high cost of oligo probes. Current FISH protocols require denaturation of samples and fluorescent labeling of all individual DNA probes, which adds to the complexity and cost of current FISH imaging methods. The lengthy procedure of DNA FISH also hinders its wide use in research and clinics.

Hence, there remains a need for compositions and methods for imaging nucleic acid sequences, including DNA, that do not require denaturation of a sample, including compositions and methods for imaging genomic DNA in its native state. There also remains a need for imaging probes and methods that can operate rapidly and do not require lengthy and harsh treatment of a sample.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Provided herein is a technology for the detection of nucleic acid sequences within undisturbed nuclei of fixed cells and tissues. The detection targets can be DNA, RNA, and other nucleic acid analogues or modified nucleic acid. In one exemplary embodiment, a protein from bacterial CRISPR (clustered regularly interspaced short palindromic repeats) system, is combined with an RNA sequence as probes to find the genes of interest in the intact genome. This approach preserves the spatial relationships of the genetic elements, which are important for understanding gene expression and detecting genetic translocations; moreover, the process is remarkably rapid (15 min), convenient, and can be used directly on tissues for diagnosis of disease.

The presently disclosed subject matter includes a probe. The probe includes a Cas (CRISPR associated caspase) polypeptide, or fragments and/or variants of a Cas polypeptide, a guide RNA (gRNA) specific for a predetermined nucleic acid sequence that is conjugated to the Cas polypeptide; and a label that is bound to the Cas polypeptide, the gRNA, or both.

In some embodiments, the Cas polypeptide is bound or fused to the label. The label in some instances can be fluorescent proteins, fluorescent labels, dyes, quantum dots, gold particles, radioactive labels, chemiluminescent enzymes, or enzymes that modify a substrate to make it visible by microscopy, or other analytes for microscopy or other detection methods.

The Cas polypeptide in some preferred embodiments includes a Cas9 polypeptide, or a fragment or variant of a Cas9 polypeptide. In some embodiments, the Cas9 polypeptide includes a nuclease-deficient dmCas9 polypeptide, fragment, and/or variant. When the Cas9 polypeptide is a dmCas9 polypeptide, in some embodiments, the dmCas9 polypeptide is encoded by a nucleotide sequence of SEQ ID NO: 1 or the dmCas9 polypeptide has a sequence of SEQ ID NO: 2. The Cas polypeptide in some embodiments include other CRISPR associated proteins in CRISPR I, II, II systems, as will be recognized by one of ordinary skill in the art.

In some instances, the probe includes no nuclease activity. In other instances, the probe can include little nuclease activity, diminished nuclease activity, or full, wild type nuclease activity.

In some embodiments, the polypeptide includes a nuclear localization signal (NLS). A NLS can assist the polypeptide in being incorporated by the nucleus of a cell. One example of a polypeptide that includes a NLS is encoded by a nucleotide sequence of SEQ ID NO: 3, or the polypeptide has a sequence of SEQ ID NO: 4.

In some embodiments, the gRNA is bound or fused to the label. The label in some instances can be fluorescent labels, dyes, quantum dots, gold particles, radioactive labels, RNA aptamers that can be directly or indirectly labeled, enzymes or other analytes for microscopy or other detection methods.

In some embodiments, the probe includes a gRNA that contains a constant backbone sequence and a variable sequence that is specific for a predetermined nucleic acid that is DNA or RNA. The gRNA typically comprises a target section, wherein the target section has full or partial complementarity to the predetermined nucleic acid sequence. In some embodiments, the target section of the gRNA is about 15 to about 25 nucleotides in length.

The backbone sequence of gRNA contains a hairpin structure for interacting with Cas protein. In some instances, the length and nucleic acid composition of the gRNA backbone can be modified to have longer or shorter, more dynamic or more stable hairpin structure. In other instances, gRNA can be modified for other specific properties.

In some instances, the gRNA can be substituted by two or more RNA molecules that can form interactions and remain functional in binding to Cas protein and hybridizing to a nuclei acid substrate.

In some embodiments, detection of target nucleic acid is from the labels on the Cas protein or gRNA. In some instances, a secondary reaction that relies on the binding or nuclease activity of Cas/gRNA complex on DNA can generate signal for detection.

Also disclosed herein are methods for imaging nucleic acids, including a first step of providing a sample that includes a nucleic acid; a second step of contacting the sample with a probe of any of the embodiments disclosed herein, and a subsequent step of detecting whether the probe binds the nucleic acid. The binding of the probe to the nucleic acid indicates the presence of a predetermined nucleic acid sequence in the nucleic acid sample.

In some instances, the sample is selected from chromosome spreads for genetic testing, cultures, prenatal materials, samples for in vitro fertilization, swabs, air filters, water cooling towers, food, drink, hair, stool, urine, saliva, blood, lymph, sputum, cervical smears, sperm, sections of tissues from biopsies, sections of tissues from autopsies, and combinations thereof. Any source of genetic material is contemplated for use in the presently disclosed subject matter. Human, animal, plant, bacteria, fungi and other microorganisms are some examples of sources of genetic material. The samples can be non-treated, or treated by non-crosslinking fixatives, such as methanol, ethanol, acetone, acetic acid or others, or crosslinking fixatives, such as formaldehyde, paraformaldehyde, formalin or others, or other chemicals.

In embodiments where the sample includes live cells, the contacting step can be performed by a method selected from bead loading, microinjection, nanoparticle or lipid mediated transduction, and combinations thereof.

The present methods can include contacting the sample with two or more probes each having different labels and each being selective for different predetermined nucleic acid sequences. These methods allow for detection of multiple nucleic acid sequences.

The predetermined nucleic acid sequence can, in some embodiments, be associated with a disease or condition or a relatively increased likelihood of developing the disease or condition, and the methods disclosed herein can include diagnosing or prognosing a subject with the disease or condition if the predetermined nucleic acid sequence is detected in a nucleic acid sample from the subject.

Kits are also disclosed herein. Kits can include a probe including a Cas polypeptide, or fragments and/or variants thereof a gRNA specific for a predetermined nucleic acid sequence that is capable of being conjugated to a the Cas polypeptide; and a label capable of being bound to the Cas polypeptide, or the gRNA, or both. In some embodiments, the label is bound to the Cas polypeptide. In some embodiments, the Cas9 polypeptide includes a dmCas9 polypeptide, or fragments and/or variants thereof. The kit can include two or more probes each having different labels and each being selective for different predetermined nucleic acid sequences. The gRNAs and probes can be adjusted according to the needs of the researcher, including, for example, the imaging desired, the predetermined nucleic acid sequences, as well as the type of samples on which the probes are to be used (e.g. tissue samples, fixed samples, unfixed samples).

BRIEF DESCRIPTION OF THE DRAWINGS

FIG. 4 includes images and data based on CASFISH in MBS binding sites of MEF cell lines (A) CASFISH against MS2-binding sites (MBS) in a U2OS cell line that contains a repetitive MBS array. All examined cells were labeled as shown in the representative views. Maximum projection of z-stacks is indicated by scale bars. (B) A representative cytogenetic analysis performed on G-banded metaphase of the MEF cell line used in this study. (C) Composite metaphase karyotypes of 10 MEF cells. The MEF cell line has a variable chromosome composition among cells with an average of 94.5.

DESCRIPTION OF EXEMPLARY EMBODIMENTS

Figure 1A:
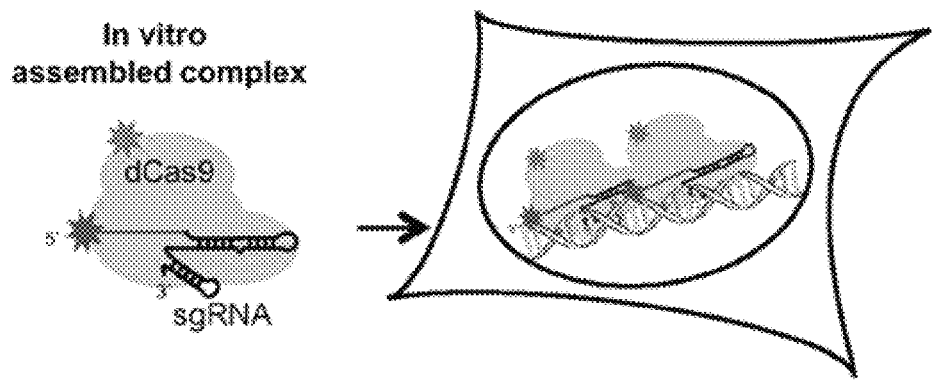
FIG. 1 includes schematics of CASFISH against pericentromeres, telomeres, and centromeres and images of in vitro assembled dCas9/sgRNA fluorescently labels in genomic DNA in cells. (A) Schematic of the CASFISH strategy. (B, Upper) Relative positions of indicated DNA elements on a murine chromosome. (B, Lower) sgRNA sequences as indicated. sgMaj Sat: TTTCTTGCCATATTCCACGTCCTA- CAGTGG (SEQ ID NO: 5); sg Telomere: TTAGGGT-TAGGGTTAGGGTTAGGGTTAGGG (SEQ ID NO:6); sg MinSat: ACTCATCTAATATGTTCTACAGTGTGG (SEQ ID NO: 7). (C) CASFISH against pericentromeres in MEFs using the indicated fluorescent dCas9/sgMaj Sat probe assembled in vitro. dCas9 was labeled by JF646, and sgMaj Sat was labeled with DY547. Fluorescent images were taken with indicated filter settings and are pseudocolored for visualization purposes. (D, Left) CASFISH against telomeres in MEFs using the indicated fluorescent dCas9/sgTelomere complex. (D, Right) Histogram of the number of detected telomeres per cell; n=134 cells. (E) CASFISH in MEF cells against minor satellite elements in centromeres. Maximum projection of z-stacks is shown. (Scale bars, 5 μM.)

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes probes, kits, and methods useful for detecting nucleic acid sequences. Embodiments of the presently-disclosed subject matter can operate with or without requiring denaturation and/or fixation of a sample, and in some embodiments the probes can detect genomic DNA sequences. In this regard, because some embodiments of the presently-disclosed probes do not require denaturation of a sample, imaging methods that utilize the present probes can exclude time-consuming and sample-destroying denaturation steps that are commonly associated with other known imaging techniques. This, in turn, can enhance the rapidity with which the present probes can image nucleic acid sequences, which can be particularly advantageous for processes that are time sensitive, such as certain diagnostic, treatment, or screening processes.

Provided herein is use of in vitro synthesized Cas protein and gRNA molecules followed by in vitro assembly as a programmable and sequence-dependent probe for visualizing genomic DNA in situ. The disclosed in vitro synthesis and in vitro assembly method allow efficient and effective assembly of Cas9 protein, containing any given modification for detection, with any given gRNA and with any given number of gRNAs. All assembled Cas/gRNA complex can be applied at once to its target DNA. Our and others' in vitro studies of the CRISPR system have indicated that Cas9/sgRNA had a strong and stable affinity for its target DNA. Also disclosed herein is a method for imaging multiple target DNA elements with multiple colors, by either applying multiple probes labeled with different colors at once to cells or applying multiple rounds of probe reactions with washing steps in between. These methods allow for multi-colored and expansive labeling of genomic sequences in cells and tissues.

Provided herein is use of a Cas/gRNA binary complex as a highly specific and efficient enzymatic probe for labeling nucleic acids, such as DNA, without global denaturation, which is generated by heat or chemical treatments in DNA FISH protocols. Also disclosed herein is a method of exploiting a CRISPR/Cas system for nucleic acid FISH studies, which allow for multicolored and expansive labeling of genomic sequences in cells and tissues.

The presently-disclosed subject matter includes a probe which comprises a Cas polypeptide, a gRNA that is complexed with the Cas polypeptide. The gRNA is specific for a target nucleic acid sequence of interest. The selected gRNA and Cas polypeptide of certain embodiments of the probes disclosed herein are assembled together before applied to a sample. In some instance, Cas polypeptide and gRNA can be applied simultaneously, or in subsequent order, to a sample. The probes also include one or more labels bound to the Cas polypeptide, the gRNA, or both.

Embodiments of the probes disclosed herein can be assembled in vitro. Indeed, the complex probes disclosed herein have been found to be stable after assembly in vitro, allowing multiple probes for distinct target nucleic acid sequences to be applied simultaneously to a sample without significant disassembly and/or reassembly of the complex(es) that would result in unintended combinations of labels and target sequences.

The terms "polypeptide", "protein", and "peptide", which are used interchangeably herein, refer to a polymer of the protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, naturally occurring proteins, homologs, orthologs, paralogs, fragments and other equivalents, variants, and analogs of the foregoing. Furthermore, the term "fusion polypeptide" is used herein to generally refer to a polypeptide formed from two or more distinct polypeptides.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus of the reference polypeptide, the carboxy-terminus of the reference polypeptide, at intermediate regions of the reference polypeptide, or a combination thereof. Additionally or alternatively, some embodiments include alternative combinatory deletions. A fragment can also be a "functional fragment," in which case the fragment retains some or all of the activity of the reference polypeptide as described herein. For example, a functional fragment of a particular Cas polypeptide variant retains some or all of the Cas-like activity. In some embodiments, the Cas polypeptide fragment and/or variant has up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 residues removed from its C-terminus and/or N-terminus, relative to wild type. In some embodiments, additional residues may be removed. In some embodiments, part or all residues of identified or unidentified domains of Cas9 protein, such as the N-terminal domain, HNH nuclease domain, RuvC nuclease domain, and PAM binding domain, C-terminal domain, can be removed or substituted or inserted with other residues. In some embodiments, the Cas polypeptide fragment and/or variant further includes deletion of residues useful for nuclease activity, for instance, residues in the HNH and RuvC nuclease domains. In some embodiments, the PAM binding domain can be modified to alter PAM motif that Cas9 can recognize.

The term "variant" refers to an amino acid sequence that is different from the reference polypeptide by one or more amino acids, e.g., one or more amino acid substitutions. In some instances, the variant includes amino acid insertions or provides tagging of the polypeptide that differentiates the variant from the reference polypeptide. These variants can modulate properties of the polypeptide, for example, by modulating its activity or stability. In some embodiments, for example, an insertion could include a nuclear localization signal (NLS), a small epitope tag including but not limited to Flag, HA, Myc, Biotin, and Histidine, and polypeptide including but not limited to Halo, SNAP, CLIP, GFP, YFP, RFP, mCherry, and HRP. In some embodiments, for example, an insertion could be at N-terminal, or C-terminal, or internal, or in combination.

Polypeptide mutants, including polypeptide variants and/or polypeptide fragments, can affect various activities of the polypeptide, including, but not limited to, the enzymatic activity, DNA recognition activity, nuclease activity, and/or the targeting activity of a polypeptide. Some embodiments utilize a probe that includes a Cas9 polypeptide to mediate a DNA-FISH process, and can be referred to as "CASFISH" herein.

Cas polypeptides will be known to those of ordinary skill in the art with examples including, but are not limited to, Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, and orthologous polypeptide in various microorganism species, and fragments and/or variants thereof. Cas polypeptide has many orthologous genes in different species. For instance, Cas9 include but not limited to *Streptococcus pyogenes* Cas9 (spCas9), *Streptococcus thermophilus* Cas9 (St1Cas9), *Staphylococcus aureus* Cas9 (SaCas9), and *Neisseria meningitidis* Cas9 (Nm Cas9). In specific embodiments of the presently-disclosed subject matter, the Cas polypeptide includes *Streptococcus pyogenes* Cas9 (spCas9), and variants and/or fragments thereof.

CRISPR/Cas systems will be known to those skilled in the art and can be used in the probes of the presently-disclosed subject matter, as will become apparent to those skilled in the art upon study of this document. For example, in some embodiments, Type I, Type II, and/or Type II systems could be adapted for use in the present invention.

In some embodiments, the Cas polypeptide is a variant or fragment of a wild type Cas polypeptide. In some embodiments, the Cas polypeptide can be modified to further include an insertion capable of modulating the activity and/or stability of the polypeptide.

Another example of the mutant and/or variant polypeptide is a split version of a Cas polypeptide. For example, a split-Cas polypeptide could include the nuclease lobe and α-helical lobe expressed as separate polypeptides. Another example of the mutant and/or variant polypeptide is a Cas polypeptide that could be engineered to recognize alternative PAM sequences. (reference: Engineered CRISPR-Cas9 nucleases with altered PAM specificities. Nature. 2015 Jul. 23; 523(7561):481-5. doi: 10.1038/nature14592. Epub 2015 Jun. 22.) In other embodiments, two or more Cas polypeptides or its variants can be used, for example, in fusion, to enhance targeting efficiency and/or specificity. In some instance, fusing Cas protein to split fluorescent protein could enhance the specificity since the split fluorescent protein becomes fluorescent only when two adjacent Cas/gRNA simultaneously bind to DNA template. Binding of one Cas/gRNA with half of the fluorescent protein at off-target site would be dark and thus reduce noise. In some instance, an engineered Cas polypeptide and/or gRNA that could sense binding to DNA and trigger fluorescence or other activity, could enhance specificity. For instance, the sensor could be Förster resonance energy transfer (FRET) sensor.

In some embodiments, the Cas polypeptide provided has reduced to no nuclease activity, because nuclease activity could break a double stranded DNA sequence. In other embodiments, the protein can be a wild type protein with full activity. Embodiments where the polypeptide provided has reduced to no nuclease activity provide a probe that primarily functions as a probe for DNA sequences without cutting or altering the sequence of the DNA being imaged. Embodiments of polypeptides with reduced to no nuclease activity can include, for example, dmCas9, which is a Cas9 mutant polypeptide that has, relative to wild type Cas9, reduced to no nuclease activity. For example, SEQ ID NO: 1 provides the nucleic acid sequence of a Halo labeled (tagged) dmCas9 polypeptide. Likewise, SEQ ID NO: 2 provides the protein sequence of SEQ ID NO: 1.

In some embodiments the mutant polypeptide can exhibit modified targeting activity. For instance, in some embodiments the polypeptide is imparted with a nuclear localization signal (NLS) that can assist the polypeptide in being incorporated by the nucleus of a cell. As described herein, embodiments of polypeptides that include a NLS can be incorporated into the nucleus of cell, and in some instances can permit the detection of predetermined genomic DNA sequences in unfixed and/or native samples. For example, SEQ ID NO: 3 provides the nucleic acid sequence of an exemplary Cas9 polypeptide that is Halo tagged and includes the NLS. Likewise, SEQ ID NO: 4 provides the protein sequence of SEQ ID NO: 3.

Embodiments of the probes disclosed herein can also include tags, provided to confer various desired features to the probe, for example, facilitating preparation of the probe, detection of the probe, attachment of labels to the probe, and other desirable features that will be apparent to one of ordinary skill in the art upon study of this document.

In some embodiments, detection of the target nucleic acid is achieved by directly observing the labels on the probe, for example, because of the fluorescence of the probe. In other embodiments, the target nucleic acid is detected from secondary reactions that recognize the activity of the probe, including binding of the probes to the target and/or full or partial nuclease activity of the probe. For example, antibodies against the probe can permit detection. That is, secondary reactions can recognize the activity of the probe, permitting detection. Thus, in some embodiments, the label is not itself detectable until it undergoes one or more reactions following hybridization.

In this regard, a tag can be useful in subsequent secondary labeling. The probe need not be directly labeled, but could instead include a tag, such as a tag comprising an antibody target. Such tag could be used in subsequent secondary labeling, for example, making use of antibodies against the antibody target of the tag, and a secondary labeling reaction can recognize activity of the probe, e.g., probe binding to target and/or full or partial nuclease activity of the probe. As such, in some embodiments, the one or more labels of the probe can be a tag.

Exemplary tags can also include, but are not limited to, a polyhistidine tag, an aldehyde tag, and a HaloTag™ (Promega Corporation, Madison, Wis., USA). Other tags SNAP, CLIP, and numerous fluorescent protein such as GFP, YFP, RFP, TagRFP, tandem tomato and mCherry, and enzyme HRP. Some of these proteins may be phooactivatable or photoswitchable.

In some embodiments, a tag is bound to the Cas polypeptide. In some embodiments the Cas polypeptide is expressed as a fusion protein with the tag. For example, in some embodiments, the Cas polypeptide is expressed as a fusion protein with a HaloTag and/or a polyhistidine tag. In other embodiments, the Cas polypeptide is bound to a particular tag, such as a HaloTag, a polyhistidine tag, and/or an aldehyde tag.

Certain tags are useful for easily labeling the Cas polypeptide with one or more labels. In this regard, although embodiments of the presently-disclosed probes include label-conjugated sgRNA probes, they can be costly. However, making use of labeling the Cas polypeptide using a tag can be efficient and cost effective. The HaloTag is one example, which allow for the Cas polypeptide to be easily labelled with a variety of labels (e.g., fluorescent labels) allowing multiplexing with differently labelled probes. As will be recognized by the skilled artisan, there are various alternatives to the HaloTag, for example, SNAP or CLIP.

As noted herein, embodiments of the presently-disclosed probes can include one or more labels bound to the Cas polypeptide, the gRNA, or both. The probe can be labeled by any means that permit detection of the probe within a sample. Thus, a label is any compound or element that permits detection of the probe within a sample, directly or indirectly, including by subsequent secondary labeling.

Examples of labels that can be used in the presently-disclosed probes include, but are not limited to fluorescent labels and fluorophores (e.g. cyanine dyes (Cy dyes), Alexas Fluor dye series, Quasar dyes), dyes, quantum dots, gold particles, radioactive labels, magnetic particles, enzymes, catalysts, spectrophotometric labels, and other analytes for microscopy or other detection methods, such as MRI, CAT or PET. Additional non-limiting examples include Alexa 488, DY547, Cy5, JF549, and JF646. It will be recognized that dyes that can be conjugated to a protein and a nucleic acid can be used in connection with the present invention.

In some embodiments wherein the polypeptide is labeled, the probe can exhibit increased sensitivity relative to other DNA probes. Without being bound by theory, the increased sensitivity is believed to be at least partially due to the fact that polypeptides can be capable of accepting a higher concentration of labels relative to other known probes that are comprised of nucleic acids.

In some embodiments, the Cas polypeptide is bound to the one or more labels. In some embodiments, the gRNA is bound to the one or more labels. In some embodiments, both the Cas polypeptide and the gRNA are bound to the one or more labels. In some embodiments, each of the multiple labels has a distinct emission color. As will be recognized by one of ordinary skill in the art upon study of this document, where there are multiple labels associated with a probe specific for a particular nucleic acid sequences, there is an ability to amplify the signal associate with detection of that target sequence. In this manner, detection of lower copy nucleic acid sequences can be facilitated.

Figure 11A:
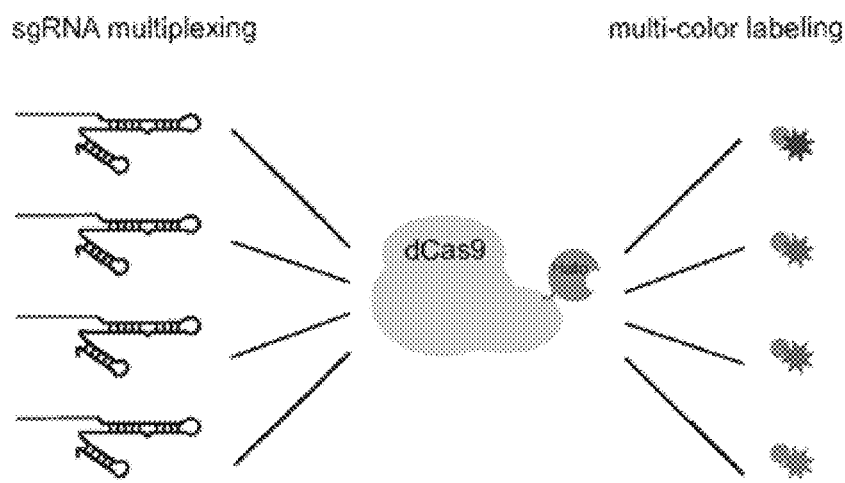
FIG. 11 depicts CASFISH multicolor and multiplexing (A) The advantage of dCas9-Halo for multicolor and multiplexing CASFISH. dCas9-Halo can be labeled with various colored dyes and complexed with various sgRNA targeting different DNA sequences. (B) Concept of the use of single-color or combinatory-color coding to image multiple targets with CASFISH. As shown, a combination of four different colors can detect 15 unique targets.
Figure 11B:
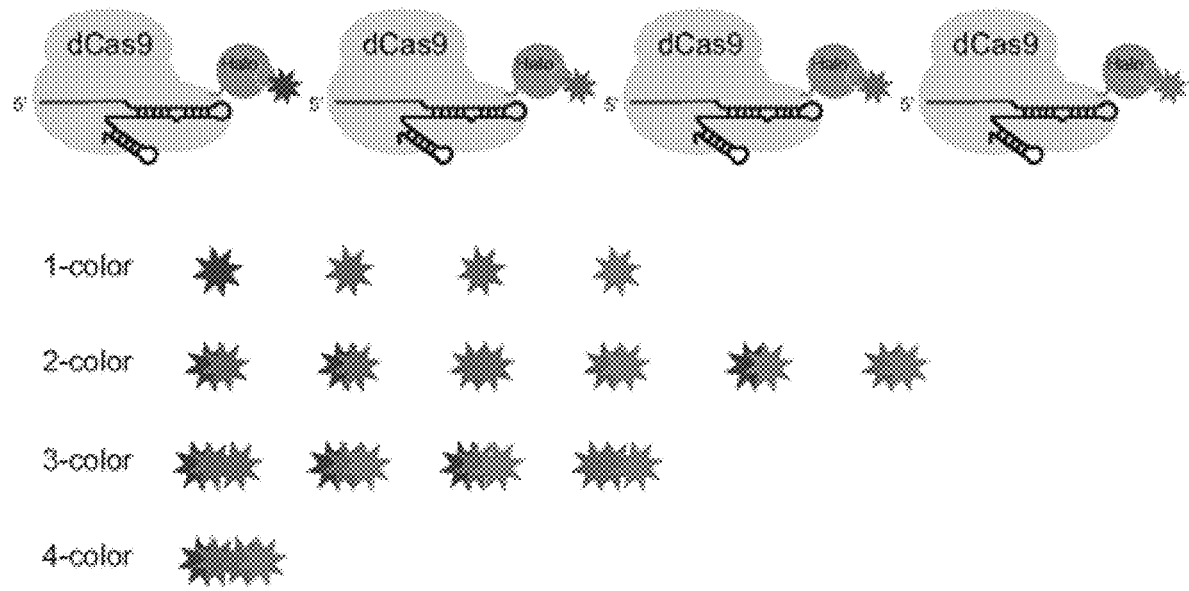

The presently-disclosed subject matter also beneficially allows for multicolor and/or multiplex probes, the understanding of examples of which can be facilitated with reference to FIGS. 11A and 11B.

In some embodiments, the probe can include a Cas polypeptide and multiple gRNAs specific for one or more additional target nucleic acid sequence, wherein each gRNA is complexed with the Cas polypeptide. In some embodiments, the probe can also include multiple labels are bound to the Cas polypeptide, the gRNA, or both. In some embodiments, multiple labels are bound to the Cas polypeptide. Such multiple labels can be bound to the Cas polypeptide, for example via a tag, such as a HaloTag. In some embodiments, each label has a distinct emission color. In some embodiments, the labels are selected from Alexa 488, DY547, Cy5, JF549, and JF646.

In some embodiments, there are a series of probes, each probe comprising a gRNA complexed with a Cas polypeptide, wherein each gRNA is specific for a distinct target nucleic acid sequence, and each probe includes a label having a distinct emission color. In some embodiment, the labels are bound to the Cas polypeptides, the gRNAs, or both. In some embodiments, the labels are bound to each of the Cas polypeptides. Such labels can be bound to the Cas polypeptides, for example via a tag, such as a HaloTag. In some embodiments, each label has a distinct emission color. In some embodiments, the labels are selected from Alexa 488, DY547, Cy5, JF549, and JF646. With reference to FIG. 11B, by way of providing one limiting example, having a panel of labels with four distinct emission colors can allow for detection of 15 unique targets.

As noted here, the presently-disclosed probes further include a gRNA specific for a target nucleic acid sequence, which gRNA is complexed with the Cas polypeptide. In some embodiments of the present probes can include molar ratios of Cas polypeptide to gRNA at a molar ratio of 1:1 to 1:4. A large range of molar ratio can be used to enhance Cas/gRNA complex formation and optimize imaging results. When Cas polypeptide is labeled, equal or more gRNA, at 1:1, 1:2, 1:3, . . . 1:20 or even more is reacted together to enhance complex formation. When gRNA is labeled, equal or more Cas polypeptide is used. When both are labeled, use 1:1 ratio. Variation in ratios may still give good results once followed by extensive wash steps.

The term "gRNA" is used herein to refer to an RNA sequence selected to specifically target a particular nucleic acid sequence of interest (a "target nucleic acid sequence" or a "predetermined nucleic acid sequence"). Complexing between a Cas polypeptide and a gRNA can include the binding of the gRNA and polypeptide by covalent bonding, hydrogen bonding, and/or other non-covalent bonding, and is well-understood in the field of CRISR/Cas systems. Exemplary gRNAs can therefore comprise a section that is targeted for a particular nucleic acid sequence of interest and section that is for binding to the Cas polypeptide, and these sections may or may not be mutually exclusive from one another. Moreover, additional sections may optionally be included in the gRNA.

In some embodiments the present probes include a polypeptide that is conjugated to guide RNA (gRNA), wherein the gRNA is targeted to a predetermined nucleic acid sequence. In some embodiments, the gRNA has a target section. In some embodiments, the gRNA targets and hybridizes with the target nucleic acid sequence. The gRNA can comprise a single RNA molecule in some instances, and in other embodiments the gRNA can be assembled from two or more RNA molecules. The two or more RNA molecules individually may or may not be able to conjugate with the polypeptide, and may or may not target the predetermined nucleic acid sequences. However, upon assembly, the gRNA will perform to target a predetermined nucleic acid sequence.

The gRNA molecules utilized in embodiments of the present probes can vary in sequence length. The portion of the gRNA that has complementarity to a target nucleic acid sequence, the target section, can also vary in length, and can be selected so that the gRNA targets the target nucleic acid sequences (or "particular nucleic acid sequences of interest" or "predetermined nucleic acid sequences") of different lengths. In some embodiments the portion of the gRNA targeted to a predetermined nucleic acid sequence, the predetermined nucleic acid sequence, or the entire gRNA sequence is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more nucleic acids in length. In some preferred embodiments, the target section of the gRNA is about 15-25 nucleic acids in length. In some embodiments, the gRNA has a section binding to the polypeptide but not the target nucleic acid. In some embodiments, this section is about 80 to about 100 nucleic acids in length, more preferably about 90 nucleic acids in length.

Methods and tools for designing gRNAs are known to those of ordinary skill in the art. For example, there are multiple publicly-available tools that can be accessed at the following sites: crispr.mit.edu/; chopchop.rc.fas.harvard.edu/; www.e-crisp.org/; crispr.cos.uni-heidelberg.de/

The terms "target," "targeting," and the like refer to the characteristic of a compound being selectively drawn to and/or selectively bound a target compound. For instance, gRNA that targets a predetermined DNA sequence is drawn to and/or selectively binds the predetermined DNA sequence. In some embodiments a gRNA molecule is said to target a predetermined DNA sequence when the gRNA is hybridizable with the predetermined DNA sequence, wherein the term "hybridize" refers to the binding (e.g., non-covalent binding) of one nucleic acid sequence to another nucleic acid sequence in a sequence specific manner. Hybridizable sequences can therefore be referred to as "complementary" sequences herein.

In some instances 100% complementarity of the target section of a nucleic acid (e.g., gRNA) to its target nucleic acid (e.g., DNA) is not required for hybridization. In some instances, a nucleotide can hybridize over one or more segments such that intervening or adjacent segments are not involved in the hybridization event (e.g., a loop structure or hairpin structure). The target section of a nucleotide can comprise at least 50%, at least 60%, at least 70%, at least 80%, at least 90%, at least 95%, at least 99%, or 100% sequence complementarity to a hybridizable target sequence.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 50%, 55%, 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

The terms "nucleotide," "polynucleotide," "nucleic acid," and "nucleic acid sequence" are also used herein to refer to deoxyribonucleotides or ribonucleotides and polymers thereof in either single or double stranded form. Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified versions thereof (e.g., degenerate codon substitutions) and complementary sequences and as well as the sequence explicitly indicated. Thus, the term nucleotide and the like is inclusive of the gRNAs that are described herein.

The terms "predetermined nucleic acid sequence," "target nucleic acid sequence," and "particular nucleic acid sequence of interest" refer to a nucleic acid sequence of a nucleic acid molecule that is known and was chosen before synthesis of the gRNA in accordance with the invention disclosed herein. Accordingly, in its broadest sense the expression "target nucleic acid sequence" indicates merely that target nucleic acid sequence has a particular known sequence.

The target nucleic acid sequence can be selected from a DNA sequence, an RNA sequence, or a sequence of another nucleic acid analogue such as but not limited to peptide nucleic acid (PNA), Morpholino and locked nucleic acid (LNA), as well as glycol nucleic acid (GNA) and threose nucleic acid (TNA). In some embodiments, the target nucleic acid sequence is a nucleic acid molecule in which one or more nucleotides have been modified such as but not limited to methylation, and hydroxymethylation. As noted herein, the target nucleic acid sequence can be in native DNA that has not been denatured, and the target nucleic acid sequence can be within chromosomal DNA that has not been denatured.

The target nucleic acid sequence can be contained in any sample containing genetic material. In this regard, the probes, kits, and methods disclosed herein are useful for detecting and imaging target nucleic acid sequence(s) in a sample(s) containing genetic material.

The sample types are not particularly limited so long as the samples comprise genetic material. In some embodiments, the cell is a human cell. In some embodiments, the sample comprises a virus, bacteria or fungus. In some embodiments, the sample is a cell. The cell can be a live cell or a fixed cell. The cell can be a plant cell or an animal cell. In some embodiments the sample includes an entire native chromosome and/or a portion of a native chromosome. In some embodiments, the cell can be a human cell.

Thus, in some embodiments the samples include cells obtained from a subject. Exemplary samples from a subject may include chromosome spreads for genetic testing, cultures, prenatal materials, samples for in vitro fertilization, swabs, air filters, water cooling towers, food, drink, hair, stool, urine, saliva, blood, lymph, sputum, cervical smears, sperm, sections of tissues from biopsies, sections of tissues from autopsies, and the like. Samples can include fixed tissue samples by various fixation methods known in the art. Examples of chemical fixation include formaldehyde, paraformaldehyde, formamide, glutaraldehyde, Tween-20 and HCl, acetic acid and methanol, and other aldehydes and alcohols.

The presently-disclosed subject matter further includes kits, which include probes or components of probes as disclosed herein. Exemplary kits can include a Cas polypeptide, a gRNA specific for a target nucleic acid sequence for complexing with the Cas polypeptide, and a label capable of being bound to the Cas polypeptide, the gRNA, or both. In some embodiments the kits are provided with a label is already bound to the Cas polypeptide. Subsequently, prior to performing an imaging procedure, one may mix the components of the kits to obtain a probe or collection of probes. The ability to store the probes as kits that include separate components permits one to synthesize the polypeptide separately from the gRNA. Maintaining the components separate from one another can also increase the shelf life of certain embodied probes relative to probes that stored in a state wherein the polypeptide and gRNA are already assembled or relative other known probes.

Additionally, the present probes and kits permit for a wide variety of customization and configuration of the probes. For instance, because each probe is not individually labeled, but instead the polypeptides can all be labeled in advance, different probes can be synthesized by conjugating the labeled polypeptides to different gRNA. Thus, a set of labeled polypeptides can be adapted for use as probes for a variety of different predetermined sequences with relative ease by altering the gRNA that is conjugated to the polypeptides. This can present significant cost savings over other known probes that are preassembled and are each individually labeled for specific DNA sequences.

In some embodiments, the kit further includes a tag, as described herein. In some embodiments of the kit, the label is a tag for use in subsequent secondary labeling. In some embodiments, the tag comprises an antibody target and the kit further includes an antibody against the antibody target.

In some embodiments, the kit also includes reagents for preparing a sample containing the target nucleic acid sequence. For example, the kit can include reagents for fixing the sample, as described herein, or by any method known in the art.

The presently-disclosed subject matter further relates to methods for imaging nucleic acids using the presently-disclosed probes. As noted herein, such methods allow for detection and/or visualization of the target nucleic acid sequence and/or a sample containing the target nucleic acid sequence without denaturing the nucleic acid, e.g., without denaturing double-stranded, chromosomal DNA), which can be detrimental to morphology of cells, nuclei, and chromosomes. In this regard, the method can allow for subnuclear localization of sequences in a cell, and for visualizing thee three-dimensional organization of chromosomes in nuclei.

In some embodiments the methods comprise contacting a sample that includes nucleic acid with a probe, and then detecting whether the probe has bound the target nucleic acid sequence. The presence of probe bound to a nucleic acid molecule indicates that the nucleic acid molecule comprises the target nucleic acid sequence to which the probe is targeted. Methods disclosed herein can also involve imaging the sample to determine the location and/or the relative copy number of the target nucleic acid sequence.

The contacting step can also be performed by any known means that bring the probes into direct contact with the sample. In some embodiment, such as embodiments for imaging live cells, the present probes can be contacted to the live cells by delivering the probes using methods such as bead loading, microinjection, nanoparticle or lipid mediated transduction, and the like. Thus, live cell imaging can be performed by delivering probes on or into cells that are in a sample of interest.

Any of the embodiments of the probes as described herein can be used in accordance with the methods of the presently disclosed subject matter, with benefits of the particular selection of the probe(s) being apparent to one of ordinary skill in the art upon study of this document and in view of the desired determination, sample, and target nucleic acid sequence. In some embodiments, the probe includes a Cas polypeptide and multiple gRNAs, each specific for one or more additional target nucleic acid sequence, wherein each gRNA is complexed with the Cas polypeptide; and the method involves detecting whether the probe binds each of the target nucleic acid sequences, wherein binding of the probe to the nucleic acids indicates the presence of the target nucleic acid sequences in the sample. In some embodiments, there is a series of probes, each probe comprising a gRNA complexed with a Cas polypeptide, each gRNA being specific for a distinct target nucleic acid sequence, and each probe including a label having a distinct emission color; and the method involves simultaneously detecting whether the probes bind each of the multiple target nucleic acid sequences. As desired, the method can include imaging the sample to determine the location and/or relative copy number of each of the multiple target nucleic acid sequences.

The detecting and/or imaging step can be performed by any known means, including any known means currently used for fluorescent in situ hybridization imaging. In some embodiments the detecting step is performed with a process that includes magnetic resonance imaging (MRI), x-ray computed tomography (CAT), positron emission tomography (PET), or combinations thereof.

Embodiments of the present probes have the superior and unexpected capability of detecting genomic or native nucleic acids. Known probes are commonly composed of nucleic acid sequences and require fixation and denaturization of DNA in order to detect certain sequences on the DNA. However, embodiments of the present probes are comprised of a polypeptide conjugated with gRNA, and, notwithstanding their relatively large size, are capable of penetrating native DNA to probe for specific predetermined genomic DNA sequences. Embodiments of the present probes can penetrate the nucleus and/or native DNA. In this respect, the polypeptides that comprise certain embodiments of present probes can be mutated to provide enhanced penetration and binding of native DNA sequences.

Embodiments of the present probes can also expedite the entire imaging process because they include the novel characteristic of not requiring fixation and/or denaturization of a sample. For instance, some implementations of the present imaging methods can be performed in about 0.1 hours, 0.5 hours, 1.0 hours, 1.5 hours, 2.0 hours, 2.5 hours, or 3.0 hours. Of course, there may be difficult samples that are performed in longer time frames; however, one advantage of the presently disclosed subject matter is the relatively expeditious process.

Additionally, in some instances a method for imaging is provided that includes providing two or more probes, wherein each probe is targeted to a different predetermined DNA sequence. The probes can be targeted to different nucleic acid sequences by forming the probes with different gRNA. Additionally, each probe that is targeted to a predetermined nucleic acid sequence can be labeled differently, either by using different types of labels on each type of probe or by using labels that emit different fluorescence on each type of probe. After contacting the sample with the two or more probes, one can identify whether any, some, or all of the different types of probes are bound to a nucleic acid sequence. By applying and imaging the different probes together, a "spectral barcode" that includes the point sources of signals from each of the respective types of probes can be created. This permits the visualization and characterization of two or more different predetermined DNA sequences within a sample. This method is referred to herein as two-color CASFISH or multicolor CASFISH.

As described herein, embodiments of the present imaging methods can be provided for the purpose of studying and characterizing translocations within a genetic sample. Some embodiments that do not require fixation and/or denaturization of a nucleic acid sample advantageously can image native chromosomes, thereby permitting relatively easy identification of potential translocations within the sample.

In other embodiments, the present imaging methods can be provided for the purpose of diagnosing or prognosing certain diseases and conditions. Notably, because certain methods can be performed without fixation and hybridization protocols, some embodiments offer a relatively rapid assay for diagnosing or prognosing a subject. This rapidity can be particularly beneficial in time sensitive situations, such diagnostic methods that are performed during surgery to determine the diagnosis and immediate treatment required.

In some embodiments, the target nucleic acid sequence is associated with a disease or condition. In this regard, the sample is obtained from a subject, and the method further involves identifying an increased likelihood of the subject having or developing the disease or condition if the target nucleic acid sequence is detected in the sample and/or the imaging of the sample in indicative of an increased likelihood of the subject having or developing the disease or condition. Although not necessary, in some embodiments, the method can include fixing the sample and/or obtaining a sample that is fixed, as is often common clinical practice.

The terms "diagnosing" and "diagnosis" as used herein refer to methods by which the skilled artisan can estimate and even determine whether or not a subject is suffering from a given disease or condition. Along with diagnosis, making a "prognosis" or "prognosticating" can refer to predicting a clinical outcome (with or without medical treatment), selecting an appropriate treatment (or whether treatment would be effective), or monitoring a current treatment and potentially changing the treatment, based on the presence of a predetermined DNA sequence and/or particular gene in a sample associated with a subject.

"Prognosticating" as used herein refers to methods by which the skilled artisan can predict the course or outcome of a condition in a subject. The term "prognosis" can refer to the ability to predict the course or outcome of a condition with up to 100% accuracy, or predict that a given course or outcome is more or less likely to occur. The term "prognosis" can also refer to an increased probability that a certain course or outcome will occur; that is, that a course or outcome is more likely to occur in a subject exhibiting a mutation, inversion, addition, and/or deletion in the gene, when compared to those individuals not exhibiting the mutation in the gene. In certain embodiments, a prognosis is about a 5% chance of a given expected outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance. If an accurate prognosis can be made, appropriate therapy, and in some instances less severe therapy or more effective therapy, for the patient can be chosen.

Furthermore, the term "subject" is inclusive of human, plant, animal, bacteria, virus other microorganisms, and any subject containing genetic material. Thus, veterinary uses are provided in accordance with the presently disclosed subject matter and the presently-disclosed subject matter provides methods for preventing oxidative damage in mammals such as humans, as well as those mammals of importance due to being endangered; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the treatment of livestock, including, but not limited to, domesticated swine, ruminants, ungulates, horses, poultry, and the like.

In this regard, diagnosis or prognosis can be accomplished by providing probes having gRNAs that are selective for nucleic acid sequences, including DNA sequences and/or genes, that are known to cause and/or are associated with a particular disease or condition, and/or are associated with an increased risk or likelihood of developing a particular disease or condition. The diseases and conditions that can be diagnosed or prognosed by the present methods are not particularly limited, and those of ordinary skill will recognize a multitude of known genes that can be probed to diagnose or prognose for a particular disease or condition. Such diseases and conditions can include, but are not limited to, various types of genetic abnormalities, cancer, and other diseases and conditions. Specific diseases and conditions that may be diagnosed or prognosed including, but not limited to, acute and chronic leukemia including chronic myelogenous leukemia and acute promyelocytic leukemia, lymphoma; multiple myeloma, breast cancer, lung cancer, colon cancer, prostate cancer, sarcomas and tumors of mesenchymal origin, brain tumors including oligodendroglioma, Alzheimer's disease, Parkinson's disease, epilepsy, amyotrophic lateral sclerosis, multiple sclerosis, stroke, autism, Cri du chat, 1p36 deletion syndrome, Angelman syndrome, Prader-Willi syndrome, Velocardiofacial syndrome, Turner syndrome, Klinefelter syndrome, Edwards syndrome, Down syndrome, Patau syndrome, and trisomies 8, 9 and 16, and the like. Additional uses can be for detection of viral infection and integration and parasitic microorganisms (e.g. malaria causing *Plasmodium*). Use of the presently disclosed methods may also be used in genetic tests in agriculture, botanical studies, and breeding.

Those of ordinary skill will recognize that the presently-disclosed imaging methods, which may be inclusive of methods for diagnosis or prognosis, can be further optimized and modified. In some instances the present probes and methods may be modified to be compatible with a broader range of sample types and application purposes. With respect to methods that include a fixation step, such optimizations can include, but are not limited to, varying the ratio of acetic acid and methanol, treatment time, permeablizing formide, and paraformaldehyde for fixing samples.

The presently-disclosed subject matter also includes methods of assembling a probe, as described herein, including methods of assembling a probe in vitro. In some embodiments, the method of assembling a probe in vitro involves selecting a gRNA capable of targeting a nucleic acid sequence of interests, which is optionally labeled the gRNA; providing a Cas polypeptide, which is optionally labeled, wherein at least one of the gRNA and the Cas polypeptide is labeled; mixing and incubating the gRNA and the Cas polypeptide.

The presently-disclosed subject matter further includes a probe, as disclosed herein, which is bound to or in complex with the target nucleic acid sequence(s) and/or wherein the probe is bound to the target nucleic acid sequence of each gRNA. The presently-disclosed subject matter further includes a series of probes, each bound to or in complex with the target nucleic acid sequence(s) and/or wherein each probe of the series is bound to the target nucleic acid sequence of each gRNA. As such, a sample including probe-bound nucleic acid sequences is inclusive of the presently-disclosed subject matter.

The presently-disclosed subject matter is further illustrated by the following specific but non-limiting examples. The following examples may include compilations of data that are representative of data gathered at various times during the course of development and experimentation related to the present invention.

EXAMPLES

The following examples use fluorescently labeled nuclease-deficient Cas9 (dCas9) protein assembled with various single-guide RNA (sgRNA), to demonstrate rapid and robust labeling of repetitive DNA elements in pericentromere, centromere, G-rich telomere, and coding gene loci. Assembling dCas9 with an array of sgRNAs tiling arbitrary target loci, enable the visualization of nonrepetitive genomic sequences. As provided in the following examples, the dCas9/sgRNA binary complex is stable and binds its target DNA with high affinity, allowing sequential or simultaneous probing of multiple targets. The examples provided herein also demonstrate CASFISH assays using differently colored dCas9/sgRNA complexes that allow multicolor labeling of target loci in cells.

Materials and Methods

Sd dCas9 Constructs and Purification.

The *S. pyogenes* Cas9 gene containing the double nuclease mutation (D10A and H840A; dCas9) was cloned into PET302/N (Invitrogen) with an N-terminal hexahistidine affinity tag and a C-terminal Halo tag. A construct with an additional N-terminal aldehyde tag was generated for aldehyde-specific Cy5 labeling (13). All dCas9 fusion proteins were expressed and purified through a three-step FPLC purification protocol as described herein.

dCas9 FPLC.

All dCas9 fusion proteins were expressed and purified through a three-step FPLC purification protocol, as described (20), with the following modifications. Briefly, the protein was expressed in *E. coli* BL21 (DE3) (Agilent Technologies) and was grown in LB medium at 16° C. overnight following induction with 1 mM isopropyl β-d-1-thiogalactopyranoside (IPTG). Cells were lysed in 50 mM sodium phosphate (pH 7.0) and 300 mM NaCl. Clarified lysate was applied to a 1-mL HisTALON (Clontech) affinity column. The bound protein was eluted in 50 mM sodium phosphate (pH 7.0) and 300 mM NaCl by increasing the imidazole concentration to 150 mM and was exchanged into buffer [50 mM Hepes (pH 7.5), 100 mM KCl, 1 mM TCEP] by a 50,000-MWCO centrifugal filter (Millipore Amicon). The protein was purified further with cation ion exchange chromatography (HiTrap SP HP; GE Healthcare) and was eluted with a linear gradient of buffers containing 0.1-1.0 M KCl. The eluted protein was purified further by gel filtration chromatography on a Superdex 200 16/60 column (GE Healthcare) in buffer containing 50 mM Hepes (pH 7.5), 150 mM KCl, and 1 mM TCEP. Protein was stored at −80° C. with additional 20% glycerol.

Live-Cell Imaging of Pericentromeres.

MEFs were transfected with mammalian expression plasmids containing dCas9-Halo and sgMajSat. At 48 h post-transfection, cells were incubated with 300 nM of JF549-Halo ligands for 15 min at 37° C. in a cell incubator. Cells subsequently were washed twice with warm PBS, incubated with fresh and warm medium for another 30 min, washed twice with warm PBS, and changed to fresh medium before imaging.

Immunofluorescence Staining.

The cells were blocked in 1% BSA/10% normal goat serum/0.3 M glycine in 0.1% PBS-Tween 20 for 1 h and then were incubated with Alexa 488-conjugated anti-HP1α antibody (ab185018; Abcam) at a working dilution of 1:50 overnight at 4° C. The cells were washed with PBS and stained with DAPI before imaging. Alexa 488 labeling was imaged using a white light excitation system (SOLA light engine; Lumencor) in conjunction with the proper filter cube sets (CFP-A-Basic-NTE; Semrock).

dCas9 Fluorescent Labeling.

For Halo domain labeling, fluorescent Halo ligands (JF549 and JF646) were mixed in protein samples at ratio of 8:1 and reacted at room temperature for 30 min followed by incubation at 4° C. overnight. The dCas9-Halo with an aldehyde tag was fluorescently labeled with Cy5 hydrazide (GE Healthcare) as described (13). The excessive unreacted fluorescent Halo ligand or Cy5 hydrazide was removed using 40-K molecular weight cut off (MWCO) Zeba spin desalting columns (Thermo Scientific). Protein was eluted in storage buffer containing 50 mM Hepes (pH 7.5), 150 mM KCl, 1 mM Tris(2-carboxyethyl)phosphine (TCEP), and 10% (vol/vol) glycerol, snap frozen in liquid nitrogen, and stored at −80° C. Protein concentration and labeling efficiency were calculated from absorption spectrum and extinction coefficients according to Beer's laws.

sgRNA Synthesis.

The DY547-labeled sgMaj Sat was generated by splint ligation of two fragments: 36 synthetic nucleotides 5' of sgMaj Sat with DY547 (GE Dharmacon), and 77 nucleotides 3' of sgMaj Sat transcribed and purified with T7. The unlabeled sgRNAs were synthesized in vitro by T7 RNA polymerase (MEGAshortscript T7 Kit; Life Technologies) using DNA templates with the following sequence, 5'-TAATACGACTCACTATAGGN17-28GTTTAAGAGCTATGCTGGAAACAGCATAGCAAGTTTAAATAAGGCTAGTCCGT TATCAACTTGAAAAAGTGGCACCGAGTCGGTGC-3' (SEQ ID NO: 8). The template contains a T7 promoter-binding sequence (underlined), the sgRNA target (GGN17-28) (bold), and the sgRNA backbone as reported (6). The T7 template DNA was synthesized by either gBlock (Integrated DNA Technologies) or PCR reactions. Produced sgRNAs were purified by MEGAclear Transcription Clean-Up Kit (Life Technologies), and the quality was verified by 10% denaturing PAGE. Related sequences are listed in Tables 1-3.

TABLE 1

Synthesis of DY547-labeled sgMajSat by splint ligation

| | |
|---|---|
| 5'-sgMajSat | DY547-CCAUAUUCCACGUCCUACAGGUUUAAGAGCUAUGCU (SEQ ID NO: 9) |
| 3'-sgMajSat | GGAAACAGCAUAGCAAGUUUAAAUAAGGCUAGUCCGUUAUC-AACUUGAAAAAGUGGCACCGAGUCGGUGCUUUUUUU (SEQ ID NO: 10) |
| sgMajSat-bridge | AAACTTGCTATGCTGTTTCCAGCATAGCTCTTAAACCTGT (SEQ ID NO: 11) |

TABLE 2

Synthesis of DNA template for T7 transcription of sgRNA: T7 transcription template sequences synthesized by gBlock

| | |
|---|---|
| gBlock_sgMajSat (SEQ ID NO: 12) | GGTGACACTATAGAACTCGAGCAGCTGGATCCTAATACGACTCACTATAGGCCATATTCCACGTACAGGTTTAAGAGCTATGCTGGAAACAGCATAGCAAGTTTAAATAAGGCTAGTCCGTTATCAACTTGAAAAAGTGGCACCGAGTCGGTGC |
| gBlock_sgTelomere (SEQ ID NO: 13) | GGTGACACTATAGAACTCGAGCAGCTGGATCCTAATACGACTCACTATAGGGTTAGGGTTAGGGTTAGGGTTAGTTTAAGAGCTATGCTGGAAACAGCATAGCAAGTTTAAATAAGGCTAGTCCGTTATCAACTTGAAAAAGTGGCACCGAGTCGGTGC |
| gBlock_sgMinSat (SEQ ID NO: 14) | GGTGACACTATAGAACTCGAGCAGCTGGATCCTAATACGACTCACTATAggATCTATTATGTTCTACAGTGGTTTAAGAGCTATGCTGGAAACAGCATAGCAAGTTTAAATAAGGCTAGTCCGTTATCAACTTGAAAAAGTGGCACCGAGTCGGTGC |
| gBlock_sgMBS (SEQ ID NO: 15) | GGTGACACTATAGAACTCGAGCAGCTGGATCCTAATACGACTCACTATAGGTCGACTCTAGAAAACATGGTTTAAGAGCTATGCTGGAAACAGCATAGCAAGTTTAAATAAGGCTAGTCCGTTATCAACTTGAAAAAGTGGCACCGAGTCGGTGC |

Design of the T7 transcription template (TAATACGACTCACTATAGGN17-28GTTTAAGAGCTATGCTGGAAACAG-CATAGCAAGTTTAAATAAGGCTAGTCCGTTATCAACTTGAAAAAGTGGCACCGAGTCGGTGC)(SEQ ID NO: 8). Lowercase "g" denotes additional guanines that are not complementary to sgRNA targets

TABLE 3

T7 transcription template synthesized by PCR
Table 3

| Sequence name | Sequence |
|---|---|
| Design of the forward primers (SEQ ID NO: 16) | TAATACGACTCACTATAGGN$_{17-28}$GTTTAAGAGCTATGCTGG |
| sgRNA backbone (SEQ ID NO: 17) | TAATACGACTCACTATAGGGTTTAAGAGCTATGCTGG |
| sgMUC4-I1 (SEQ ID NO: 18) | TAATACGACTCACTATAgGAGGTGACACCGTGGGCTGGGGGTTTAAGAGCTATGCTGG |
| sgMUC4-E2 (SEQ ID NO: 19) | TAATACGACTCACTATAgGAAGTGTCGACAGGAAGAGTTTAAGAGCTATGCTGG |
| sgMUC1-E2 (SEQ ID NO: 20) | TAATACGACTCACTATAgGAAGGTATGGGTGTGGAAGGTATGTTTAAGAGCTATGCTGG |

TABLE 3-continued

T7 transcription template synthesized by PCR
Table 3

| Sequence name | Sequence |
| --- | --- |
| sgMUC4-tiling forward primers | |
| sgMUC4_01 (SEQ ID NO: 21) | TAATACGACTCACTATAgGAAGAGTGGAGGCCGTGCGCGGGTTTAAGAGCTATGCTGG |
| sgMUC4_02 (SEQ ID NO: 22) | TAATACGACTCACTATAgGACCTCAGGTGATCTCCTGCCTGTTTAAGAGCTATGCTGG |
| sgMUC4_03 (SEQ ID NO: 23) | TAATACGACTCACTATAgGTATATTTAGTAGAGACGGTTTAAGAGCTATGCTGG |
| sgMUC4_04 (SEQ ID NO: 24) | TAATACGACTCACTATAgGAGTAGCTGGAATTACAGGTGGTTTAAGAGCTATGCTGG |
| sgMUC4_05 (SEQ ID NO: 25) | TAATACGACTCACTATAgGCTCACTGCAACCTCCACCTCCCGTTTAAGAGCTATGCTGG |
| sgMUC4_06 (SEQ ID NO: 26) | TAATACGACTCACTATAgGACAGAGTCTCGCTCTCTCTCCCGTTTAAGAGCTATGCTGG |
| sgMUC4_07 (SEQ ID NO: 27) | TAATACGACTCACTATAgGAAGAGGAGAAAAGTGGGGAAGGTTTAAGAGCTATGCTGG |
| sgMUC4_08 (SEQ ID NO: 28) | TAATACGACTCACTATAgGAACAGAGGGCCAGAGAGCAGCCGTTTAAGAGCTATGCTGG |
| sgMUC4_09 (SEQ ID NO: 29) | TAATACGACTCACTATAgGTCTTTCTCTCTGCGAGTAAGCCTGTTTAAGAGCTATGCTGG |
| sgMUC4_10 (SEQ ID NO: 30) | TAATACGACTCACTATAgGTACACCCTTGTGTACAGAGCTGTTTAAGAGCTATGCTGG |
| sgMUC4_11 (SEQ ID NO: 31) | TAATACGACTCACTATAgGAAAACTCATGTAAAGCTGCAGTTTAAGAGCTATGCTGG |
| sgMUC4_12 (SEQ ID NO: 32) | TAATACGACTCACTATAgGCAAGCAAGGGAAGCGACAAGGGTTTAAGAGCTATGCTGG |
| sgMUC4_13 (SEQ ID NO: 33) | TAATACGACTCACTATAGGAGGCGGCCAGGGCGCAGAGTTTAAGAGCTATGCTGG |
| sgMUC4_14 (SEQ ID NO: 34) | TAATACGACTCACTATAgGCTTTTAAACCCGAGCTCAGGTTTAAGAGCTATGCTGG |
| sgMUC4_15 (SEQ ID NO: 35) | TAATACGACTCACTATAgGTAGCCCCGGCATTGGCCTTGTTTAAGAGCTATGCTGG |
| sgMUC4_16 (SEQ ID NO: 36) | TAATACGACTCACTATAgGCCTGTGGGAGATGTTCCCTCGTTTAAGAGCTATGCTGG |
| sgMUC4_17 (SEQ ID NO: 37) | TAATACGACTCACTATAgGTCCTGAAGCCAGAGGGACAGCCGTTTAAGAGCTATGCTGG |
| sgMUC4_18 (SEQ ID NO: 38) | TAATACGACTCACTATAgGAGTCTTTGGGGGAGAGTCTGTTTAAGAGCTATGCTGG |
| sgMUC4_19 (SEQ ID NO: 39) | TAATACGACTCACTATAgGCTCCTGCCCTGCCTCTCAGCGTTTAAGAGCTATGCTGG |
| sgMUC4_20 (SEQ ID NO: 40) | TAATACGACTCACTATAgGCATATTTGAGGAGCTTCCTGTTTAAGAGCTATGCTGG |
| sgMUC4_21 (SEQ ID NO: 41) | TAATACGACTCACTATAGGCTGCAAGAGAAGCCATGCGTTTAAGAGCTATGCTGG |
| sgMUC4_22 (SEQ ID NO: 42) | TAATACGACTCACTATAgGATGTTTCAGGACTAGGCTGAGTTTAAGAGCTATGCTGG |
| sgMUC4_23 (SEQ ID NO: 43) | TAATACGACTCACTATAgGCTGGAGGGTGGGAGGTGTAGTTTAAGAGCTATGCTGG |
| sgMUC4_24 (SEQ ID NO: 44) | TAATACGACTCACTATAGGTGGGATGAGCACTGGAGCGTTTAAGAGCTATGCTGG |

TABLE 3-continued

T7 transcription template synthesized by PCR
Table 3

| Sequence name | Sequence |
| --- | --- |
| sgMUC4_25 (SEQ ID NO: 45) | TAATACGACTCACTATAgGCCCTGCAGATGTGGTTGAGTTTAAGAGCTATGCTGG |
| sgMUC4_26 (SEQ ID NO: 46) | TAATACGACTCACTATAgGAGGCTGGGGCTTGGGGCGCCGTTTAAGAGCTATGCTGG |
| sgMUC4_27 (SEQ ID NO: 47) | TAATACGACTCACTATAgGTCTTTGCCGTGAACTGTTCGTTTAAGAGCTATGCTGG |
| sgMUC4_28 (SEQ ID NO: 48) | TAATACGACTCACTATAgGACCGGGGCCCTGGGGAGACACGTTTAAGAGCTATGCTGG |
| sgMUC4_29 (SEQ ID NO: 49) | TAATACGACTCACTATAgGCTGGACACTCAGCTCCATGGTTTAAGAGCTATGCTGG |
| sgMUC4_30 (SEQ ID NO: 50) | TAATACGACTCACTATAgGAGCGCAGAGGGGCAAGACCTGTTTAAGAGCTATGCTGG |
| sgMUC4_31 (SEQ ID NO: 51) | TAATACGACTCACTATAgGAGAAGGAGTGAAGGACTGTGTTTAAGAGCTATGCTGG |
| sgMUC4_32 (SEQ ID NO: 52) | TAATACGACTCACTATAgGCTCCACGACATGCCTAGCTTCTTCGTTTAAGAGCTATGCTGG |
| sgMUC4_33 (SEQ ID NO: 53) | TAATACGACTCACTATAgGAGCTGGGCCAGGAGAGGAGAGTTTAAGAGCTATGCTGG |
| sgMUC4_34 (SEQ ID NO: 54) | TAATACGACTCACTATAgGACCGGGCATGACCAGGGCCTGTTTAAGAGCTATGCTGG |
| sgMUC4_35 (SEQ ID NO: 55) | TAATACGACTCACTATAGGGCAGCCCCCACCCCCACAGTTTAAGAGCTATGCTGG |
| sgMUC4_36 (SEQ ID NO: 56) | TAATACGACTCACTATAgGTTCCTTTTGGCTCCCTGAAGGTTTAAGAGCTATGCTGG |
| sgMUC4_37 (SEQ ID NO: 57) | TAATACGACTCACTATAGGGTCTGTTTGCACACTTGCGTTTAAGAGCTATGCTGG |
| sgMUC4_38 (SEQ ID NO: 58) | TAATACGACTCACTATAgGCCCAGGCCAGAGGAAAAACACAGTTTAAGAGCTATGCTGG |
| sgMUC4_39 (SEQ ID NO: 59) | TAATACGACTCACTATAgGTTTCCTTAAGGAACAGCCCGTTTAAGAGCTATGCTGG |
| sgMUC4_40 (SEQ ID NO: 60) | TAATACGACTCACTATAgGCAGACAGAGGTGGGCTAGACAGTTTAAGAGCTATGCTGG |
| sgMUC4_41 (SEQ ID NO: 61) | TAATACGACTCACTATAgGCCCCAGGCAGGAATGACTCAGAGTTTAAGAGCTATGCTGG |
| sgMUC4_42 (SEQ ID NO: 62) | TAATACGACTCACTATAgGACCCAGTTGCCTTTCCCTGGTTTAAGAGCTATGCTGG |
| sgMUC4_43 (SEQ ID NO: 63) | TAATACGACTCACTATAgGACCCCAGGGAGGTGACAGGCGTTTAAGAGCTATGCTGG |
| sgMUC4_44 (SEQ ID NO: 64) | TAATACGACTCACTATAgGCCACAGCGCACTCCACGGGGAAGTTTAAGAGCTATGCTGG |
| sgMUC4_45 (SEQ ID NO: 65) | TAATACGACTCACTATAgGTCCCAGACTGACAGATAGACCGTTTAAGAGCTATGCTGG |
| sgMUC4_46 (SEQ ID NO: 66) | TAATACGACTCACTATAgGAGGGGTCTGTGGAGAGTTTGTTTAAGAGCTATGCTGG |
| sgMUC4_47 (SEQ ID NO: 67) | TAATACGACTCACTATAgGTCCAGCATCAGCGACGCCCTGTTTAAGAGCTATGCTGG |
| sgMUC4_48 (SEQ ID NO: 68) | TAATACGACTCACTATAgGCCTAAGACTCCAGAGCCAAAGTTTAAGAGCTATGCTGG |
| sgMUC4_49 (SEQ ID NO: 69) | TAATACGACTCACTATAgGCTACTACGTAGGGTTGTCATGGTTTAAGAGCTATGCTGG |

TABLE 3-continued

T7 transcription template synthesized by PCR

| Sequence name | Sequence |
|---|---|
| sgMUC4_50 (SEQ ID NO: 70) | TAATACGACTCACTATAgGTAAAGTAGAAAAGGCATAAAGTTTAAGAGCTATGCTGG |
| sgMUC4_51 (SEQ ID NO: 71) | TAATACGACTCACTATAgGCACTTTTGGAGGCCCAGGCGTTTAAGAGCTATGCTGG |
| sgMUC4_52 (SEQ ID NO: 72) | TAATACGACTCACTATAgGTGGAGACAGGGTTGGCCAAGCGTTTAAGAGCTATGCTGG |
| sgMUC4_53 (SEQ ID NO: 73) | TAATACGACTCACTATAgGCTCCCTGCAACCTCTGCCTCCCGTTTAAGAGCTATGCTGG |
| sgMUC4_54 (SEQ ID NO: 74) | TAATACGACTCACTATAgGCCTCTTTCTCAAACACGTCTTTAGTTTAAGAGCTATGCTGG |
| sgMUC4_55 (SEQ ID NO: 75) | TAATACGACTCACTATAgGAACCCGGAATGGCACTTGTGTGTTTAAGAGCTATGCTGG |
| sgMUC4_56 (SEQ ID NO: 76) | TAATACGACTCACTATAGGTGGCTTTTTAGAGGCACGGTTTAAGAGCTATGCTGG |
| sgMUC4_57 (SEQ ID NO: 77) | TAATACGACTCACTATAGGCTTGGTGTATTCAGAATGGTTTAAGAGCTATGCTGG |
| sgMUC4_58 (SEQ ID NO: 78) | TAATACGACTCACTATAgGCACTGCCAGGCCAGCCTCTGCCGTTTAAGAGCTATGCTGG |
| sgMUC4_59 (SEQ ID NO: 79) | TAATACGACTCACTATAgGCTAAGGACAAGAGGCAATGAGGTTTAAGAGCTATGCTGG |
| sgMUC4_60 (SEQ ID NO: 80) | TAATACGACTCACTATAgGACTCAATTTCTCAGAACATGCTGGTTTAAGAGCTATGCTGG |
| sgMUC4_61 (SEQ ID NO: 81) | TAATACGACTCACTATAgGACAGAGTTTCTCTCTGTCCCCCGTTTAAGAGCTATGCTGG |
| sgMUC4_62 (SEQ ID NO: 82) | TAATACGACTCACTATAGGGGTTTCACCATGTTGGCCGTTTAAGAGCTATGCTGG |
| sgMUC4_63 (SEQ ID NO: 83) | TAATACGACTCACTATAgGCTCGCCTCGGCTCCCAAAGTGCGTTTAAGAGCTATGCTGG |
| sgMUC4_64 (SEQ ID NO: 84) | TAATACGACTCACTATAGGGCATTTGTGTTGCACGTGGTTTAAGAGCTATGCTGG |
| sgMUC4_65 (SEQ ID NO: 85) | TAATACGACTCACTATAgGAGTGGAGCTGCGGGCAACCCGTTTAAGAGCTATGCTGG |
| sgMUC4_66 (SEQ ID NO: 86) | TAATACGACTCACTATAgGTAGAGATGCCGCCCCGCCCGTTTAAGAGCTATGCTGG |
| sgMUC4_67 (SEQ ID NO: 87) | TAATACGACTCACTATAgGTCCAGTGGCCAGTGGATTTTGGTTTAAGAGCTATGCTGG |
| sgMUC4_68 (SEQ ID NO: 88) | TAATACGACTCACTATAgGAGGCAGCTGGGACTAGAACCCGTTTAAGAGCTATGCTGG |
| sgMUC4_69 (SEQ ID NO: 89) | TAATACGACTCACTATAgGTCGGTGGGCTGGGCTGGTTGTTTAAGAGCTATGCTGG |
| sgMUC4_70 (SEQ ID NO: 90) | TAATACGACTCACTATAgGAATGAATGGCTGTCTCAGCAGTTTAAGAGCTATGCTGG |
| sgMUC4_71 (SEQ ID NO: 91) | TAATACGACTCACTATAgGAAACAGACGTGGCCCAGTCTCTGTTTAAGAGCTATGCTGG |
| sgMUC4_72 (SEQ ID NO: 92) | TAATACGACTCACTATAgGCTGAGAGCTGCATTTCGAAGTTTAAGAGCTATGCTGG |
| sgMUC4_73 (SEQ ID NO: 93) | TAATACGACTCACTATAgGACAAGTCAGGAAGGGCCCTGTGGTTTAAGAGCTATGCTGG |

PCR template: GCACCGACTCGGTGCCACTTTTTCAAGTTGATAACGGACTAGCCTTATTTAAACTTGC-TATGCTGTTTCCAGCATAGCTCTTAAAC (SEQ ID NO: 94); reverse primer: GCACCGACTCGGTGCCACTT (SEQ ID NO: 95). Lowercase "g" denotes additional guanines that are not complementary to sgRNA targets.

Cell Culture and Brain Section Preparation.

MEFs and HeLa cells were cultured in DMEM without Phenol-red (Gibco) supplemented with 10% FBS and 1% penicillin/streptomycin. Cytogenetic analysis of MEF cells was performed by Cell Line Genetics. Cryostat sections were prepared from freshly frozen adult mouse brain with a slice thickness of ~20 μM.

CASFISH Protocol

Unless indicated, the standard CASFISH protocol is as follows: Cells cultured on 35-mm MatTek dishes or tissue sections were fixed at −20° C. for 20 min in a prechilled solution of methanol and acetic acid at a 1:1 ratio. Samples were washed three times (5 min each washing) with PBS with gentle shaking, followed by incubation for 15 min at 37° C. in blocking/reaction buffer [20 mM Hepes (pH 7.5), 100 mM KCl, 5 mM MgCl2, freshly added 1 mM DTT, 5% (vol/vol) glycerol, 1% BSA, and 0.1% TWEEN-20]. To assemble CASFISH probes, fluorescently labeled dCas9 protein (5-25 nM) was mixed with labeled or unlabeled sgRNA at molar ratio of 1:1 or 1:4, respectively, in blocking/reaction buffer and was incubated at room temperature for 10 min and stored on ice before the next step. Five nM of fluorescent dCas9 protein was used for CASFISH against MUC4 repetitive DNA elements. For all other CASFISH experiments, 25 nM dCas9 protein was used. The assembled dCas9/sgRNA was applied on preblocked cells and incubated for 5-30 min at 37° C. The reaction was terminated by the removal of the dCas9/sgRNA solution and washing three times with blocking/reaction buffer. CASFISH samples of sgMUC4-tiling were washed further in buffer containing 20 mM Hepes (pH 7.5), 300 mM NaCl, 3 M urea, and 1.1% (vol/vol) Nonidet P-40. The short CASFISH protocol was modified to the following procedures: Cells were fixed for 5 min at −20° C., rinsed three times with PBS, subjected to the preincubated (5 min) dCas9 and sgRNA mixture for 5 min at 37° C., and again rinsed three times with PBS. All samples were stained with 0.5 μg/mL DAPI for 5 min before imaging.

EMSA Assay.

dCas9 protein and sgRNA were incubated together at room temperature for 10 min to examine the binary complex and subsequently were incubated with target DNA at 37° C. for 15 min to examine the tertiary complex. For the competition assay, an additional binary or tertiary complex reaction was performed after the addition of the competitor molecules. Resulting reaction mixtures were subjected to electrophoresis of 1% agarose gel in 1×Tris/borate/EDTA buffer containing 5 mM MgCl2 and were imaged with GE Typhoon Trio+ Imagers.

Microscopy and Image Analysis.

All CASFISH samples were imaged on an inverted microscope (Nikon Eclipse Ti) equipped with a 100× oil-immersion objective (Nikon CFI Plan Apo VC 100× Oil, NA 1.4) and an EM CCD (Andor iXon Ultra 897). DAPI, JF549, or JF646 labeling was imaged using a white light excitation system (SOLA light engine; Lumencor) in conjunction with the proper filter cubes sets (DAPI-1160B-NTE-Zero, LF561/LP-A-NTE, or Cy5-3040C-NTE-Zero, respectively; Semrock). JF549 or JF646 labeling also was imaged using laser excitation [561 nm (Cobolt Jive) or 637 nm (Vortran Stradus), respectively] in conjunction with a multiband dichroic (Di01-R405/488/561/635; Semrock). Proper emission filters for JF549 or JF6464 (FF01-593/40 or FF01-676/37; Semrock) were placed in front of the camera. Z-stacks were collected at step size of 0.2 μm for 30-40 slices to image the entire nucleus. Images were processed using ImageJ (21).

Example 1: Fluorescently Labeled dCas9 Protein

To produce fluorescently labeled dCas9 protein, we constructed a dCas9 fusion protein that contains a hexahistidine affinity tag at the N terminus and a Halo tag at the C terminus. The Halo tag can be labeled efficiently and covalently by Halo ligands conjugated to a variety of organic fluorescent dyes for different imaging purposes (10). We purified recombinant dCas9 fusion protein expressed in *Escherichia coli* and labeled the protein with Halo ligands conjugated with Janelia Fluor 646 (JF646) (11). (All fluorochromes are listed in Table 1.)

TABLE 1

Spectral properties of fluorochromes

| Fluorochrome | Absorption maximum, nm | Emission maximum, nm | Emission color |
|---|---|---|---|
| Alexa 488 | 495 | 519 | Green |
| DY547 | 557 | 574 | Orange |
| Cy5 | 650 | 670 | Red |
| JF549 | 549 | 571 | Orange |
| JF646 | 646 | 664 | Red |

Figure 1B:
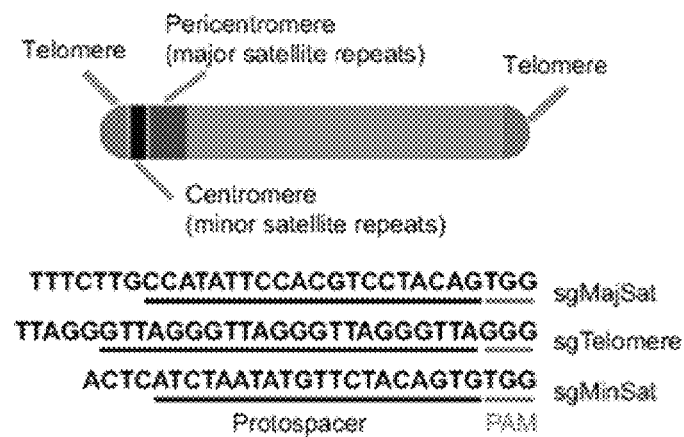
Figure 1C:
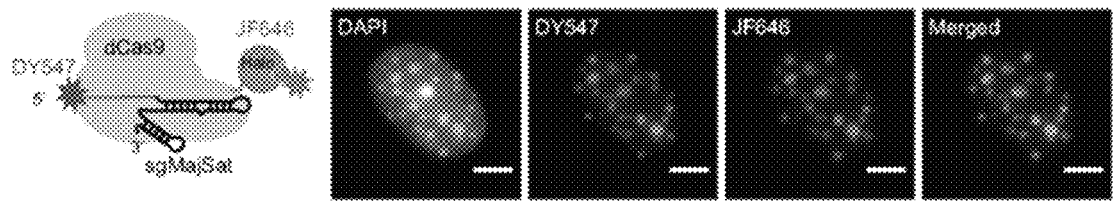
Figure 2A:
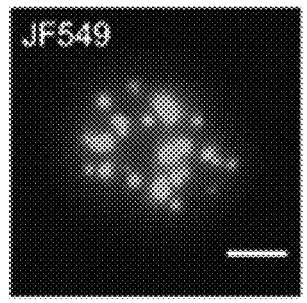
FIG. 2 includes images and schematics using dCas9 sgRNA complexes, including live-cell imaging (A) Live-cell imaging of pericentromeres in MEFs expressing dCas9-Halo and sgMaj Sat. (B) sgMaj Sat (SEQ ID NO: 5) and sgMaj Sat-2 (SEQ ID NO: 96) sequences and CASFISH against sgMaj Sat-2 in MEFs. (C) Anti-HP1α immunofluorescence staining in pericentromeres costained with sgMaj Sat CASFISH. (D) CASFISH controls using the indicated reagents demonstrated that detection of pericentromeres requires the complex formed by dCas9 protein and the full-length sgRNA. Maximum projection of z-stacks is shown. (Scale bars, 5 μM.)
Figure 2B:
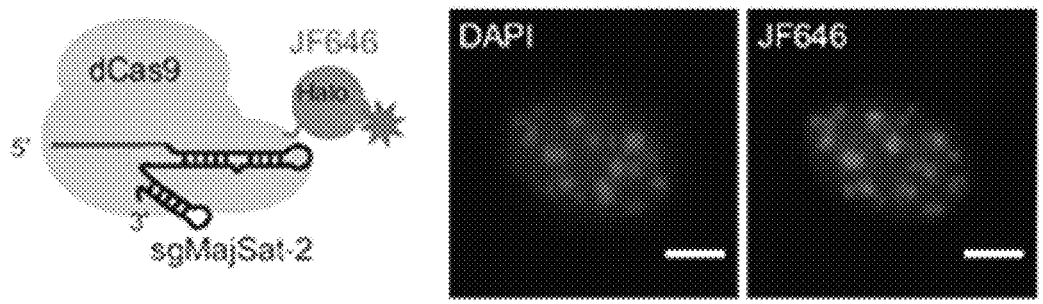
Figure 2C:
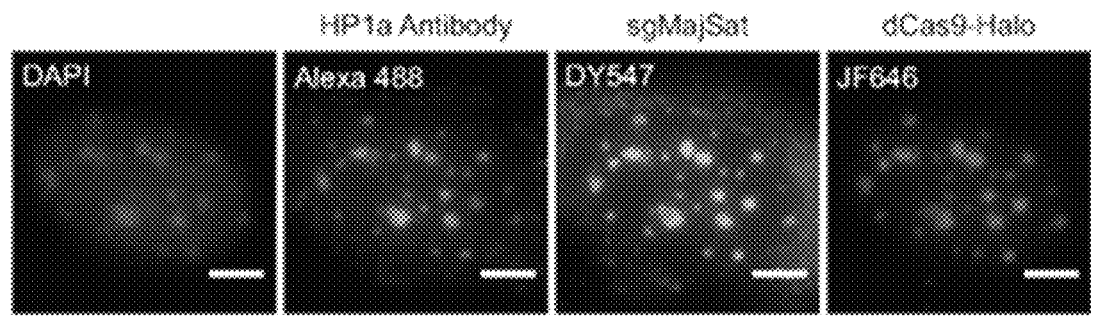
Figure 2D:
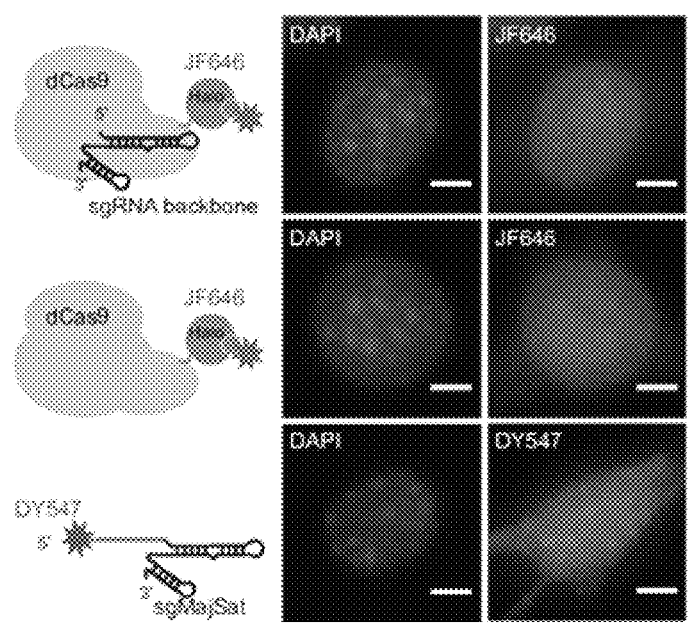
Figure 3A:
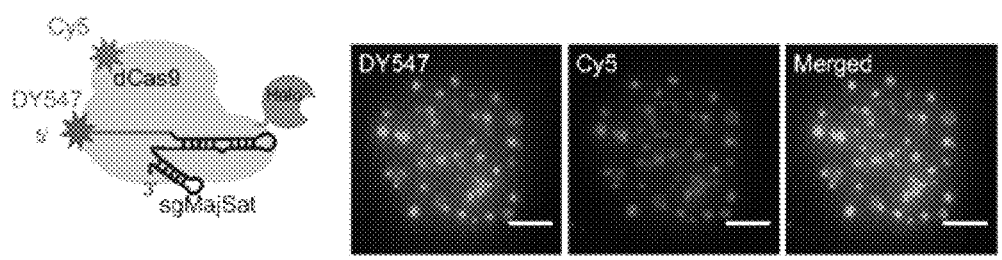
FIG. 3 includes schematics and images of CASFISH using Cy5-labeled dCas9 protein. (A) DY547-labeled full-length sgMajSat detected pericentromeres. (B) The indicated truncated forms of unlabeled sgRNA or absence of sgRNA failed to detect the pericentromeres. Maximum projection of z-stacks is shown. (Scale bars, 5 μM.)
Figure 3B:
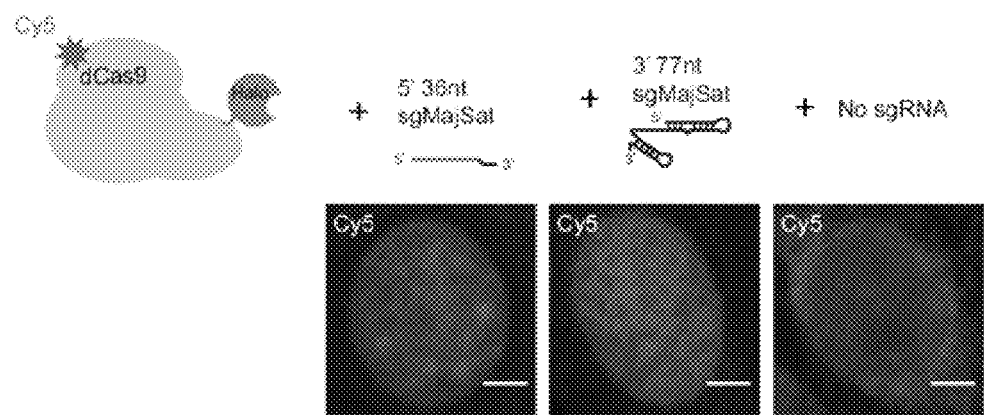

The presently disclosed strategy was tested on the highly repetitive major satellite (MajSat) sequences at murine pericentromeric regions and thus generated a 5'-DY547 (Cy3 alternative)-labeled sgRNA (sgMajSat) (FIG. 1B). Equal molar amounts of purified JF646-dCas9 and DY547-sgMajSat were incubated together to form the dCas9/sgMajSat complex and then were applied to mouse embryonic fibroblasts (MEFs) that were fixed with methanol/acetic acid solution. Within 30 min of incubation, dCas9/sgMajSat probes effectively hybridized to the target satellite DNA in pericentromeres (FIG. 1C). Images from the DY547 channel that detects sgMaj Sat, the JF646 channel that detects dCas9 protein, and the DAPI channel generated a colocalized pattern of the pericentromeres in nuclei. Pericentromeres were of various sizes and numbers, as observed in live MEF cells coexpressing dCas9-halo and sgMajSat (FIG. 2A). Staining of pericentromeres by the fluorescent dCas9/sgMajSat complex was verified further by dCas9 staining with an independent sgRNA (sgMajSat-2) targeting the other strand of the major satellite sequence (FIG. 2B) and by its colocalization with heterochromatin protein 1 alpha (HP1α) immunofluorescence staining (FIG. 2C). In contrast, JF646-dCas9 alone or incubated with the backbone hairpin portion of sgMaj Sat lacking a target complementary sequence failed to generate any specific staining (FIG. 2D) indicating that dCas9/sgMajSat-mediated staining of pericentromeres was sequence-specific. DY547-sgMajSat alone did not hybridize with the target major satellite DNA, suggesting that the target DNA was not denatured during the Cas9-mediated FISH (CASFISH) procedure and that the observed signal was not caused simply by RNA-DNA hybridization independent of dCas9 (FIG. 2D). To demonstrate dCas9-mediated fluorescent staining with an independent labeling method, we engineered a genetically encoded aldehyde tag to the N terminus of dCas9 protein and labeled the aldehyde-tagged dCas9 with Cy5 hydrazide (Cy5 Hz) (13). The Cy5-labeled dCas9 protein assembled with DY547-sgMajSat generated the same specific staining of pericentromeres as JF646-labeled dCas9 protein (FIG. 3). In summary, these results demonstrated that in vitro assembled fluorescent dCas9/sgRNA complex could label its genomic DNA target sequences in cells effectively and specifically. We therefore named the method "CRISPR/Cas9-mediated FISH," CASFISH.

Example 2: Halo Tag Labeling

Figure 1D:
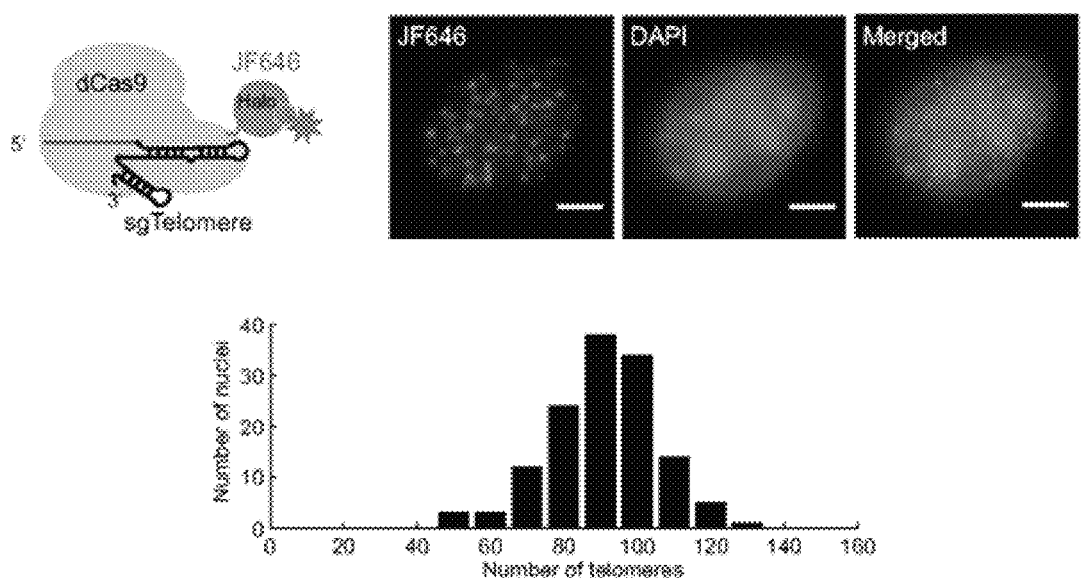
Figure 1E:
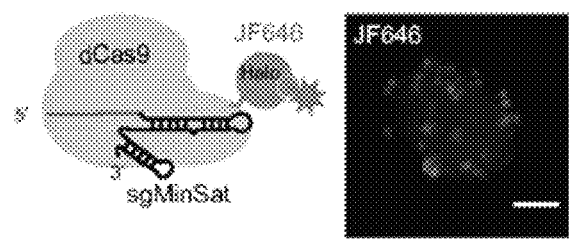

The synthesis of fluorochrome-conjugated sgRNA probes (~110 nt) is costly, whereas labeling of the Halo tag is efficient and cost-effective; thus this example describes the strategy of assembling fluorescent dCas9-Halo and unlabeled sgRNA for CASFISH. Specifically, we labeled dCas9-Halo protein through Halo ligands providing flexibility in the choice of fluorochromes and used T7 polymerase to synthesize sgRNA in vitro, a solution combining low cost and scalability for multiplexing. dCas9-Halo proteins labeled with both tested fluorochromes [JF549 and JF646 (11)] retained their activity, as demonstrated by successful CASFISH imaging and specific binding to target DNA in vitro (see below). Assembling labeled dCas9-Halo with T7-synthesized sgRNA, we successfully stained various DNA targets including telomeres, minor satellites, and a gene array containing repeated MS2-binding sequences (FIG. 1D and FIG. 1E and FIG. 4A). The number of detected telomeres was in agreement with the number of chromosomes in MEF cells by cytogenetic analysis (FIG. 1D and FIG. 4B and FIG. 4C). Telomere sequences are G-rich and have a higher melting temperature than regular genomic DNA. Although conventional DNA FISH of telomeres requires peptide nucleic acid probes for hybridization, the CASFISH probe detected telomeres effectively with unmodified sgRNA, indicating CASFISH's superiority to DNA FISH in detecting G-rich sequences. Thus, we established a cost-effective and convenient pipeline for synthesizing fluorescent CASFISH probes for customized sequences.

Example 3 CASFISH for Multiple DNA Targets

Figure 5A:
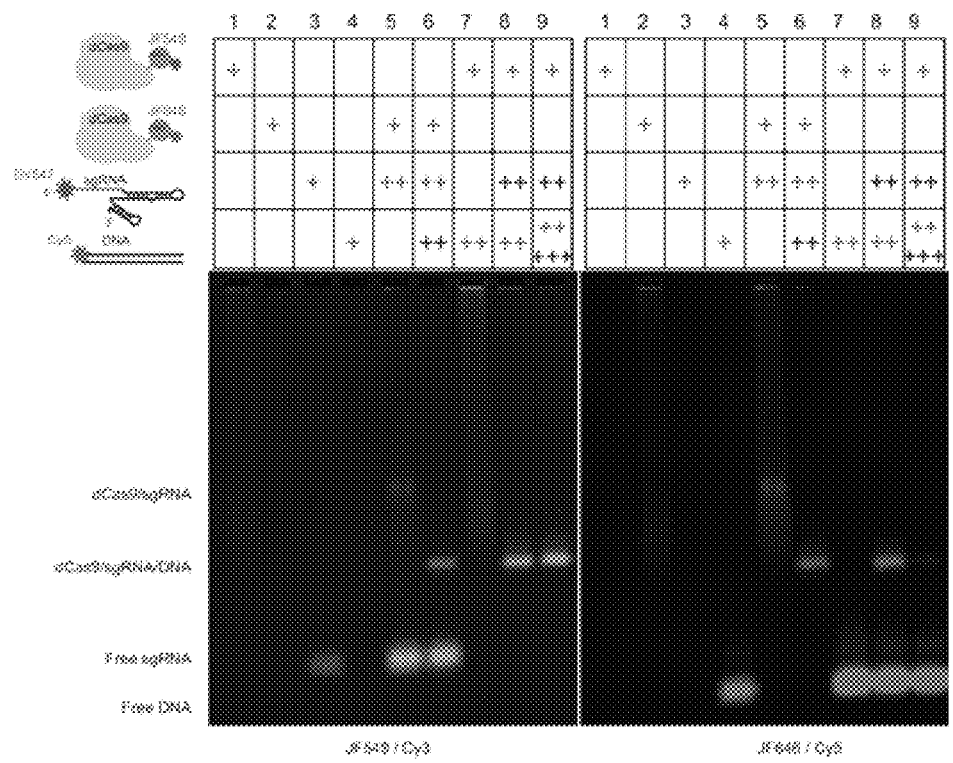
FIG. 5 includes schematics and assays of CASFISH as well as a histogram demonstrating stability of the tertiary complex formed by dCas9, sgRNA, and DNA: (A) EMSA assays of reactions using the indicated fluorescent or unlabeled reagents on 1% agarose gel. The gel was scanned with the two indicated filter settings, a green channel detecting JF549 and DY547 and a red channel detecting JF646 and Cy5. The color of the plus sign denotes that the indicated molecules were fluorescently labeled (green or red) or were unlabeled (black). +, 10 nM; ++, 40 nM; +++, 400 nM. Lanes 1-4 show migration of dCas9 protein alone (lanes 1 and 2), sgRNA alone (lane 3), or DNA substrate alone (lane 4) on the gel. The binary complex formed by dCas9 and sgRNA (lane 5) and the tertiary complex formed by dCas9, sgRNA, and DNA (lanes 6 and 8) migrated at distinct positions on the gel as indicated. dCas9 and DNA (lane 7) did not form a complex, because no new bands were detected on the gel. The addition of 10× unlabeled target DNA before complex formation (lane 10) resulted in about 10-fold less Cy5-DNA incorporated into the tertiary complex, as expected. (B, Left) The indicated fluorescent tertiary complex with Cy5-labeled sgMajSat target DNA was assembled in solution and incubated further at 37° C. for the indicated minutes with or without 30× unlabeled target DNA as competitor. (B, Right) The Cy5 fluorescent intensity of the bands corresponding to the tertiary complex was plotted as a histogram. The stability of the complex is evident from the lack of competition. Error bars represent SD of three independent experiments.
Figure 5B:
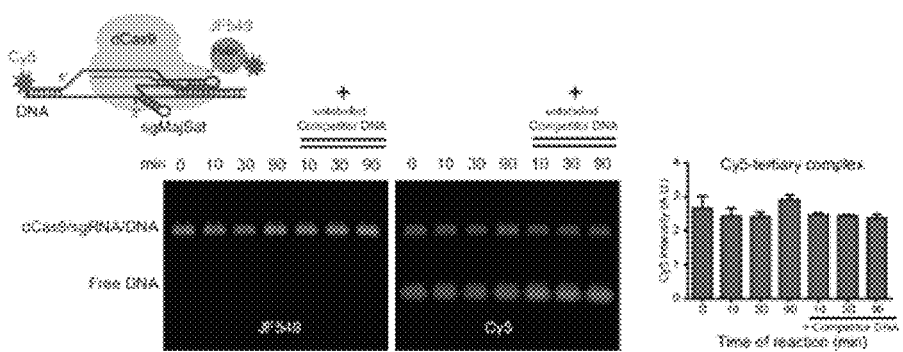
Figure 6A:
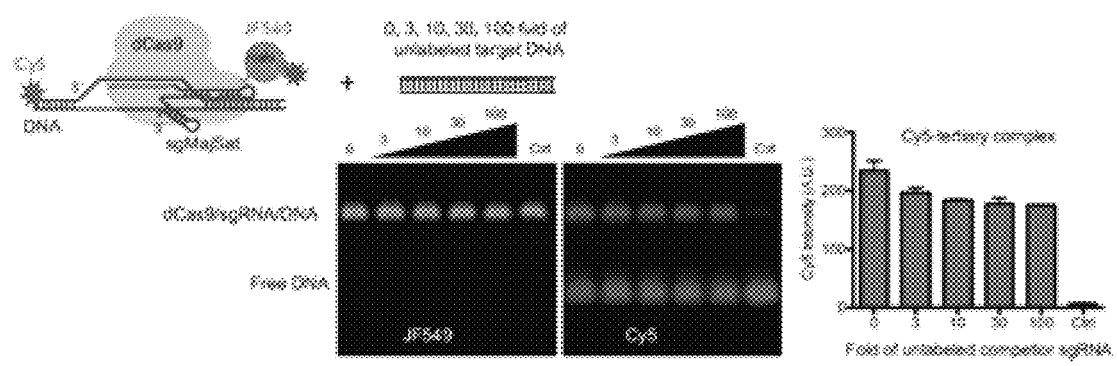
FIG. 6 includes Two-color CASFISH schematics, assays, histograms and imaging (A) Competition EMSA assessing the stability of the tertiary complex. (A, Left) The indicated fluorescent tertiary complex was assembled in solution and further incubated in 37° C. for 15 min with indicated fold-amounts of unlabeled sgMaj Sat target DNA as competitor. (A, Right) The fluorescent intensity of the bands of the tertiary complex plotted as a histogram. The stability of the complex is evident from the lack of competition. The control lane (ctrl) indicates the reaction product from a mixture of Cy5 DNA and 30-fold of unlabeled target DNA with dCas9/sgRNA binary complex. As expected, only a small fraction of Cy5-DNA was incorporated into the dCas9 tertiary complex. (B) Competition EMSAs assessing the stability of the binary complex. (B, Left) The indicated fluorescent binary complex was assembled at room temperature for 10 min and incubated further with the indicated fold-amounts of unlabeled sgMaj Sat at room temperature for 10 min. Unlabeled target DNA was added to the solution subsequently to form a tertiary complex followed by gel electrophoresis. (B, Right) The DY547 intensity of the bands of the tertiary complex plotted as a histogram. The stability of the binary complex of dCas9 and DY547-sgRNA is evident from the lack of competition. The control lane (ctrl) indicates the reaction product from the binary complex formed by a mixture of DY547-sgMaj Sat and 100-fold of unlabeled sgMaj Sat with dCas9 protein. As expected, only a small fraction of DY547-sgMaj Sat was incorporated into the dCas9 tertiary complex. (C) Schematic of two-color CASFISH methods. (D) Fluorescent imaging of sequential CASFISH against pericentromeres and telomeres in MEFs using the indicated JF549- or JF646-labeled dCas9 proteins and unlabeled sgRNAs. Results from sequential CASFISH are similar to those from one-step method. Maximum projection of z-stacks is shown. (Scale bars, 5 μM.) Error bars represent the SD of three independent experiments.

Simultaneous imaging of multiple chromatin domains or genes is critical for studying chromatin interactions. To explore the possibility of using CASFISH to detect multiple DNA targets simultaneously, we first investigated the binding of CASFISH probes to target DNA by electrophoretic mobility shift assays (EMSA). Using fluorescently labeled dCas9 protein, sgMaj Sat, and its target DNA, we found that dCas9 protein formed a binary complex with sgMaj Sat and a tertiary complex upon the addition of target DNA. These two complexes migrated on the gel as distinct bands away from free dCas9, free sgMaj Sat, or free target DNA (FIG. 5A) As expected, dCas9 showed no detectable interaction with target DNA in the absence of sgMaj Sat. To examine the stability of dCas9/sgMaj Sat binding to its target DNA, we carried out competition assays by adding excessive amounts of unlabeled target DNA to a preformed tertiary complex of JF549-dCas9/sgMaj Sat/Cy5-DNA. We found that incubation with increasing amounts of competitor DNA did not displace the Cy5-DNA from the preformed tertiary complex, as indicated by unchanged Cy5 fluorescence intensity of the tertiary complex even in the presence of a 100-fold excess of competitor DNA (FIG. 6A). Incubating preassembled tertiary complex with 30-fold of unlabeled competitor DNA for up to 1.5 h did not dissociate preformed tertiary complex either (FIG. 5A). These results demonstrated that, once bound to its DNA substrate, the Cas9/sgRNA/DNA complex is exceptionally stable. This prominent feature would allow a strategy of sequential CASFISH by subjecting cells to multiple rounds of CASFISH assays using probes labeled with different fluorochromes and targeting different DNA sequences.

Example 5: One Step MultiColor Imaging

Figure 6B:
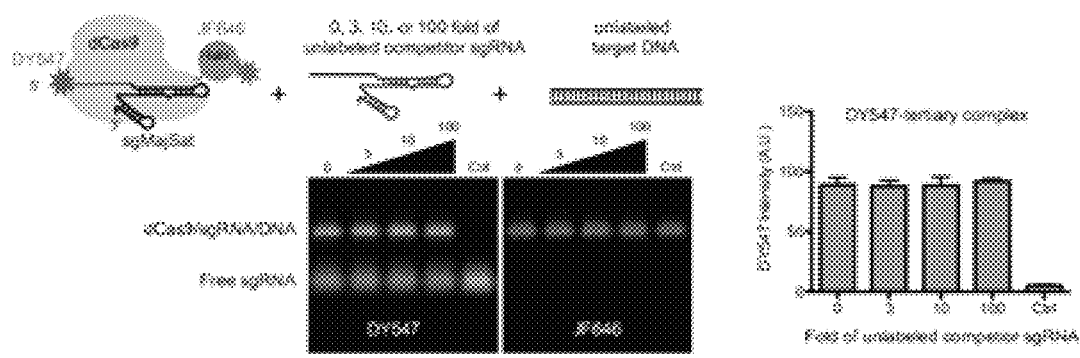
Figure 6C:
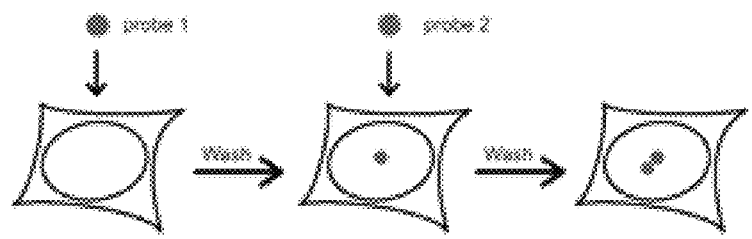
Figure 6C:
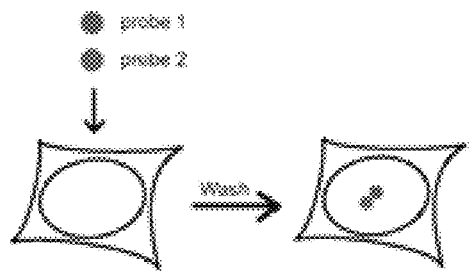
Figure 6D:
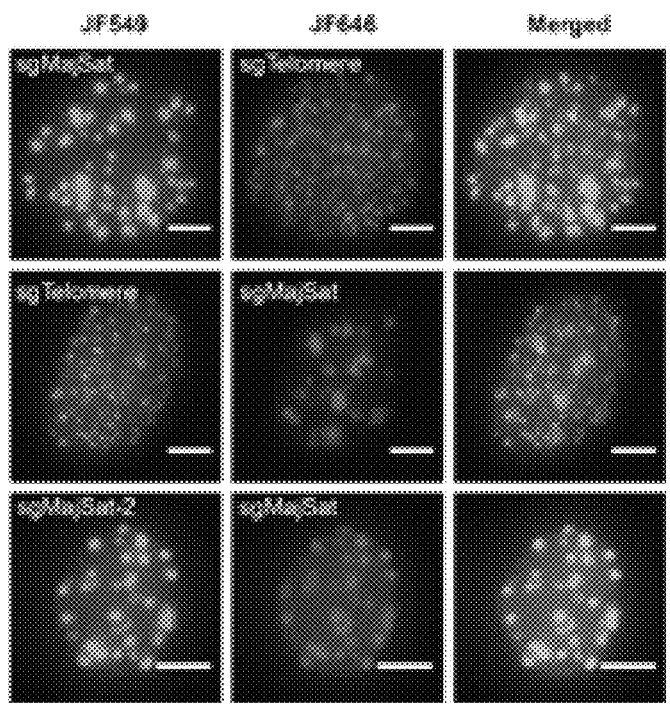
Figure 7:
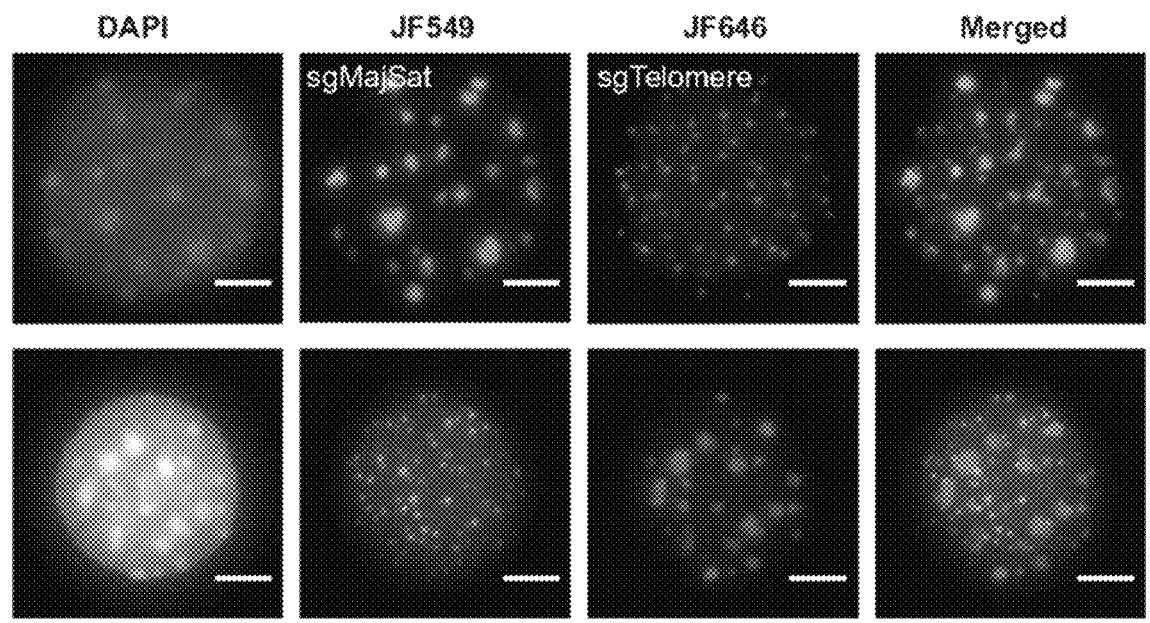
FIG. 7 is fluorescent imaging of pericentromeres and telomeres generated by one-step, two-color CASFISH using the indicated fluorescent dCas9 proteins and unlabeled sgRNAs. Maximum projection of z-stacks is shown. (Scale bars, 5 μM.).

To explore the possibility of applying multiple dCas9/sgRNA species in one step for multicolor imaging, we assessed the stability of the binary complex by sgRNA competition assay. We found that increasing amounts of competitor unlabeled sgRNA up to 100-fold did not displace the DY547-sgRNA from preassembled fluorescent dCas9/sgRNA, as indicated by the unchanged DY547 fluorescence intensity of the dCas9 complex (FIG. 6B). In contrast, adding unlabeled sgRNA competitor before the formation of the binary complex substantially reduced the incorporation of DY547-sgRNA to the dCas9 complex. These results demonstrated the high stability of the binary complex and the feasibility of one-step multicolor CASFISH. Therefore, we tested two methods for multicolor CASFISH: sequential rounds of CASFISH or a one-step application of multiple probes (FIG. 6C). Using JF549-dCas9/sgMaj Sat and JF646-dCas9/sgTelomere probes, we produced two-color imaging of pericentromeres and telomeres in cells with either the sequential CASFISH method (FIG. 6D) or the one-step method in which the two color probes are applied to the cell simultaneously (FIG. 7). There was no detectable cross-reactivity between the two imaging channels in either case. Probes with switched fluorescent labels gave the same results. As expected, CASFISH using two different sgRNAs targeting sgMaj Sat and sgMaj Sat-2 showed identical patterns (FIG. 6D). Thus we demonstrated that CASFISH could be used for imaging multiple sequence-specific genomic regions with multiple colors.

Example 6: CASFISH Sensitivity

Figure 8A:
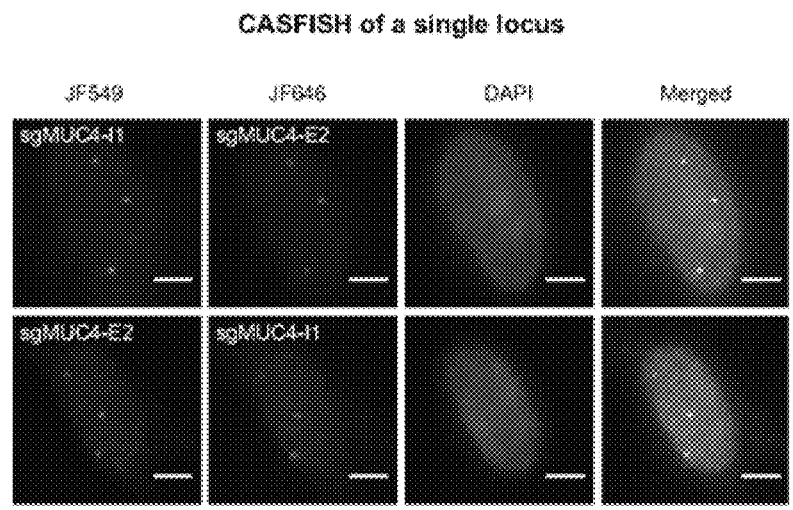
FIG. 8 includes CASFISH imaging of endogenous coding genes in human cells. (A) Fluorescent imaging of sequential CASFISH targeting two repetitive DNA sequences within intron 3 (sgMUC4-I1) or exon 2 (sgMUC4-E2) of the MUC4 gene. (B) Quantification of the number of MUC4 loci per cell and the total number of loci stained by sequential CASFISH against sgMUC4-I1 (green) and sgMUC4-E2 (red) as in A. n=80 cells. Loci labeled by both probes are colored yellow. (C) Fluorescent imaging of sequential CASFISH against the MUC4 and MUC1 genes. (D) Sequential CASFISH against repetitive intron 3 (sgMUC4-I1) and nonrepetitive intron 1 (sgMUC4-tiling) of the MUC4 gene. White arrowheads denote the labeled MUC4 genes. dCas9 was labeled by JF549 or JF646, as indicated. Maximum projection of z-stacks is shown. (Scale bars, 5 μM.)
Figure 8B:
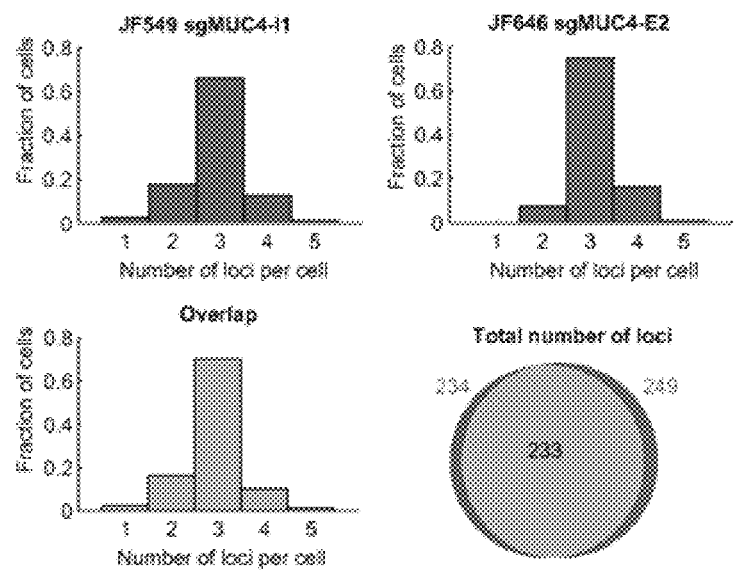
Figure 8C:
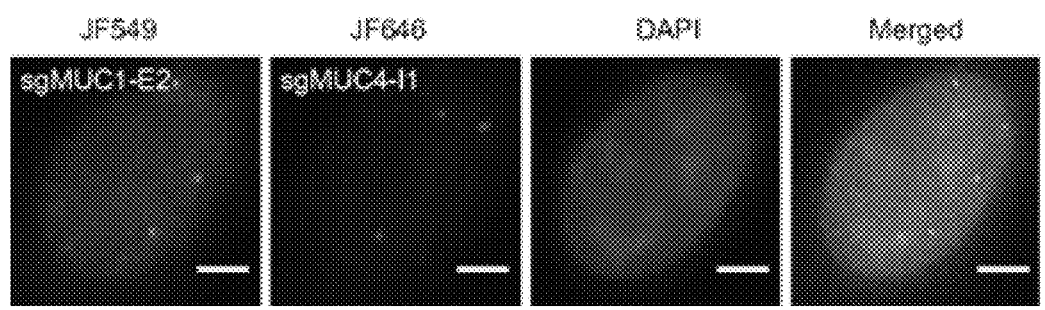
Figure 8D:
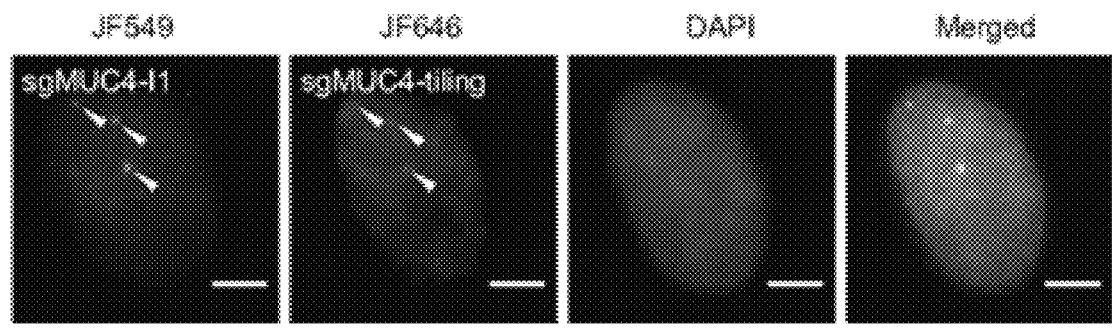
Figure 9A:
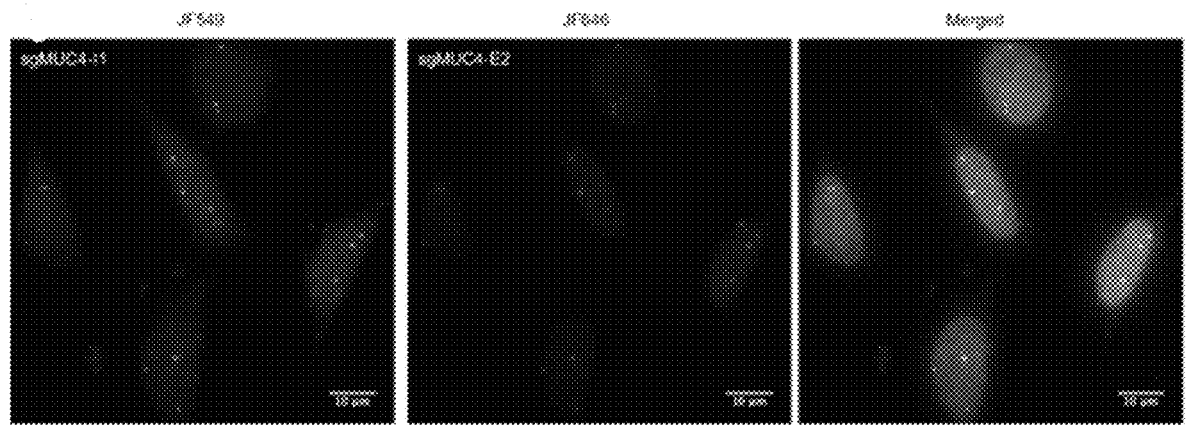
FIG. 9 includes investigations related to CASFISH sensitivity (A) Fluorescent imaging of a representative field of view of MUC4 CASFISH. All cells were labeled efficiently. Maximum projection of z-stacks is shown. (B) An example of MUC4 labeling in replicating cells. The fluorescent intensity of each spot was measured, and the background intensity was subtracted. Maximum projection of z-stacks is shown. (Scale bars, 5 µM.)
Figure 9B:
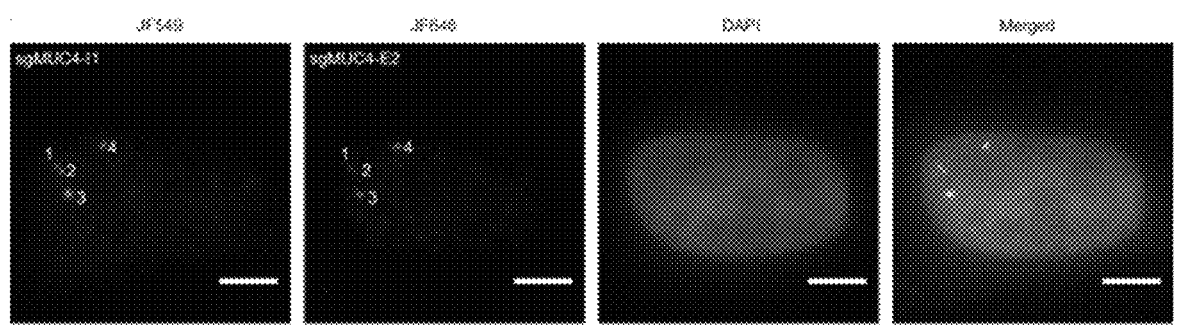

The major satellite and telomere sequences contain hundreds to thousands of repeats for sgRNA targeting. To assess the sensitivity of CASFISH, we tested sgRNAs against DNA substrates with lower copy numbers at the level of tens to hundreds. The human mucin 4 (MUC4) and mucin 1 (MUC1) genes contain repetitive sequences that have been imaged successfully in live cells with dCas9-EGFP (6). CASFISH using sgRNA against the ~400 copies of the target in exon 2 of the MUC4 gene (sgMUC4-E2) and ~45 copies of the target in intron 3 (sgMUC4-I1) detected prominent fluorescent puncta in all examined HeLa cell nuclei using either JF549- or JF646-labeled dCas9 protein (FIG. 8A and FIG. 9A). There are three fluorescent puncta in the majority of cells, as expected for the three copies of MUC4 loci in interphase HeLa cells (FIG. 8B). We also observed that labeling appeared weaker in sister chromatids (FIG. 9B, puncta 1 and 2) than in replicating sites in the same cells (FIG. 9B, puncta 3 and 4). Two-color sequential CASFISH using these two sgRNA produced puncta in close proximity, verifying that the signal was specific to MUC4 genes. Based on the fraction of loci labeled in both colors, we estimate the detection efficiency to be >94%. As a control, sequential CASFISH of the MUC4 and MUC1 genes (sgMUC4-I1 and sgMUC1-E1) showed distinct locations of these two genes in the nuclei (FIG. 8C), revealing no detectable cross-reactivity between sequential rounds of CASFISH probing. In summary, these results demonstrated that CASFISH is robust and efficient for the simultaneous and multiplexing labeling of multiple given genomic DNA sequences.

Example 7: CASFISH in Tissue

Figure 10A:
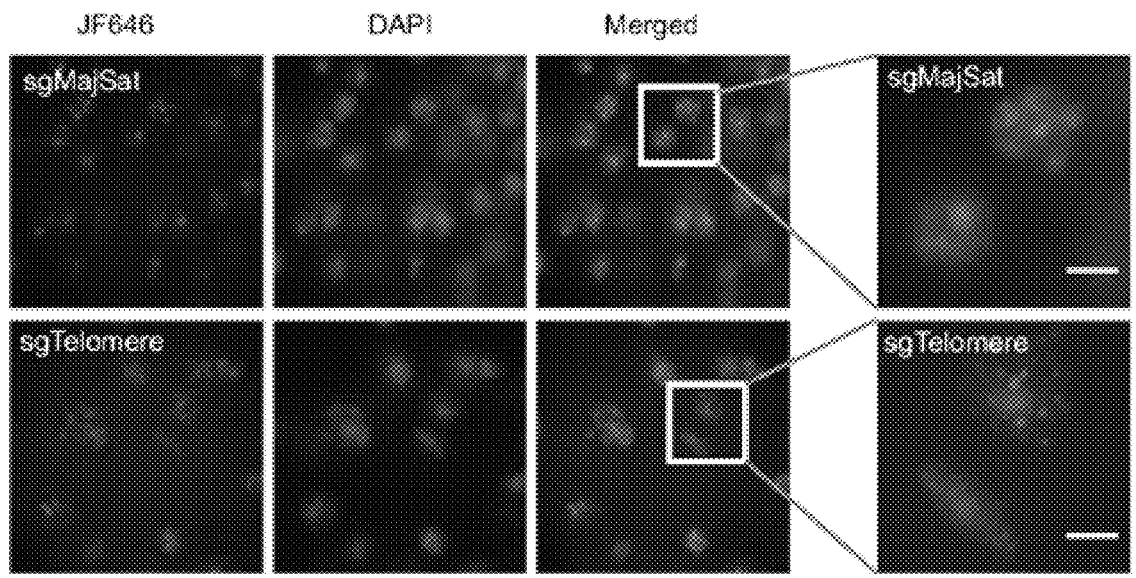
FIG. 10 CASFISH imaging on a tissue section and a fast CASFISH protocol. (A) CASFISH of mouse cryostat brain sections against major satellites and telomeres as indicated. (B, Left) Fifteen-minute and standard CASFISH of the MUC4 gene in HeLa cells. (B, Right) Intensity profiles across the labeled loci as indicated by the dotted lines on the left panel. dCas9 were labeled by JF646. Maximum projection of z-stacks is shown. (Scale bars, 5 µM.)
Figure 10B:
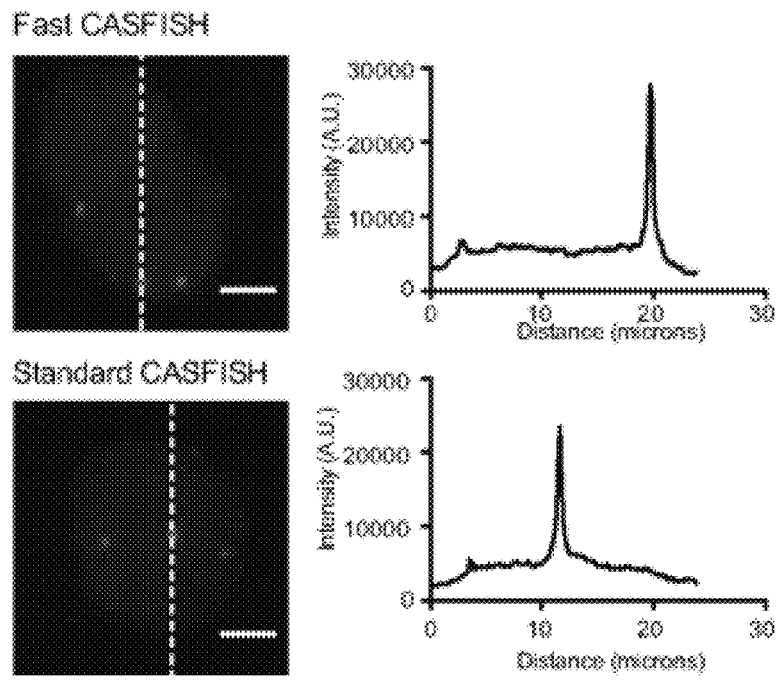

This example shows how a diagnostic procedure would be facilitated by a rapid and robust assay for genomic sequences present in tissue. To test whether CASFISH can be applied to tissue sections, we prepared cryostat sections of adult mouse brain and proceeded with CASFISH assays against pericentromeres and telomeres. The dCas9/sgRNA probes penetrated to 15 μm of the brain sections and efficiently labeled their targets in all examined cells (FIG. 10A). We envision that rapid detection of genomic elements by CASFISH could be advantageous in various scenarios, such as a rapid genetic diagnosis and detection of infectious agents. To derive an even more rapid CASFISH protocol, we reduced the reaction time of each step and achieved a 15-min protocol (5-min fixation and concurrent 5-min binary complex assembly, 5-min DNA binding, and 5-min washing between steps) using sgMUC-E2 as an example. The rapid protocol achieved robust labeling for the MUC4 gene, with most cells having three labeled puncta, as expected (FIG. 10A). The fluorescent intensity of the labeled locus was similar to that obtained by the standard protocol. These results suggested that CASFISH can be a rapid and robust method for visualizing specific genomic elements in cells and primary tissue. Detection of RNA can be developed utilizing a similar procedure.

SUMMARY

The CASFISH assay is rapid, cost-effective, and convenient (Table 4).

TABLE 4

Comparison of CASFISH with DNA FISH and live Cas9 imaging

|  | DNA FISH | Live Cas9 imaging | CASFISH |
|---|---|---|---|
| Probe | Nucleic acid probe | Genetically coded dCas9/sgRNA | In vitro assembled dCas9/sgRNA |
| Difficulty of probe generation | Reliable synthesis | Variable and time-consuming | Reliable synthesis |
| Experiment duration | Hours to days | Immediately | Minutes to 1 h |
| Color | Multicolor | One color per CRISPR system | Multicolor per CRISPR system |
| High-throughput multiplexing | Yes | Challenging | Yes |
| Global DNA denaturation | Yes | No | No |
| Fixed cell imaging | Yes | No | Yes |
| Live cell imaging | No | Yes | Possible |
| Tissue imaging | Yes | Possible | Yes |

First, CASFISH takes advantage of the CRISPR-based mechanism for rapid DNA hybridization. This enzymatic probe is more efficient than the nuclei-acid-only probe of DNA FISH that requires heat and formamide treatment to denature dsDNA. Thus, while DNA FISH takes hours or longer, CASFISH can be as fast as 15 min under optimized conditions. Second, the mild conditions of CASFISH (room temperature and 37° C.) can better preserve cell morphology and DNA structure, and thus CASFISH can be a useful tool for studying genome organization combined with single-molecule superresolution imaging. Third, the two-component nature of CASFISH probes provides great potential for multiplexing and room for further engineering (FIG. 11). Halo tagging of dCas9, as demonstrated in this study, allows the ease and flexibility of fluorescent labeling for various imaging purposes. A single reagent of labeled dCas9 protein can be assembled with a number of customized unlabeled sgRNAs at minimal cost. CASFISH therefore can be used to interrogate multiple targets with multiple single colors or with combinatory color codes, facilitating studies of spatial relationships of multiple distinct genomic loci. The fast-binding kinetics of CASFISH probes to targets and the mild reaction conditions would allow highly multiplexed DNA profiling in single cells. In addition, the protein moiety of CASFISH probes provides room for exploring other labeling methods and incorporating multiple fluorochromes per molecule to achieve higher sensitivity and specificity. Fourth, CASFISH holds great potential for applications. CASFISH can be advantageous in detecting "difficult" DNA FISH sequences as exemplified by G-rich telomeres. CASFISH can be potentially advantageous in detecting subtle DNA variations such as SNPs because the sgRNA sequence composition near the protospacer adjacent motif (PAM) is sensitive to permutation. The CASFISH strategy allows delivery of fluorescent dCas9 protein coupled with unlimited numbers of sgRNA, thereby allowing the labeling of gene loci and chromatin domain of any given size. In principle, customized CASFISH probes can be delivered to live cells via direct microinjection or protein delivery methods to allow studies of native chromatin organization. CASFISH is rapid and applicable to primary tissue, thus offering advantages for rapid genetic diagnosis such as the detection of DNA translocations. The CASFISH assay can also be expanded to orthogonal CRISPR systems, allowing a wide range of reagent development and providing an opportunity for developing combinatorial, multiplexed, multicolor imaging systems.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Hübner M R, Eckersley-Maslin M A, Spector D L (2013) Chromatin organization and transcriptional regulation. Curr Opin Genet Dev 23(2):89-95.
2. Levsky J M, Singer R H (2003) Fluorescence in situ hybridization: Past, present and future. J Cell Sci 116(Pt 14):2833-2838.
3. Beliveau B J, et al. (2012) Versatile design and synthesis platform for visualizing genomes with Oligopaint FISH probes. Proc Natl Acad Sci USA 109(52):21301-21306. Abstract/FREE Full Text
4. Sternberg S H, Doudna J A (2015) Expanding the Biologist's Toolkit with CRISPR-Cas9. Mol Cell 58(4):568-574.
5. Mali P, Esvelt K M, Church G M (2013) Cas9 as a versatile tool for engineering biology. Nat Methods 10(10):957-963.
6. Chen B, et al. (2013) Dynamic imaging of genomic loci in living human cells by an optimized CRISPR/Cas system. Cell 155(7):1479-1491.
7. Tanenbaum M E, Gilbert L A, Qi L S, Weissman J S, Vale R D (2014) A protein-tagging system for signal amplification in gene expression and fluorescence imaging. Cell 159(3):635-646.
8. Ma H, et al. (2015) Multicolor CRISPR labeling of chromosomal loci in human cells. Proc Natl Acad Sci USA 112(10):3002-3007.
9. Sternberg S H, Redding S, Jinek M, Greene E C, Doudna J A (2014) DNA interrogation by the CRISPR RNA-guided endonuclease Cas9. Nature.
10. Encell L P, et al. (2012) Development of a dehalogenase-based protein fusion tag capable of rapid, selective and covalent attachment to customizable ligands. Curr Chem Genomics 6:55-71.
11. Grimm J B, et al. (2015) A general method to improve fluorophores for live-cell and single-molecule microscopy. Nat Methods 12(3):244-250, 3, 250.
12. Ziegler-Birling C E L, Miyanari Y, Torres-Padilla M-E (2013) Live visualization of chromatin dynamics with fluorescent TALEs. Nat Struct Mol Biol 20:1321-1324.
13. Shi X, et al. (2012) Quantitative fluorescence labeling of aldehyde-tagged proteins for single-molecule imaging. Nat Methods 9(5):499-503.
14. Zijlmans J M, et al. (1997) Telomeres in the mouse have large inter-chromosomal variations in the number of T2AG3 repeats. Proc Natl Acad Sci USA 94(14):7423-7428.
15. O'Connell M R, et al. (2014) Programmable RNA recognition and cleavage by CRISPR/Cas9. Nature.
16. Beliveau B J, et al. (2015) Single-molecule super-resolution imaging of chromosomes and in situ haplotype visualization using Oligopaint FISH probes. Nat Commun 6:7147.
17. Chen K H, Boettiger A N, Moffitt J R, Wang S, Zhuang X (2015) RNA imaging. Spatially resolved, highly multiplexed RNA profiling in single cells. Science 348(6233):aaa6090.
18. Hsu P D, et al. (2013) DNA targeting specificity of RNA-guided Cas9 nucleases. Nat Biotechnol 31(9):827-832.
19. Esvelt K M, et al. (2013) Orthogonal Cas9 proteins for RNA-guided gene regulation and editing. Nat Methods 10(11):1116-1121.
20. Jinek M, et al. (2012) A programmable dual-RNA-guided DNA endonuclease in adaptive bacterial immunity. Science 337(6096):816-821.
21. Schneider C A, Rasband W S, Eliceiri K W (2012) NIH Image to ImageJ: 25 years of image analysis. Nat Methods 9(7):671-675.
22. Janicki S M, et al. (2004) From silencing to gene expression: Real-time analysis in single cells. Cell 116 (5):683-698.
23. Gilbert et al., CRISPR-mediated modular RNA-guided regulation of transcription in eukaryotes, Cell, 2013 vol. 154(2) pp. 442-51.
24. Anton, et al., (2014) "Visualization of specific DNA sequences in living mouse embryonic stem cells with a programmable fluorescent CRISPR/Cas system," Nucleus 5(2): 163-72.
25. Van der Oost, et al., (2014) "Unravelling the structural and mechanistic basis of CRISPR-Cas systems," Nat Rev Microbiol, 12(7): 479-92.
26. Wright, et al., (2015) "Rational design of a split-Cas9 enzyme complex," Proc Natl Acad Sci USA, 112(10): 2984-89.
27. U.S. Pat. No. 8,697,359 to Zhang for "CRISPR-Cas systems and methods for altering expression of gene products."

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of customizing a probe for detecting a nucleic acid sequence, comprising:
   providing a polypeptide comprising the sequence of SEQ ID NO: 2 or SEQ ID NO: 4, which includes a Cas9 polypeptide and a tag configured to bind a secondary label;
   selecting and attaching the secondary label to the Cas9 polypeptide via the tag to create a labeled Cas9 polypeptide;
   providing a gRNA specific for a selected target nucleic acid;
   combining the labeled Cas9 polypeptide and the gRNA in a composition, such that the labeled Cas9 polypeptide to gRNA molar ratio is from 1:1 to 1:20, wherein the labeled Cas9 polypeptide and the gRNA form a complex for use as a probe for detecting the target nucleic acid.

2. The method of claim 1, wherein the secondary label comprises a synthetic dye that is not a fluorescent protein.

3. The method of claim 1, wherein the gRNA is unlabeled.

4. The method of claim 1, wherein the Cas9 polypeptide to gRNA molar ratio is from 1:1 to 1:4.

5. A method of detecting a target nucleic acid in a sample, comprising:
   providing a composition comprising
      a polypeptide comprising the sequence of SEQ ID NO: 2 or SEQ ID NO: 4, which includes a Cas9 polypeptide and a tag,
      a gRNA specific for a target nucleic acid, and
      a secondary label attached to the Cas9 polypeptide via the tag to provide a labeled Cas 9 polypeptide,
      wherein the labeled Cas9 polypeptide to gRNA molar ratio is from 1:1 to 1:20, and the Cas9 polypeptide and the gRNA form a complex;
   contacting the composition with a sample containing genetic material such that the complex can bind target nucleic acid within the sample; and
   detecting the secondary label to identify binding between the complex and the target nucleic acid.

6. The method of claim 5, and further comprising imaging the sample to determine the location and the relative copy number of the target nucleic acid sequence.

7. The method of claim 5, wherein the sample is selected from chromosome spreads for genetic testing, cultures, prenatal materials, samples for in vitro fertilization, swabs, air filters, water cooling towers, food, drink, hair, stool, urine, saliva, blood, lymph, sputum, cervical smears, sperm, sections of tissues from biopsies, sections of tissues from autopsies, and combinations thereof.

8. The method of claim 5, wherein the sample includes cells, and further comprising performing the contacting step by a method selected from the group consisting of bead loading, microinjection, nanoparticle or lipid mediated transduction, and combinations thereof.

9. The method claim 5, wherein the sample is a cell.

10. The method of claim 9, wherein the cell is a live cell.

11. The method of claim 5, wherein the sample is a tissue sample.

12. The method of claim 5, wherein the sample comprises a cell or tissue, and the method further comprises fixing the sample by contacting the sample with a solution of methanol and acetic acid at a 1:1 ratio; and washing the sample prior to contacting the sample with the composition.

13. The method of claim 5, wherein the secondary label include a first dye having a first emission color, wherein the method further comprises
   providing a second Cas9 polypeptide with a second tag bound to the second Cas9 polypeptide and a second dye having a second emission color attached to the second Cas9 polypeptide via the second tag to create a second labeled Cas9 polypeptide;
   providing a second gRNA specific for a selected second target nucleic acid;
   combining the second labeled Cas9 polypeptide and the second gRNA in a second composition, such that the amount of the second gRNA in the second composition is equal to or greater than the amount of the second labeled Cas9 polypeptide in the second composition, wherein the second labeled Cas9 polypeptide and the second gRNA form a second complex for use as a second probe for detecting the second target nucleic acid; and
   combining the first complex and the second complex to obtain a combination composition for detecting the target nucleic acid and the second target nucleic acid.

14. The method of claim 13, wherein the Cas9 polypeptide and the second Cas9 polypeptide are the same species of Cas9 polypeptide.

15. The composition of claim 14, wherein the species of Cas9 polypeptide is *Streptococcus pyogenes* Cas9 (spCas9).

16. The method of claim 5, wherein the Cas9 polypeptide to gRNA molar ratio is from 1:1 to 1:4.

* * * * *